(12) United States Patent
Wudil et al.

(10) Patent No.: US 12,360,048 B2
(45) Date of Patent: Jul. 15, 2025

(54) APPARATUS AND METHODS FOR THE ESTIMATION OF SOIL UNCONFINED COMPRESSIVE STRENGTH USING LASER-INDUCED SPECTROSCOPY

(71) Applicant: KING FAHD UNIVERSITY OF PETROLEUM AND MINERALS, Dhahran (SA)

(72) Inventors: Yakubu Sani Wudil, Dhahran (SA); Mohammed A. Al-Osta, Dhahran (SA); Omar S. Baghabra Al-Amoudi, Dhahran (SA); Muhammad A. Gondal, Dhahran (SA); Osama Atef Al Najjar, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 140 days.

(21) Appl. No.: 18/485,748

(22) Filed: Oct. 12, 2023

(65) Prior Publication Data
US 2025/0123214 A1    Apr. 17, 2025

(51) Int. Cl.
*G01N 21/71* (2006.01)
*G01N 21/25* (2006.01)
(Continued)

(52) U.S. Cl.
CPC ......... *G01N 21/718* (2013.01); *G01N 21/255* (2013.01); *G01N 33/24* (2013.01);
(Continued)

(58) Field of Classification Search
CPC .... G01N 21/718; G01N 21/255; G01N 33/24; G01N 2021/0339; G01N 2201/06113; G01N 2201/0697
See application file for complete search history.

(56) References Cited

U.S. PATENT DOCUMENTS

2022/0137024 A1* 5/2022 Chantz ................. G01N 33/24
702/7

FOREIGN PATENT DOCUMENTS

CN    114034684 A    2/2022

OTHER PUBLICATIONS

Huong Thi Thanh Ngo, et al., "Application of Artificial Intelligence to Determined Unconfined Compressive Strength of Cement-Stabilized Soil in Vietnam", Applied Sciences, vol. 11, Issue 4, Feb. 23, 2021, pp. 1-20.
(Continued)

*Primary Examiner* — Tony Ko
(74) *Attorney, Agent, or Firm* — Oblon, McClelland, Maier & Neustadt, L.L.P.

(57) ABSTRACT

A field portable device for determining the unconfined compressive strength of a soil sample includes a sample holder, a heating device, a scale, a spectrometer, and a microprocessor. The sample holder receives a soil sample. The heating device dries the soil sample for a specified time. The scale measures a weight of the soil sample and a dried weight of the soil sample. The spectrometer performs laser induced breakdown spectroscopy on the soil sample and generates spectral emission intensities of the soil sample. The microprocessor calculates a bulk density and a water content of the soil sample, actuates the spectrometer to generate the spectral emission intensities. The microprocessor applies the spectral emission intensities, the bulk density and the water content to a trained machine learning regressor combined with an adaptive boosting classifier to predict the unconfined compressive strength of the soil sample.

20 Claims, 31 Drawing Sheets

(51) Int. Cl.
  *G01N 33/24* (2006.01)
  *G01N 21/03* (2006.01)
(52) U.S. Cl.
  CPC ............... *G01N 2021/0339* (2013.01); *G01N 2201/06113* (2013.01); *G01N 2201/0697* (2013.01)

(56) References Cited

OTHER PUBLICATIONS

Hai-Bang Ly, et al., "Soil Unconfined Compressive Strength Prediction Using Random Forest (RF) Machine Learning Model", The Open Construction & Building Technology Journal, vol. 14, Issue Suppl-2, M3, 2020, pp. 278-285.

E.U. Eyo, et al., "Machine learning regression and classification algorithms utilised for strength prediction of OPC/by-product materials improved soils", Construction and Building Materials, vol. 284, Article ID: 122817, May 17, 2021, pp. 1-16.

* cited by examiner

APPARATUS AND METHODS FOR THE ESTIMATION OF SOIL UNCONFINED COMPRESSIVE STRENGTH USING LASER-INDUCED SPECTROSCOPY

STATEMENT REGARDING PRIOR DISCLOSURE BY THE INVENTORS

Aspects of this technology are described in an article "Investigating the Soil Unconfined Compressive Strength Based On Laser-Induced Breakdown Spectroscopy Emission Intensities and Machine Learning Techniques" published in American Chemical Society, 2023, on Jul. 14, 2023, which is incorporated herein by reference in its entirety.

STATEMENT OF ACKNOWLEDGEMENT

The inventor(s) acknowledge the financial support provided by King Fahd University of Petroleum and Minerals (KFUPM), Riyadh, Saudi Arabia through Project #INCB2216 and King Abdullah City for Atomic and Renewable Energy (K.A.CARE) Energy Research & Innovation Center, Dhahran, Saudi Arabia through Project #DSR-IRC-CBM.

BACKGROUND

Technical Field

The present disclosure is directed to a device, method and system for estimation of soil unconfined compressive strength based on laser-induced breakdown spectroscopy emission intensities with a trained machine learning regressor including a decision tree regressor (DTR) combined with an adaptive boosting (ADB) classifier.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In geotechnical engineering, understanding soil mechanics is of paramount importance. Unconfined compressive strength (UCS) is a measure of the resistance of soil to compression. The UCS is defined as the maximum stress that can be applied to a soil sample before it fails. The UCS is a fundamental structural parameter that finds applications in the design of many geotechnical structures such as earth dams, bridges, railways, tunnels, buildings, pavements, and road foundations. In civil engineering, knowledge of the UCS enables engineers to identify the behavior of a particular soil such that an appropriate solution can be find out accordingly to provide essential stability and safety of civil engineering structures. Conventional UCS measuring methods include manual digging and excavation, using a physical property measurement setup in a laboratory, using specialized equipment such as ground-penetrating radar (GPR) and electrical resistivity tomography (ERT). However, these methods are time-consuming, costly, and prone to provide inaccurate results.

As an improvement, several in situ soil testing methods were introduced that involve analyzing soil samples directly in a field or in situ, rather than extracting and transporting these samples to the laboratory. However, the in situ soil testing methods have several disadvantages, such as limited applicability, low efficiency, difficulty in monitoring, and potential adverse effects on the soil quality and microorganisms.

Laser-induced breakdown spectroscopy (LIBS) is an effective technique for in-line monitoring by investigating the elemental composition of a soil sample using laser-induced plasma. Rapid spectral data analysis allows LIBS to be applied for an in-line monitoring. However, identifying different types of samples with similar elemental compositions using LIBS is challenging. Therefore, machine learning and deep learning methods were adopted to improve the accuracy and speed of LIBS.

An end-to-end soil analysis method based on LIBS has been described that employs a Convolutional Neural Network (CNN) model for soil analysis (See: Xu, X.; Ma, F.; Zhou, J.; Du, C., "*Applying convolutional neural networks (CNN) for end-to-end soil analysis based on laser-induced breakdown spectroscopy (LIBS) with less spectral preprocessing*", Comput. Electron. Agric. 2022, 199, 107171). This analysis method employs statistical equations between soil properties for estimating the unconfined compressive strength of soil. However, these statistical equations are often limited by oversimplification, assumptions, and dependency on specific soil types or conditions.

A soil spectroscopy method using chemometrics has been described that analyzes spectroscopic data for predicting soil properties. (See: Barra, I.; Haefele, S. M.; Sakrabani, R.; Kebede, F., "*Soil Spectroscopy with the Use of Chemometrics, Machine Learning and Pre-Processing Techniques in Soil Diagnosis: Recent Advances—a Review*", Trends in Analytical Chemistry, Volume 135, February 2021, Article number 116166). This method relies on assumptions about linearity and therefore struggles to capture the complex non-linear relationships present in the soil data. Additionally, the interpretability of this method is limited, making it challenging to gain insights into the underlying soil composition and unconfined compressive strength.

Further, a hybrid artificial neural network (ANN)-based technique has been described to predict the cohesion of sandy soil combined with fiber. (See: Armaghani, D. J.; Mirzaei, F., "*Nguyen-Thoi, T. Hybrid ANN Based Techniques in Predicting Cohesion of Sandy-Soil Combined with Fiber*," Geomech. Eng. 2020, 20, 191-205). However, the hybrid ANN utilizes feedforward neural networks, which can be computationally expensive and require a large number of parameters and layers, leading to limited practical applications.

Hence, there is a need for a field portable device that determines the unconfined compressive strength of the soil by employing a robust artificial intelligence approach with a compact and rugged device which generates a result with a high degree of accuracy.

SUMMARY

In an embodiment, a field portable device for determining the unconfined compressive strength of a soil sample is described. The field portable device for determining the unconfined compressive strength of a soil sample. The field portable device includes a sample holder, a heating device, a scale, a spectrometer, a display screen, a power source, and a microprocessor. The sample holder is configured to receive a soil sample. The sample holder has a defined volume. The heating device is configured to dry the soil sample for a specified time. The scale is connected to the sample holder. The scale is configured to measure a weight of the soil sample and a dried weight of the soil sample. The spectrometer is configured to perform laser induced breakdown spectroscopy on the soil sample and generate spectral emission intensities of the soil sample. The microprocessor is connected to the scale, the heating device, the spectrometer, the display screen and the power source. The microprocessor includes circuitry, a memory and programming instructions stored therein that, when executed by one or more processors, cause the one or more processors to: calculate a bulk density of the soil sample; calculate a water content of the soil sample; actuate the spectrometer to perform laser induced breakdown spectrometry on the soil sample and generate the spectral emission intensities; apply the spectral emission intensities, the bulk density and the water content of each soil sample as input features to a trained decision tree regressor combined with an adaptive boosting classifier; predict the unconfined compressive strength of the soil sample; and display the unconfined compressive strength, the bulk density, the water content and the spectral emission intensities of the soil sample on the display screen.

In another exemplary embodiment, a method for surveying a geographic area to determine an unconfined compressive strength of a soil layer of the geographic area is described. The method includes transporting a field portable device equipped with a microprocessor configured to determine the unconfined compressive strength of soil samples to the geographic location. The method includes collecting, with an auger, a soil sample of the soil layer. The method includes depositing the soil sample into a sample holder of the field portable device, wherein the sample holder has a defined volume. The method includes recording, with a scale connected to the sample holder, an undried weight of the soil sample. The method includes drying, with a heating device, the soil sample for a specified time. The method includes recording, with the scale, a dried weight of the soil sample. The method includes performing, with a laser induced breakdown spectrometer, laser induced breakdown spectroscopy (LIBS) on the soil sample to generate spectral emission intensities of the soil sample. The method includes recording, by a global positioning system (GPS) receiver, a location of the soil sample. The method includes calculating, with a microprocessor connected to the scale, the laser induced breakdown spectrometer and the GPS receiver to receive the undried weight, the dried weight, the spectral emission intensities and the location of the soil sample respectively, the bulk density and the water content of the soil sample. The method includes applying, by the microprocessor, the bulk density, water content and spectral emission intensities to a trained decision tree regressor combined with an adaptive boosting classifier. The method includes predicting, by the trained decision tree regressor combined with an adaptive boosting classifier, the unconfined compressive weight of the soil sample. The method includes displaying, on a display screen operatively connected with the microprocessor, the unconfined compressive strength, the bulk density, the water content and the spectral emission intensities of the soil sample.

In another exemplary embodiment, a method of determining an unconfined compressive strength of a soil sample is described. The method includes receiving a set of soil samples. The method includes performing laser induced breakdown spectroscopy on each soil sample to generate spectral emission intensities of each soil sample of the set of soil samples. The method further includes measuring a bulk density of each soil sample of the set of soil samples. The method further includes measuring a water content of each soil sample of the set of soil samples. The method further includes applying the spectral emission intensities, the bulk densities and the water contents of each soil sample as input features to a trained machine learning regressor combined with an adaptive boosting classifier. The method further includes determining, by the trained machine learning regressor combined with the adaptive boosting classifier, the unconfined compressive strength of each of the soil samples.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
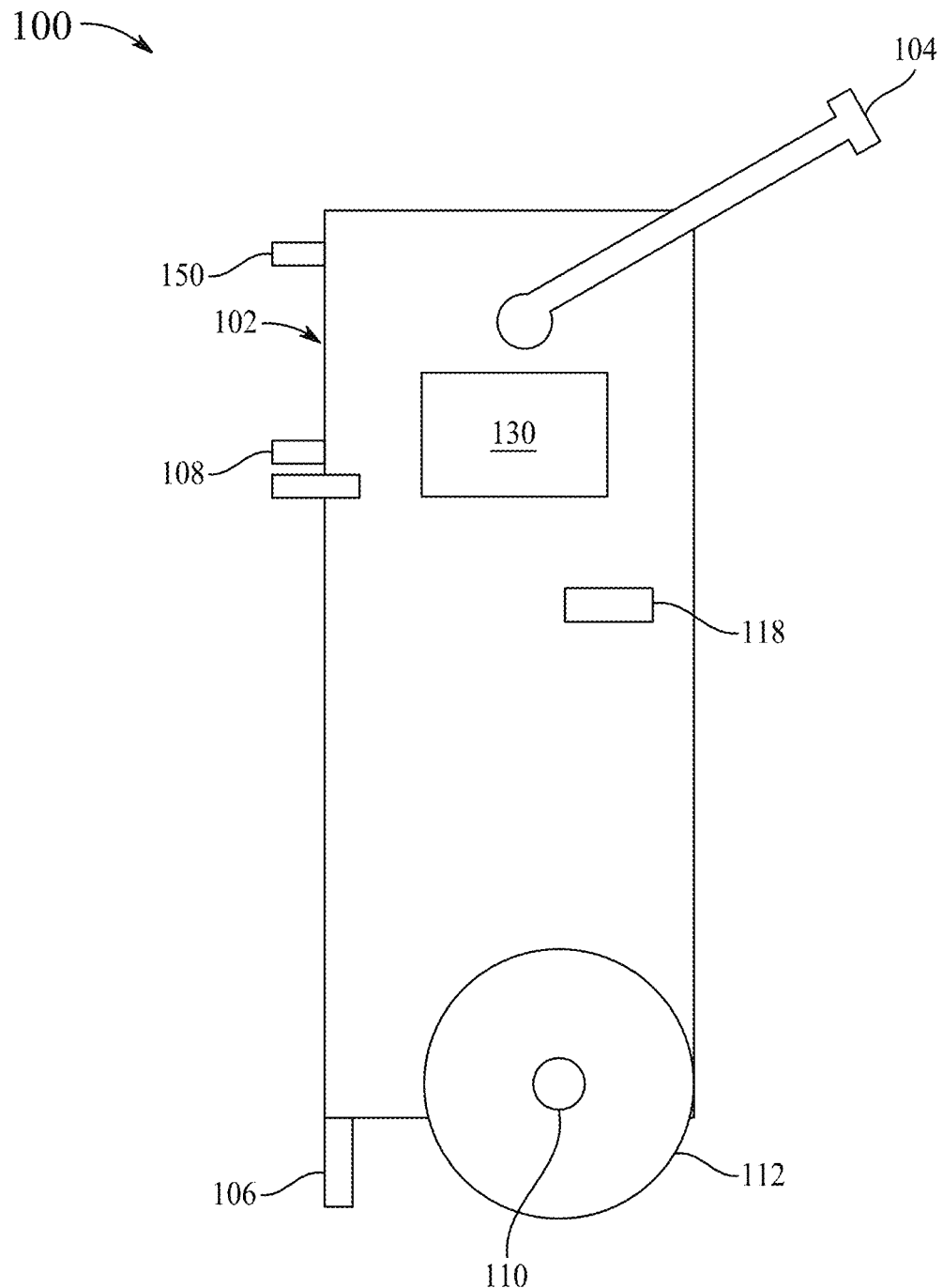
FIG. 1A illustrates an exemplary outer view of a field portable device for determining the unconfined compressive strength (UCS) of a soil sample, according to aspects of the present disclosure.

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

Aspects of this disclosure are directed to a field portable device, and a method for determining the unconfined compressive strength (UCS) of a soil sample. The field portable device is configured to employ laser-induced breakdown spectroscopy (LIBS) and machine learning approaches for determining the UCS of the soil sample. The LIBS is employed to investigate the constituent elements present in the soil sample and their respective concentrations. Subsequently, the machine learning approach is configured to use data generated by the LIBS, for example, the generated data includes emission intensities of selected constituent elements, soil water content, and bulk density as input features (input descriptors). In the initial stage of experimentation, a decision tree regression (DTR) based model and a support vector regression (SVR) based model with a radial basis function were used to predict the UCS of the soil. In a later stage of experiments, an adaptive boosting (ADB) classifier was used along with the DTR based model and the SVR based model to improve the performance of each of the two models. Further, the models (SVR, boosted SVR, DTR, and boosted DTR) were evaluated based on the standard metric indicators, i.e., mean absolute error, correlation coefficient, root mean square error, and coefficient of determination ($R^2$-score). The $R^2$-scores obtained for SVR model, boosted SVR model, DTR model, and boosted DTR model were 95.28%, 95.22%, 98.98%, and 99.03%, respectively, during the testing phase. The results indicate that the boosted DTR model outperformed the rest of the models in predicting the UCS. The models were validated by studying external systems whose data was not involved in the training phase or the testing phase. The soil samples were further stabilized with cement and lime to improve their strength. The LIBS emission intensities of such cement-stabilized and lime-stabilized samples were used to confirm the validity of the models and ensure their generalization strength. A high degree of accuracy was achieved in the prediction of soil strength using the developed models, therefore highlighting their potential for application in geotechnical engineering. Dimensionality reduction (transformation of data from a high-dimensional space into a low-dimensional space) may be applied to narrow down the input descriptors and reduce the computational cost.

In various aspects of the disclosure, non-limiting definitions of one or more terms that will be used in the document are provided below.

The term "mean absolute error (MAE)" represents the average variance between the significant values in the dataset and the projected values in the same dataset.

The term "mean squared error (MSE)" represents the average of the square of the difference between the actual values and the estimated values.

The term "coefficient of determination (R-squared or $R^2$)" represents how well the values fit compared to the original values. The values from 0 to 1 are interpreted as percentages.

The term "root mean squared error (RMSE)" represents the square root of the mean of the square of all of the error.

The term "hyperparameters" refers to parameters whose values control the learning process and determine the values of model parameters that a learning algorithm ends up learning.

Figure 1B:
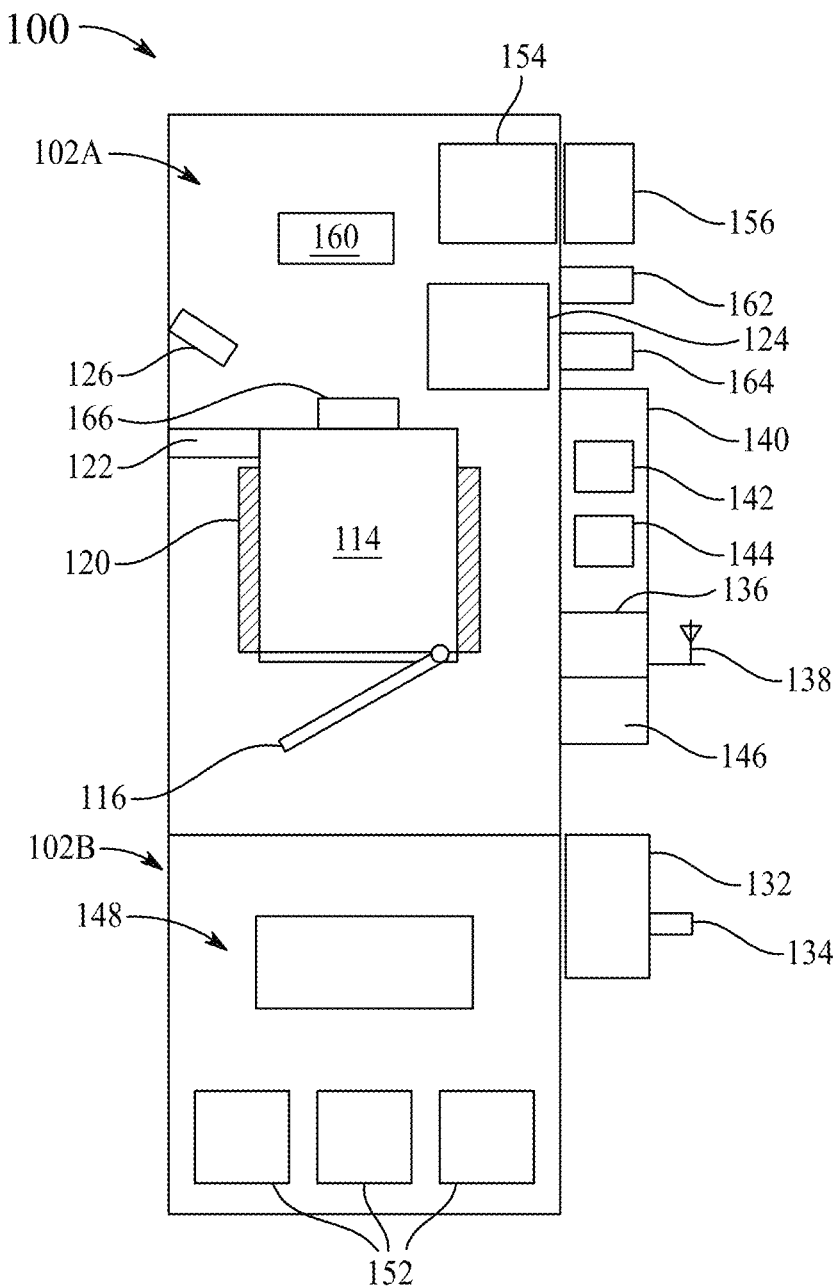
FIG. 1B illustrates a detailed inner view of the field portable device, according to aspects of the present disclosure.

FIG. 1A-FIG. 1B illustrate an overall configuration a field portable device 100. FIG. 1A illustrates an exemplary outer view of the field portable device 100 for determining the unconfined compressive strength (UCS) of a soil sample (hereinafter interchangeably referred to as "the device 100"), according to one or more aspects of the present disclosure. FIG. 1B illustrates an exemplary inner view of the device 100, according to aspects of the present disclosure. As shown in FIG. 1A-FIG. 1B, the device 100 includes a number of components such as an elongated housing 102, a sample holder 114, a heating device 120, a scale 122, a spectrometer 124, a display screen 130, a power source 132, and a microprocessor 140.

The elongated housing 102 is configured to contain various components of the device 100. For example, but not by way of limitation, the elongated housing 102 of the present invention may be square, rectangular, oval, round, elliptical, triangular, hexagonal, or octagonal shapes, or any other polygonal shape, or any combination of such shapes. The elongated housing 102 is made of material that is rust-free, or non-rusting, corrosion-resistant and/or acid-resistant. The elongated housing 102 may be made of plastic, an insulating material, or metal, such as galvanized steel.

In an aspect, the elongated housing 102 includes a front side, a back side, a top side, a bottom side, and two peripheral sides. The elongated housing 102 includes two sections: a top section 102A, and a bottom section 102B.

The elongated housing 102 is configured to enclose a hopper 148, located in the bottom section 102B of the housing 102. For example, the hopper 148 is located beneath the sample holder 114. In an example, the hopper 148 includes a plurality of openings to discharge the received soil to a plurality of barcoded bags 152, located within the bottom section 102B. The hopper 148 is configured to receive the soil sample from the sample holder 114 and store the received sample in one of the plurality of barcoded bags 152 for further processing. In an aspect, the bottom section 102B of the housing 102 includes a receiving region on a bottom side of the elongated housing 102. The receiving region is configured to hold and/or release the plurality of barcoded bags 152 for easy removal. In some embodiments, the collected soil sample may be analyzed by a soil sensor and/or may be transferred to a collection location (e.g., laboratory) for cataloging and further analysis.

The elongated housing 102 includes a handle 104, a front support 106, an axle 110, and a plurality of wheels 112. The handle 104 is disposed on the housing 102 so that an operator can push the elongated housing 102 along a field site. The front support 106 disposed on the front side of the elongated housing 102 supports the housing 102 when not in motion. The axle 110 is configured to rotate the plurality of wheels 112 and supports the weight of the device 100. The axle 110 is steerable to move in a plurality of directions. The plurality of wheels 112 movably supports the elongated housing 102 such that said housing 102 can be moved about. In an example, the plurality of wheels 112 are compressible so as to compress in response to an impact load. For example, the plurality of wheels 112 are at least partially elastomeric. The plurality of wheels 112 are mounted to the axle 110.

The device 100 includes a mount to hold an auger 108 (along with a bucket) which is configured to collect the soil sample of the soil layer. In an example, the auger 108 is located on the front side of the elongated housing 102. The auger 108 is configured to deposit the collected soil sample into the sample holder 114 of the device 100. In an example, a soil probe or a hammer probe may be used instead of the auger 108. In an example, the bucket is made of plastic.

The sample holder 114 is configured to receive the soil sample from the auger 108. The sample holder 114 has a defined volume. In an example, the sample holder 114 has a volume of 77 $cm^3$ ($7.75 \times 10^{-5}$ $m^3$) and is able to store a 100 gm soil sample. The sample holder 114 includes a sample holder door 116, and a sample holder release lever 118. When the operator pushes the sample holder release lever 118, the sample holder door 116 is configured to release the received soil sample into the hopper 148, where it is stored in a sample bag 152 as needed.

The scale 122 is also connected to the sample holder 114. The scale 122 is configured to measure a weight of the soil sample stored within the sample holder 114, known as an undried weight of the soil sample. The heating device 120 is coupled with the sample holder 114. The heating device 120 is configured to dry the soil sample stored in the sample holder 114 for a specified time. For example, the heating device 120 is a heating coil or a heater. After a specified time of heating, the scale 122 is configured to measure a weight of the dried soil sample, known as a dried weight of the soil sample. For example, the device 100 also includes a fan 160 that is configured to exhaust the steam generated during the heating of the soil sample. In an example, the fan 160 is located in the top section 102A of the housing 102. The fan 160 is connected to the microprocessor 140, for example, through wiring or through the wireless module. The microprocessor 140 is configured to actuate the fan 160 once the heating device 120 is turned on.

The microprocessor 140 is located within the housing interior. For example, the microprocessor 140 is located in the top section 102A of housing 102. The microprocessor 140 is connected to the heating device 120, the scale 122, the spectrometer 124, the display screen 130, and the power source 132. The microprocessor 140 is configured to receive the dried weight of the soil sample, the undried weight of the soil sample from the scale 122; and spectral emission intensities of the soil sample from the spectrometer 124.

The microprocessor 140 includes a circuitry 142, and a memory 144. The circuitry 142 is configured to employ preprocessing on the received data, such as filtering and amplifying the received data.

The memory 144 is configured to store the preprocessed data and the programming instructions. The memory 144 is configured to store a database of known emission spectra (having a plurality of spectral emission intensities corresponding to a plurality of elements), a plurality of unconfined compressive strength values corresponding to the plurality of elements, at least one root mean square error (RMSE) threshold value, a plurality of resonance frequency shift values, and the like. The program instructions include a machine learning model that is configured to unconfined compressive strength of each of the collected soil samples. In an example, the machine learning model includes a machine learning regressor that is trained to predict and forecast unconfined compressive strength based on a relationship between different independent variables and an outcome (unconfined compressive strength of the soil). The program instructions further include a deep learning classifier which is trained to classify the images captured by the camera. According to the present disclosure, the deep learning classifier is a convolutional neural network (CNN). In an aspect, the memory 144 is configured to store the machine learning model and a predefined dataset for training the machine learning model. The program instructions include a program that implements a method for using machine-learning methods to determine unconfined compressive strength of the soil in accordance with embodiments of the present disclosure and may implement other embodiments described in this specification. The memory 144 is also configured to store a plurality of images, and a plurality of barcodes having identification information corresponding to each barcode. The memory 144 is further configured to store a mapping application (downloaded from a remote computer). The memory 144 may include any computer-readable medium known in the art including, for example, a volatile memory, such as a Static Random Access Memory (SRAM) and a Dynamic Random Access Memory (DRAM) and/or nonvolatile memory, such as a Read Only Memory (ROM), an erasable programmable ROM, flash memories, hard disks, optical disks, and magnetic tapes.

The microprocessor 140 is configured to fetch and execute computer-readable instructions stored in the memory 144. The microprocessor 140 is configured to execute a sequence of machine-readable instructions, which may be embodied in a program or software. The instructions can be directed to the microprocessor 140, which may subsequently program or otherwise be configured to implement the methods of the present disclosure. According to an aspect of the present disclosure, the microprocessor 140 may be implemented as one or more microprocessors, microcomputers, microcontrollers, digital signal processors, central processing units, state machines, logic circuitries, and/or any devices that manipulate signals based on operational instructions.

In an operative aspect, the microprocessor 140 receives the undried weight of the soil sample from the scale 122. Upon receiving the undried weight, the microprocessor 140 actuates the heating device 120 to dry the soil sample for the specified time. After heating the soil sample, the scale 122 measures the dried weight of the soil sample and the microprocessor 140 receives the dried weight of the soil sample from the scale 122. Under the execution of the program instructions, the microprocessor 140 is configured to calculate a bulk density of the soil sample. The bulk density of the material is calculated using the following formula: $D=M/V$, where: D is Bulk density (g/l), M is weight of the sample holder (g), and V is volume of sample holder 114. The microprocessor 140 is configured to calculate the bulk density of the soil sample by dividing the dried weight by the volume of the sample holder.

The microprocessor 140 is also configured to calculate the water content of the soil sample by subtracting the dried weight of the soil sample from the undried weight of the soil sample and dividing the difference by the weight of the dried soil sample.

The microprocessor 140 is configured to actuate the spectrometer 124 to perform laser induced breakdown spectroscopy. The spectrometer 124 is located over the sample holder 114. The spectrometer 124 is configured to perform laser induced breakdown spectroscopy (LIBS) on the soil sample. The LIBS is a rapid, portable, in situ atomic spectroscopy technique used to measure the concentration of elements in soil samples. The spectrometer 124 is used to measure the variation of a physical characteristic over a given range (spectrum). The spectrometer 124 is configured to employ a high-power laser pulse (an energy source 126) causing ablation of atoms from the sample surface and formation of a short-lived, high-temperature plasma. As the plasma cools, the excited electrons decay to lower-energy orbitals, emitting photons with wavelengths inversely proportional to the energy difference between the excited and base orbitals. The spectrometer 124 records the spectrum of emission intensities of the high energy photons. There are many possible excited states and thus many emitted wavelengths for each element. In an example, the spectrometer 124 is an infrared (IR) spectrometer, an ultraviolet-visible (UV-Vis) spectrometer, a mass spectrometer, a nuclear magnetic resonance (NMR) spectrometer and an inductively coupled plasma (ICP) spectrometer. The microprocessor 140 is configured to identify each constituent element in the soil sample by matching the spectrum of emission intensities to a database of known emission spectra fetched from the memory 144. The spectrometer 124 measures the generated spectral emission intensities (also known as LIBS spectrum) of the constituent elements of the soil sample.

Under the execution of the program instructions, the microprocessor 140 is configured to apply the spectral emission intensities, the bulk density, and the water content of each soil sample as input features to a trained machine learning regressor. In an example, the trained machine learning regressor is one of a decision tree regressor (DTR) and a support vector regressor. In an aspect, the trained machine learning regressor is combined with an adaptive boosting (ADB) classifier, therefore generating four machine models referred to as a DTR model, an SVR model, a DTR-ADB (boosted DTR) model, and an SVR-ADB (boosted SVR) model. The trained machine learning regressor combined with the adaptive boosting classifier is configured to predict the unconfined compressive strength of the soil sample.

The microprocessor 140 is operatively connected to the display screen 130 and receives information including the unconfined compressive strength, the bulk density, the water content and the spectral emission intensities of the soil sample. The display screen 130 is mounted on an exterior surface of the housing 102. The display screen 130 is configured to display the unconfined compressive strength, the bulk density, the water content and the spectral emission intensities of the soil sample. In an example, the display screen 130 is a LED matrix, small video display, a high-resolution liquid crystal display (LCD), a plasma screen, light-emitting diode (LED), or other devices suitable for displaying the information.

In an aspect, the device 100 includes a camera 150 that is configured to capture pictures and/or video of the soil samples, collected by the auger 108. The camera 150 is configured to capture the video and/or pictures of the environment surrounding the device 100 to provide context to the geometric location from which the soil sample is taken. In an example, the camera 150 is located on the exterior side of the housing 102. The camera 150 is connected to the microprocessor 140 through wiring or through a wireless module. The microprocessor 140 is configured to actuate the camera 150 to capture the videos and receive the videos from the camera 150. The camera 150 may be, for example, a high-resolution digital camera, an image capturing sensor, an infrared (IR) camera, a visible light camera, an intensified charge-coupled device (ICCD) camera, an image intensified camera, a sensor fused camera, and the like. A video file is made up of a series of still images. Every individual of these still images is called a frame. In aspects of the present disclosure, image frames are extracted from the videos and combined with the barcode of the soil sample stored in the database. The image frames can also be displayed with the location of the soil sample on the map.

The power source 132 is configured to supply power to one or more components of the device 100. The power source 132 is switchably connected by wiring to the microprocessor 140. The microprocessor 140 is configured to determine an estimated power requirement of the device 100 during a time period. The microprocessor 140 is configured to determine a charge state of the power source 132, and to produce an indication of the remaining use time of the device 100 based on the estimated power requirement and the charge state of the power source 132. The power source 132 includes a solar power supply, a battery, and an AC power source. The solar power supply is configured to convert solar energy into electrical energy. In an example, the solar power supply may be a secondary power source. The AC power input is configured to receive an AC input current at a specified AC input voltage level. In an example, the AC power input may be a primary power source which is used to charge the battery at a remote office location. The battery may also be recharged from a DC power source, such as a vehicle battery. The battery is configured to recharge using the solar power supply, the AC power source or the DC power source. The battery is configured to recharge using a charging port 134. In an example, the battery is selected from the group consisting of non-aqueous lithium-ion battery, polymer lithium-ion battery and sodium sulfate battery.

The device 100 further includes a global positioning system (GPS) receiver 146, a communications device 136, and a near field antenna 138. The GPS receiver 146 is located in the housing 102 of the device 100. The GPS receiver 146 includes antennas that use a satellite-based navigation system with a network of satellites in orbit around the Earth to provide position, velocity, and timing information. GPS is a satellite-based navigation system that provides geolocation and time information to the GPS receiver 146 anywhere on or near the Earth where there is an unobstructed line of sight to four or more GPS satellites. The microprocessor 140 is operably connected to the GPS receiver 146 to receive the current location coordinates of the device 100, representing the location from which the soil sample is collected. The microprocessor 140 is configured to record the location from which the soil sample is collected. In an aspect, the recorded location is stored corresponding to a unique barcode assigned to a barcoded bag 152.

The communications device 136 is operatively connected to the microprocessor 140 and receives data from the microprocessor 140. The communications device 136 is configured to generate a communication packet. For example, the communication packet includes the GPS location of the collected soil sample, the unconfined compressive strength, the bulk density, the water content, and the spectral emission intensities of each soil sample. The communications device 136 has at least one antenna for transmitting and receiving communications packets or records to/from the remote computer. In some examples, at least one antenna is a near field antenna 138, a WiFi antenna, and a radio frequency antenna. The near field antenna 138 is operatively connected to the communications device 136. The communications device 136 is wirelessly connected by near field communications to a smart device or the remote computer. The communications device 136 may include a wireless-frequency transceiver having a variable gain amplifier that generates radio-frequency signals for transmission. A wireless amplifier circuit may be used to amplify the radio-frequency signals at the output of the variable gain amplifier for transmission through a plurality of antennas.

As shown in FIG. 1B, the device 100 includes a barcoded bag holder 154 and a barcode scanner 156. The barcoded bag holder 154 is configured to hold the plurality of barcoded bags 152. The barcode scanner 156 is configured to scan the barcoded bag 152 and is able to retrieve information corresponding to the bag 152 stored in the database (memory). The barcode scanner 156 is coupled to the display screen 130 and is able to display the retrieved information on the display screen 130. The barcode scanner 156 is able to distinguish the barcoded bags 152 with effectiveness. In an example, the barcoded bag 152 may have an RFID tag, a barcode tag, or a QR code printed on a tag attached to the barcoded bag.

In an aspect, the device 100 also includes a thermometer 166 configured to measure temperature of the collected soil sample.

In an aspect, the device 100 includes a speedometer 162 and a compass 164 which are configured to record distance and direction of the device 100 to estimate location when a location service, such as GPS, is not available.

The device 100 is configured to determine the unconfined compressive strength of the soil samples based on the elemental intensities of the constituent elements present in the soil sample as well as the rest of the physical properties (bulk density and moisture content), thereby yielding a more accurate result.

Figure 1C:
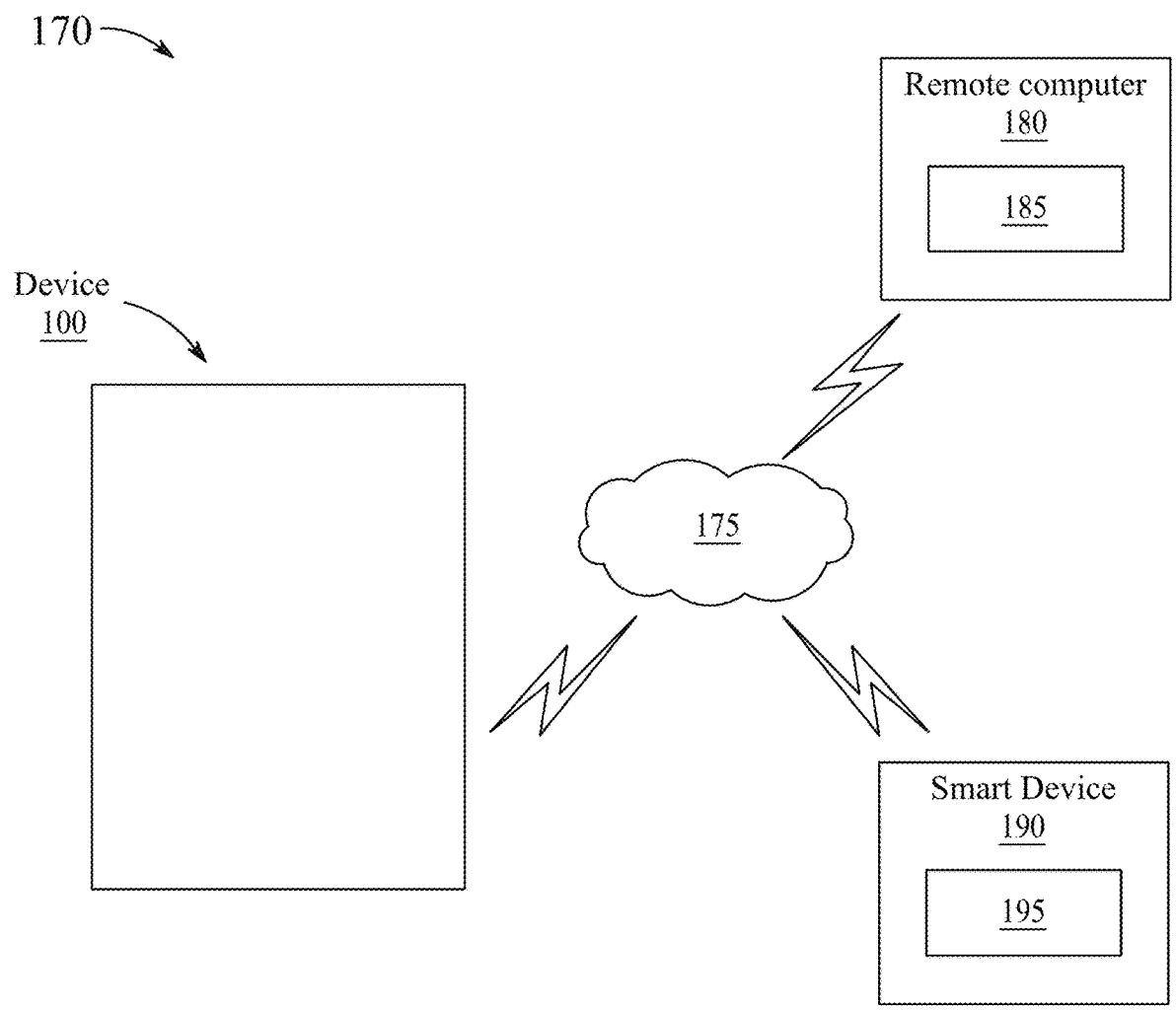
FIG. 1C represents a network diagram of communications of the device with a smart device and a remote computer, according to aspects of the present disclosure.

FIG. 1C represents a network diagram 170 of the device 100. As shown in FIG. 1C, the device 100 is configured to communicate with at least one smart device 190, and/or a remote computer 180 over a data communication network 175. The device 100 and the smart device 190 may have communications capabilities that include, but are not limited to, GPS, Bluetooth Low Energy (BLE), Wi-Fi, EDGE, 2G, 3G, 4G, LTE, wired network, Bluetooth®, Near Field Communications (NFC), Infrared (IR), etc.).

The communications device 136 of the device 100 is configured to transmit the communication packet to the remote computer 180 and the smart device 190. The smart device 190 is configured to receive the communication packet from the device 100 (soil application running on the device 100). A computer mapping application 195 is stored on the smart device 190. The computer mapping application 195 is set up to generate a map based on the extracted information, such as the current location of the device 100, and UCS of the soil along with various properties (location of each soil sample, site images, the bulk density, the water content and the spectral emission intensities). For example, the computer mapping application 195 includes a barcode scanning page for displaying the information associated with the barcode. In an aspect, the computer mapping application 195 is configured to exchange data with a mapping application 185 installed on the remote computer 180. For example, and without limitation, the smart device 190 may refer to a mobile device, Personal Digital Assistant (PDA), desktop computer, Global Positioning System (GPS) device, automotive navigation system, wearable object, smartwatch, wearable sensor, a cellular telephone, a tablet, a netbook, a wireless terminal, a laptop computer, a wearable computer device, customized travel device or any other device. The device 100 is capable of communicating and synchronizing the recorded activities with the application running on the smart device 190.

The remote computer 180 (also referred as "a server") includes the mapping application 185 which is configured to receive the communication packet from the device 100 (soil application running on the device 100). The remote computer 180 extracts the information from the received communication packet and displays the location of each soil sample with the prediction of the unconfined compressive strength, a current location of device, the bulk density, the water content and the spectral emission intensities on a screen of the remote computer 180.

In some examples, the computer mapping application 195 or the mapping application 185 may be a software or a mobile application from an application distribution platform. Examples of application distribution platforms include the App Store for iOS provided by Apple, Inc., Play Store for Android OS provided by Google Inc., and such application distribution platforms.

For example, a geologist or any geo-professional, handling the remote computer 180, may be able to analyze the results received using the mapping application 185. Based on the analysis, the geologist may ask the operator (having the smart device 190) to go a specific place and perform the soil testing. For example, a message may be displayed on the smart device 190 showing as "Please test the area between (certain coordinates) to pinpoint the subsurface compressibility". Also, the operator performing the testing, is able to get instructions from the geologist.

In an operative aspect, the remote computer 180 is connected to a plurality of devices 100. Each of the plurality of devices 100 has a unique device identification number. During setting up the device 100, a profile is created in the remote computer 180. The profile is configured to store the unique device identification number and location of the device 100. In an aspect, the remote computer 180 is configured to update the profile of each device based on the received communication packets from each device. In an aspect, the remote computer may store image frames of the site from which the soil sample was taken and display the image frames on the map or on a display screen of the remote computer. Therefore, the remote computer 180 is able to analyze the behavior of the soil of a large geographic area based on the received data from the plurality of devices.

In an aspect, the remote computer 180 is an application server. In some examples, the remote computer 180 is a server operating system, such as Windows Server or Linux, which acts as the platform that enables applications to run. In an example, the remote computer 180 can be implemented as one or more microprocessors, microcomputers, microcontrollers, digital signal processors, state machines, logic circuitries, and/or any devices that manipulate signals based on operational instructions. Among other capabilities, the remote computer 180 is configured to fetch and execute the pre-determined set of instructions stored in a memory. In some examples, the remote computer 180 may be implemented as any type of computing device for hosting a webpage or website accessible via the network, such as, but without limitation, a web server, application server, cloud server, or other host. For example, the remote computer 180 acts as a management server that is capable of performing data communication with respect to the device(s). The management server provides access to the hardware resources that are required for establishing network connectivity.

Figure 2:
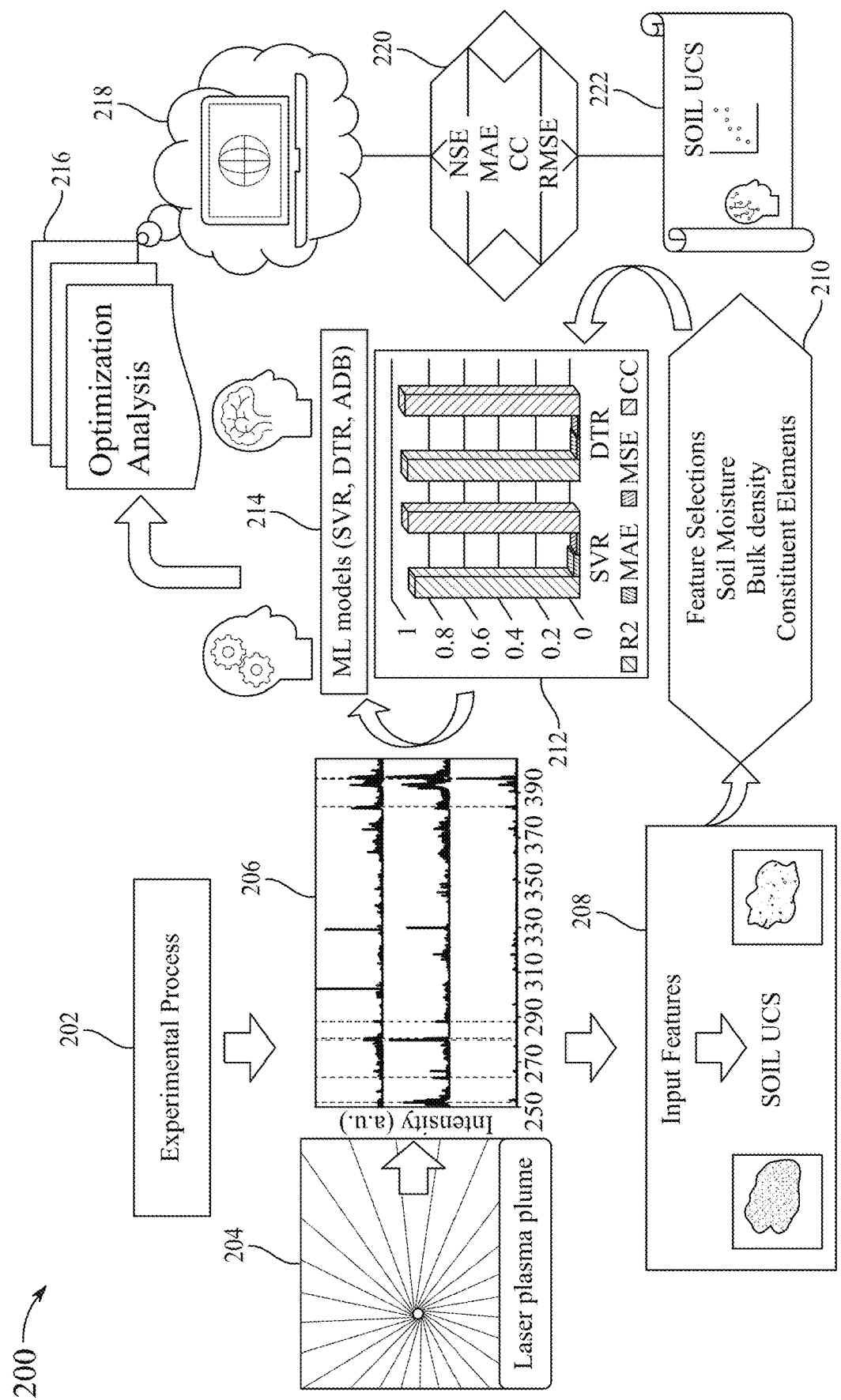
FIG. 2 illustrates a schematic process flow of the field portable device, according to certain embodiments of the present disclosure.

FIG. 2 illustrates a schematic process flow 200 of the device 100. The device 100 is configured to survey a geographic area to determine the unconfined compressive strength of a soil layer of the geographic area.

Step 202 includes initialization of an experimental process. In an example, the experimental process includes transporting the device 100 to the geographic area. The soil sample of the soil layer is collected with the auger 108. The auger 108 deposits the soil sample into the sample holder 114 of the device 100. The scale 122, connected to the sample holder 114, records the undried weight of the soil sample. The heating device 120 dries the soil sample for a specified time. The scale 122 records a dried weight of the soil sample. The GPS receiver 146 records the location of the soil sample. In an example, the device 100 is configured to collect a set of soil samples by moving around the geographic area. In an aspect, the device 100 is operated manually by the operator or may be operated remotely. In an example, the device 100 is configured to use a plurality of barcoded soil bags 152, located in the hopper 148, for storing each soil sample of the set of soil samples. For example, each soil sample is stored in a unique barcoded soil bag 152. The device 100 is configured to store a plurality of information related to each unique bar coded soil bag such that the operator is able to distinguish the soil bags and retrieve the information stored corresponding to the selected bag. In an example, the plurality of information includes location of the soil sample from where the soil was collected, composition of the soil sample, the undried weight of the soil sample, bulk density of the soil sample, images of the environment surrounding the test site and the like.

Step 204 includes directing, by the laser 126, high-energy laser pulses onto an outer surface of the soil sample until a portion of the soil sample is ablated and forms a plasma. The plasma is cooled down to release high energy photons.

Step 206 includes performing laser induced breakdown spectroscopy (LIBS) on each soil sample of the set of soil samples to generate the spectral emission intensities of the soil sample respectively. The spectrometer 124 records a spectrum of emission intensities of the high energy photons corresponding to each soil sample. In an example, the spectrometer 124 is configured to store the recorded spectrum of emission intensities of each soil sample in the database.

Step 208 includes applying spectral emission intensities of the soil sample to the machine learning model. The microprocessor 140 is connected to the scale 122, the spectrometer 124 and the GPS receiver 146 to receive the undried weight, the dried weight, the spectral emission intensities and the location of the soil sample, respectively, and calculates the bulk density and the water content of the soil sample. The microprocessor 140 is configured to input various physical parameters (color, texture, structure, porosity, consistency, aggregate stability, temperature, cation exchange capacity (CEC), bulk density, soil structure, water infiltration rate, rooting depth, and the water content) of the soil sample to the machine learning model.

Step 210 includes selecting features from the received data for the machine learning model. The machine learning model requires input features that are relevant and important to predict the outcome. However, not all features are equally important for a prediction task, and some features might even introduce noise in the model. To overcome such issues, feature selection and feature extraction are employed. Feature selection is a process of selecting a subset of relevant features from the original set of features. The goal is to reduce the dimensionality of the feature space, simplify the model, and improve its generalization performance. Feature extraction is a process of transforming the original features into a new set of features that are more informative and compact. In an aspect, the selected features (input features) include the spectral emission intensities, the bulk density, and the water content of each soil sample.

Step 212 includes the training step of calculating various mathematical parameters associated with the employed machine learning model. In an example, the machine learning model includes the DTR, the SVR, and the adaptive boosting classifier. For the field device 100, the DTR with the adaptive boosting classifier was selected as the trained machine learning model, as this model gave the best experimental results.

Step 214 includes applying various machine learning models on the data received from the spectrometer 124 and the microprocessor 140. Step 214 further includes comparing the performance of each of the machine learning models.

Step 216 includes applying an optimization analysis to the applied machine learning models. For example, the optimization analysis involves analyzing the performance metrics of each model, identifying areas for improvement, and testing different optimization techniques to enhance the accuracy and efficiency of the model. In an example, the optimization techniques include hyperparameter tuning, regularization, and model pruning. During optimization, the model is trained iteratively which results in a maximum and minimum function evaluation. The result in every iteration is compared by changing the hyperparameters in each step until defined results are obtained. In an aspect, after optimization analysis, the DTR is combined with the adaptive boosting classifier, and the SVR is combined with the adaptive boosting classifier. Step 216 further includes predicting, by the trained DTR combined with the adaptive boosting classifier, the unconfined compressive strength of the soil sample.

Step 218 includes communicating the predicted unconfined compressive strength to the smart device 190 or the remote computer 180 over the network 175.

Step 220 includes performing statistical analysis, by the smart device 190, on the received data. In an aspect, various statistical techniques such as regression, classification, and clustering are used to analyze the received data and generate predictions. In the machine learning, statistical analysis is used to identify patterns and relationships in data, which can then be used to train models and make more accurate predictions.

Step 222 includes displaying the unconfined compressive strength, the bulk density, the water content and the spectral emission intensities of the soil sample on the display screen 130 operatively connected with the microprocessor 140. Step 222 further includes displaying the statistical data, the unconfined compressive strength of the soil sample and the location of the soil sample on a map on the display screen 130 of the smart device 190.

In an operative aspect, step 214 includes training the DTR model and the SVR model according to their mathematical framework. In an example, the machine learning model was trained under a python computing environment using a Sci-Kit learn (Sklearn) library. The Scikit-learn library is an open source library in Python for machine learning tasks, including classification, regression, clustering, and more. The Scikit-learn library was developed by the French National Institute for Research in Computer Science and Automation (INRIA). The Scikit-learn library was used that provides a wide range of algorithms, including support vector machines, decision trees, and neural networks, as well as tools for model selection, data preprocessing, and visualization.

In an operative aspect, the DTR is a representation of data in a tree-structured form that is largely utilized to solve machine learning problems for regression and classification. The tree includes branches, leaves, and multiple internal nodes based on the available dataset. Existing classes are used to divide occurrences and features by the DTR equally.

The given occurrences are created by stimulating the decision tree (DT), and when the fitness function is minimized, the optimal decision tree is produced. Parameters such as the feature number, split sample, leaf sample, fitness function, number of features, and tree depth influence the accuracy of the DTR. The number of required present at a leaf node is referred to as a leaf sample. The lowest number of needed samples to split an internal node is depicted by the split sample. The depth of the tree is described by how deep it can go; as the depth increases, the tree acquires information on the data. While the error between the experimental and predicted results is reduced by the fitness error. In experiments, a number of known input features (bulk density, soil moisture, Si, Fe, Mg, Ca, Na, Al, Zn, In, Ti, O, and K) was considered which may be represented by ($X_1$, $X_2$, . . . , $X_n$) respectively. The DTR model is trained on a dataset of soil samples, where the unconfined compressive strength is known for each sample. During training, the DTR model learns to map the input features to the corresponding unconfined compressive strength value. When a new soil sample is presented to the trained DTR model, the input features are fed into the DTR model, and the DTR model outputs an estimated unconfined compressive strength value.

The brief mathematical representation of the DTR is presented below:

Let $X=X_1, X_2, \ldots, X_n$ represent the predictors (input variables), and let $Y=Y_1, Y_2, \ldots, Y_n$ represent the continuous values of the target, where n is the number of observations, t is a threshold, and f is a feature variable.

Let m and $\alpha=(f, t_m)$ be respectively a node and candidate split.

$$P_l(\alpha) = (x, y) | x_f \leq t_m \quad (1)$$

$$P_r(\alpha) = (x, y) | x_f > t_m \quad (2)$$

Equations (1)-(2) denote the two sides of the tree. By way of explanation, the two equations can be rewritten as:

$$P_r(\alpha) = \frac{P}{P_l(\alpha)}, \quad (3)$$

where n is the number of the sample at the current node and $Y_t$ is the mean predicted value at terminal nodes, $$\overline{Y}_m = \frac{1}{n}\sum_{i \in n} Y_i. \quad (4)$$

The mean predicted value in equation (4) is subsequently applied to equations (5)-(7), showing the mean square error, mean absolute error and $R^2$, respectively.

$$S(X_m) = \frac{1}{N}\sum_{i=1}^{N}(Y_i - \overline{Y}_m)^2, \quad (5)$$

$$S(X_m) = \frac{1}{N}\sum_{i=1}^{N}|Y_i - \overline{Y}_m|, \quad (6)$$

$$S(X_m) = 1 - \frac{\frac{1}{N}\sum_{i=1}^{N}(Y_i - \overline{Y}_m)^2}{\frac{1}{N}\sum_{i=1}^{N}(Y_i - \hat{Y}_m)^2}, \quad (7)$$

Equations (5)-(7) are utilized as fitness functions to reach the fitness criteria in the prediction accuracy. The depth of the DT continues to increase until the desired accuracy is achieved based on the assigned fitness criteria.

In an operative aspect, the SVR is used in modeling and prediction in a continuous space that depends on the projected pattern between the target variable and the descriptors. SVR separates the data class by utilizing the e-insensitive loss function to influence the hyperplane, which ignores the difference between the predicted values from the actual values at a certain distance. The SVR constructs a hyperplane that optimizes the margin and decreases the error. SVR can make predictions based on a small training set, making it attractive and computationally less expensive. Support vector machine (SVM) and SVR utilize the same principle of Vapnik's support vectors. Vapnik's support vectors are influential examples in a classification or regression model. These vectors are the instances that maximize the margin between the classes, or the mean squared error. However, the SVR does not use the regular empirical risk minimization of artificial neural networks but rather the basics of structural risk minimization. The SVM is used as a classification tool, and its margin of tolerance $\varepsilon$ is not explicit but rather extracted from the problem.

In SVR, the input features are mapped out into high-dimensional feature space using a non-linear transformation function, making it possible to rightly apply a linear regression function in the new feature space. An insensitive loss function that has the property $\varepsilon>0$ is considered when applying the SVR algorithm. Also, errors below $\varepsilon$ are not taken into consideration by the model. A brief mathematical description of the model is given below:

$$|(k_r - f(X_i)|_\varepsilon = \max(0, |(k_r - f(X_i)|_\varepsilon - \varepsilon) \quad (8)$$

The SVR model chooses a function that can precisely make a correct prediction with accuracy $\varepsilon$ and places the accepted difference between the predicted variable from the actual one. The linear model in equation (9) is estimated using a radial basis kernel mapping function that is non-linear by mapping the input features onto an n-dimension feature space.

$$g(x) = \tilde{\omega}\varphi(x) + C, \quad (9)$$

where c is the bias, $R^N$ is where the input dataset is contained, and $\tilde{\omega}$ is the weight factor. Based on the training data $\{x_i, k_{ei}\}$, i=1, 2, 3 ... n; $b \in R$ and $\tilde{\omega}$, $\varphi \in R^N$. The regularized risk function in equation (10) is minimized to accomplish a small testing error.

$$\frac{1}{2}\|\tilde{\omega}\|^2 + C.R_{emp}(f). \quad (10)$$

The empirical risk factor is presented in equation (11). Meanwhile, the intricacy of the model is driven by $\|\omega\|^2$ $$R_{emp}(f) = \frac{1}{n}\sum_{i=1}^{n}|(k_e - f(X_i)|_\varepsilon, \quad (11)$$

Subsequently, the optimization problem turns into:

$$\theta(\tilde{\omega}, \xi, \tilde{\xi}) = \frac{1}{2}\|\tilde{\omega}\|^2 + C\sum_{i=1}^{n}(\xi_i + \tilde{\xi}_i).$$

Subject to $$\begin{cases} k_e - (\tilde{\omega}\varphi(x) + C) \leq \varepsilon + \xi \\ \tilde{\omega}\varphi(x) + C - k_r \leq \varepsilon + \tilde{\xi} \\ \xi, \tilde{\xi} \geq 0, i = 1, \ldots n \end{cases} \quad (13)$$

where C is the regularization factor that accommodates the trade-off between the model's complexity and the accuracy of the testing and training data.

$$\sum_{i=1}^{n}(k - \tilde{k}) = 0. \quad (14)$$

The subsequent application of a Lagrangian multiplier in equation (12) transformed the dual optimization problem as presented below:

Minimize $$\theta(k, \tilde{k}) = -\frac{1}{2}\sum_{i,j=1}^{n}(k_i - \tilde{k}_i)(k_j - \tilde{k}_j)K(x_i, x_j) - \varepsilon\sum_{i=1}^{n}(k_i + \tilde{k}_i) + \sum_{i=1}^{n}k_r(k_i - \tilde{k}_i) = 0, \quad (15)$$

Subject to $$\begin{cases} \sum_{i=1}^{n}(k - \tilde{k}) = 0 \\ k_i, \tilde{k}_i, k_j, \tilde{k}_j \in [0, C] \end{cases}, \quad (16)$$

where k and $\tilde{k}$ represent the dual decision variables and $K(x_i, x_j) = \sum_i^n \varphi(x_i)\varphi(x_j)$ is the definition of kernel function, which guides the non-linear pattern between $k_e$ and x.

Solving the optimization problem in equation (15) yields the dual n-vectors k, $\tilde{k}$ that degenerates to the non-linear model in equation (17):

$$g(x) = \sum_{i=1}^{n}(k - \tilde{k})K(x, x_i) + C, \quad (17)$$

The kernel function $K(x, x_i)$ can be any one of the following:

For polynomial: $K(x, x_i) = (x_i^T x)^d$; of degree $d$. (18)

For RBF: $K(x, x_i) = \exp(-\delta.\|x - x_i\|^d)$. (19)

In SVR model, the input features are mapped out into a high dimensional feature space using a nonlinear transformation function, making it possible to rightly apply a linear regression function in the new feature space. An insensitive loss function that has the property ε>0 is considered when applying the support vector regression algorithm, and also, errors below ε are not taken into consideration by the SVR model.

In an operative aspect, the adaptive boosting technique (also known as Adaboost) is used for its high prediction efficiency. Adaptive boosting can be applied to both classification and regression problems. It is a technique of combining set of weak learners into a strong learner. A weak learner is a classifier whose performance is poor (accuracy is slightly better than a random guess). In contrast, a strong learner is a classifier with arbitrarily high accuracy. In adaptive boosting, the algorithm starts the training by first fitting the weak classifier on original dataset producing an output hypothesis and then iteratively reweighting the misclassified data to fit the next weak classifier. Each weak learner is assigned a coefficient such that the sum of the training error of the resulting boosted classifier is minimized.

Iteratively learning weak classifiers are weighted in a way that is related to the weak learner's performance and adding them to the final strong classifier. After a weak learner is added, the input data weights are adjusted, known as "re-weighting". Re-weighting means the input data that is misclassified would gain more weight and the correctly classified data would lose weight. Thus, the next weak learners focus more on the data that previous weak learner misclassified. Below is the mathematical descriptions of the training the adaptive boosting classifier:

Let equation (20) represent a general problem within a training dataset:

$$\Omega = \{(X_1, Y_1), (X_2, Y_2), \ldots ; (X_m, Y_m)\}, \quad (20)$$

where $X_i$ and $Y_i$ respectively represent the input data vectors and output value; the total number of the samples and the $i^{th}$ sample in the training dataset is denoted by m and $(X_i, Y_i)$ (I=1, . . . ; m), respectively. Subsequently, the regression tool is applied to train a weak learner (base learner) G(X) using the accepted base learning algorithm, thereby approximating the relative estimation error using equation 21. L( ) is a loss function that cannot be a linear, exponential, or square loss function.

$$e_i = L(Y_i, G(X_i)). \quad (21)$$

A single base learner may not perform well enough to achieve the requisite prediction efficiency. Adaptive boosting develops a framework where a series of weak learners may be joined to generate a powerful ensemble learner H (x) by utilizing some tactics. A regression problem's combination strategy is given as:

$$H(X) = v\sum_{1}^{N}\left(\ln\left(\frac{1}{\delta_k}\right)\right)g(X), \quad (22)$$

where k=1, 2, . . . , N; v∈(0,1)] is the regularization parameter, $\delta_k$ is the allocated weight of the base learner $G(X_i)$, and g(X) is the median of all the $\delta_k\delta G_k(X)$.

The adaptive boosting approach is a reliable method that offers a framework for combining a variety of base learning algorithms to accurately forecast the goal quantity. Support vector machines, decision trees, linear regression, and artificial neural networks are some well-known base learning methods. In summary, adaptive boosting includes four key steps: (1) data collection, (2) creation of strong learners from base learners, (3) testing and validation of the boosted algorithms, and (4) application of the strong learners to real-world issues. The main levels involved in the boosting process are the integration of the weak learners into the strong learners and the instruction of the weak learners using the training data. The base learner parameters are main adaptive boosting parameters. The adaptive boosting approach considers the number of estimators and the learning rate.

Figure 3:
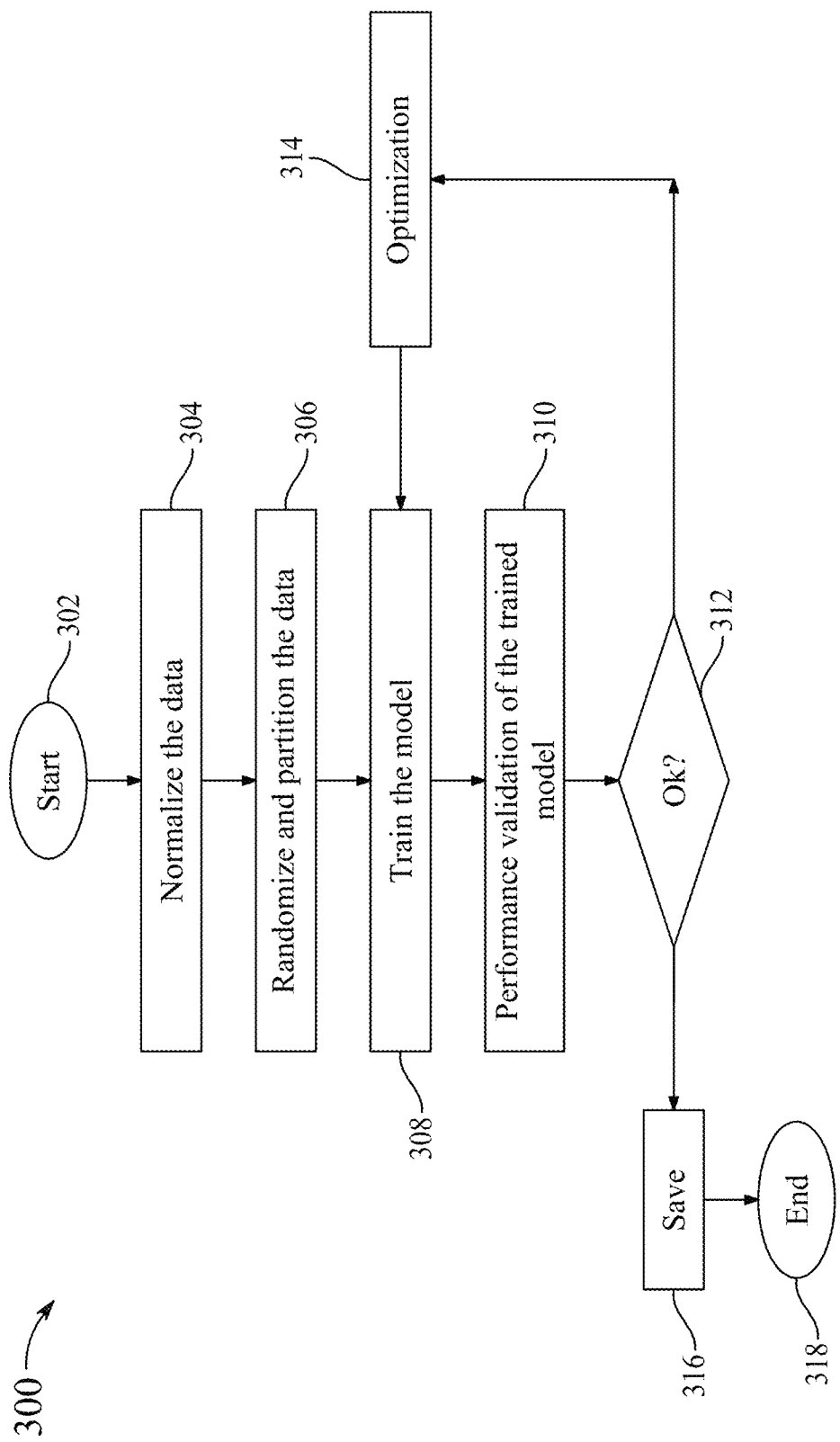
FIG. 3 represents an exemplary flow chart of training a machine learning model, according to aspects of the present disclosure.

FIG. 3 represents an exemplary flow chart 300 of training the machine learning model.

Step 302 includes initialization of the machine learning model.

Step 304 includes normalizing the data. Data normalization is applied to change the values of numeric columns in the dataset to a common scale, without distorting differences in the ranges of values. Data normalization is required only when the features have different ranges. Data normalization includes but are not limited to carry out correlation analysis and discretization dimension-reduction treatment to data. In an example, the methods of data normalization include, but are not limited to, Z-Score normalization, maximum and minimum normalization, min-max scaling, standardization, log transformation, and decimal scaling.

Step 306 includes data partition and data randomization. Data partitioning is a technique used in machine learning to divide the dataset into smaller subsets (folds), for training and testing purposes. In an example, the data is divided into two sets: a training data and a testing data. In the training phase, the machine learning regressor is trained on the training data (80% of the dataset of soil samples) having known bulk densities, known water contents, known spectral emission intensities of the constituent elements and known unconfined compressive strengths. In an example, the trained machine learning regressor is a decision tree regressor which maps the spectral emission intensities, the bulk density and the water content of each soil sample to the unconfined compressive strength of the soil sample. In the testing phase, the machine learning regressor is tested on the testing data (20% of the dataset of soil samples).

Data randomization is a process of introducing randomness or noise into the training data, which can help to prevent overfitting and improve model generalization.

Step 308 includes training the model. In an example, the machine learning regressor (DTR) combined with the adaptive boosting classifier was trained during the training phase. During the training phase, a depth of the DTR is selected. The input features (spectral emission intensities, the bulk density and the water content of each soil sample of the dataset) are applied to the DTR model. An equal weight is assigned to each of the spectral emission intensities, the bulk density and the water content to the DTR model. The DTR model generates a first prediction of the unconfined compressive strength of the soil sample for the first depth and calculates a first root mean square error (RMSE) between the first prediction of the unconfined compressive strength and the known unconfined compressive strength (fetched from the memory 144). The DTR model compares the first RMSE to a threshold value. When the first RMSE is less than the threshold value, the DTR model is configured to output the first prediction as the unconfined compressive strength. When the first RMSE is greater than the threshold value, the DTR model saves the weights of the first prediction, the unconfined compressive strength of the first prediction and the first RMSE. During the training phase, adaptive boosting is performed by identifying input features which are misclassified in the first prediction of the unconfined compressive strength and modifying the weights of the input features by increasing the weights of the weakly correlated input features. Then the input features with the modified weights are again applied to the DTR model. The DTR model generates a second prediction of the unconfined compressive strength of the soil sample and calculates a second RMSE using the second prediction of the unconfined compressive strength and the known unconfined compressive strength. The DTR model is configured to compare the second RMSE to the first RMSE. When the second RMSE is less than the first RMSE, the DTR model compares the second RMSE to the threshold value. If the second RMSE is less than the threshold value, the DTR model outputs the second prediction as the unconfined compressive strength and stops incrementing. If the second RMSE is greater than the threshold value, then the DTR model is configured to save the modified weights of the second prediction, the unconfined compressive strength of the second prediction and the second RMSE. Adaptive boosting is performed by continuing identifying input features which are misclassified, increasing the weights of the misclassified input features, applying the reweighted input features to the decision tree classifier, and outputting predictions of the unconfined compressive strength until the RMSE is less than the threshold value. When the RMSE is less than the threshold value, the DTR model is configured to average the weights and predictions of unconfined compressive weight of each iteration and output the average of the predictions as the unconfined compressive strength.

Step 310 includes performance validation of the trained model (boosted DTR model). The performance validation of the trained model involves evaluating its ability to generalize to new, unseen data and make accurate predictions. The performance validation is done through various metrics such as accuracy, precision, recall, and F1 score. For example, the performance validation is done by separating the data set into the training dataset and a validating dataset; and then evaluating the performance of the model on the validation dataset.

To ensure that the boosted DTR model was not overfitting, 10-fold cross validation was used to optimize the hyperparameters of the model. In 10-fold cross-validation, the data was divided into 10 parts, and each part was used as a test set, while the remaining nine parts were used as training sets. This process was repeated 10 times, with each part was used as the test set once. The GridSearchCV function from scikit-learn was used to search for the optimal hyperparameters. GridSearchCV tests all possible combinations of hyperparameters and selects the one that gives the best performance. Different combinations of hyperparameters, such as the number of estimators, the learning rate, and the maximum depth of the decision trees, have been tested.

To select the optimal descriptors to estimate the soil unconfined compressive strength, the statistical analysis of the dataset was used. The correlation between the elemental intensities and the soil unconfined compressive strength was analyzed using a correlation matrix depicted by a heat map.

Step 312 includes checking whether performance of the trained model during step 310 is in line with an expected prediction efficiency or not.

If the performance of the trained model is less than the expected prediction efficiency, then flow moves to step 314 that includes optimization of the trained model. Step 308-step 314 are performed till the trained model starts performing according to the expected results.

If the performance of the trained model is in line with the expected prediction efficiency, then the process moves to step 316 that includes saving the trained model.

Step 318 includes end of the training the machine learning model.

The following experiments were conducted on the device 100 to verify its operation.

First Experiment: Statistical Analysis of the Utilized Dataset

The first experiment was conducted to explore the validation of the selected descriptors to predict the UCS. During the experiments, the hyperparameters of the model were selected and optimized.

The data used in the present disclosure can be categorized into two parts: physical features and chemical features. In an example, the chemical features (elemental intensities of the constituent elements) were obtained from the spectrometer 124, while the physical features were measured in the laboratory during the training phase.

Figure 4:
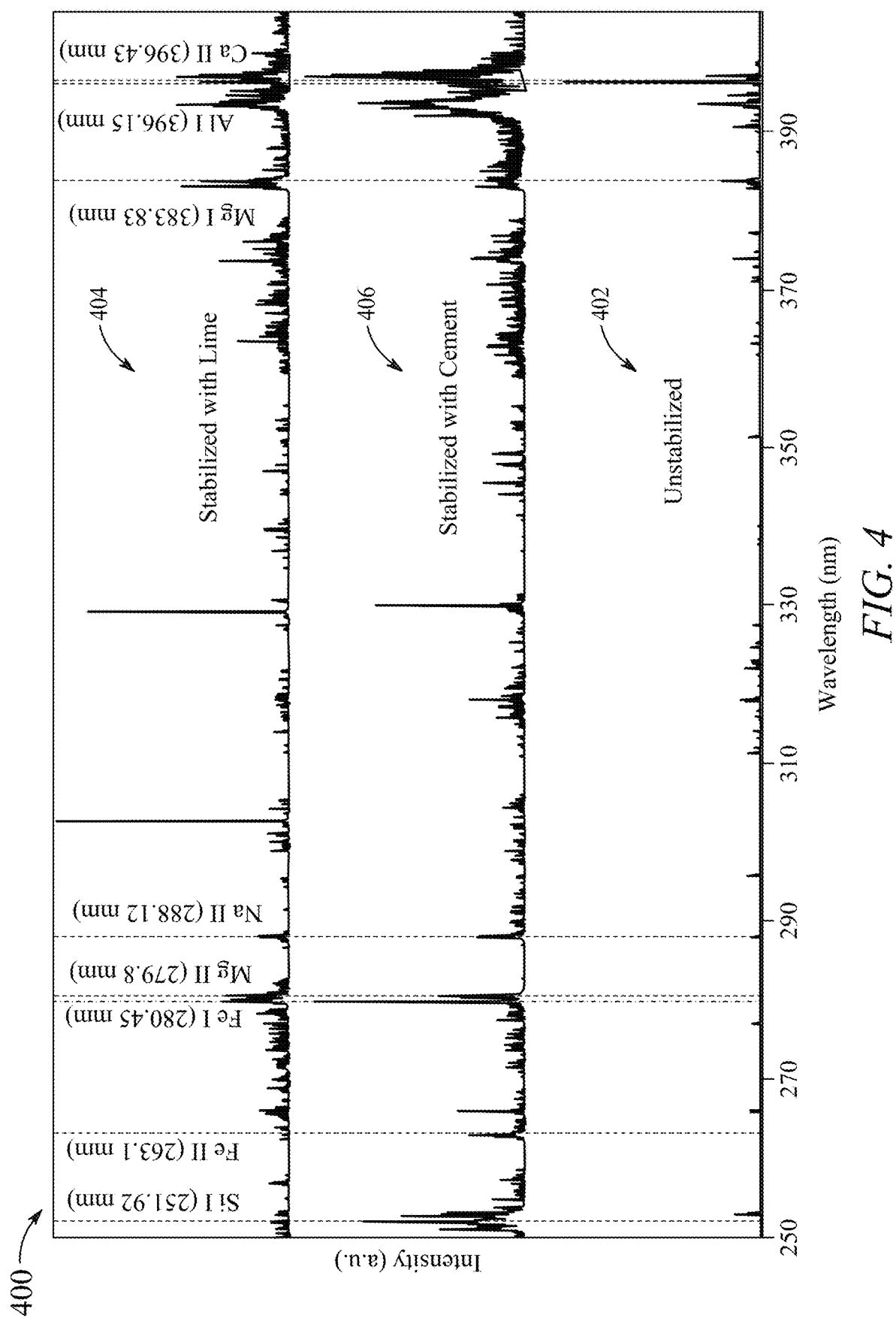
FIG. 4 illustrates a graphical representation of a laser-induced breakdown spectroscopy (LIBS) spectra, according to aspects of the present disclosure.

FIG. 4 illustrates a graphical representation 400 of the LIBS spectra. The LIBS spectra illustrates the elemental intensities of the constituent elements within a given wavelength range for stabilized soil samples, and unstabilized soil samples. Section 402 represents the LIBS spectra for elements present in the unstabilized soil samples within certain wavelengths. Section 404 represents the LIBS spectra for elements present in the stabilized soil samples (stabilized with lime) within certain wavelengths. Section 404 represents the LIBS spectra for elements present in the stabilized soil samples (stabilized with cement) within certain wavelengths. The dataset shows the persistent lines of Si, Fe, Mg, Ca, Na, Al, Zn, In, Ti, O, and K, as well as two physical features, i.e., the water content of the soil sample and the bulk density. To ensure generalization of the machine learning model, different soil samples were collected from multiple locations and were considered during an input data processing phase. The statistical description of the data is presented in Table 1a and Table 1b. For example, a total of 450 data points were used to build the models employed in the present disclosure.

Figure 5A:
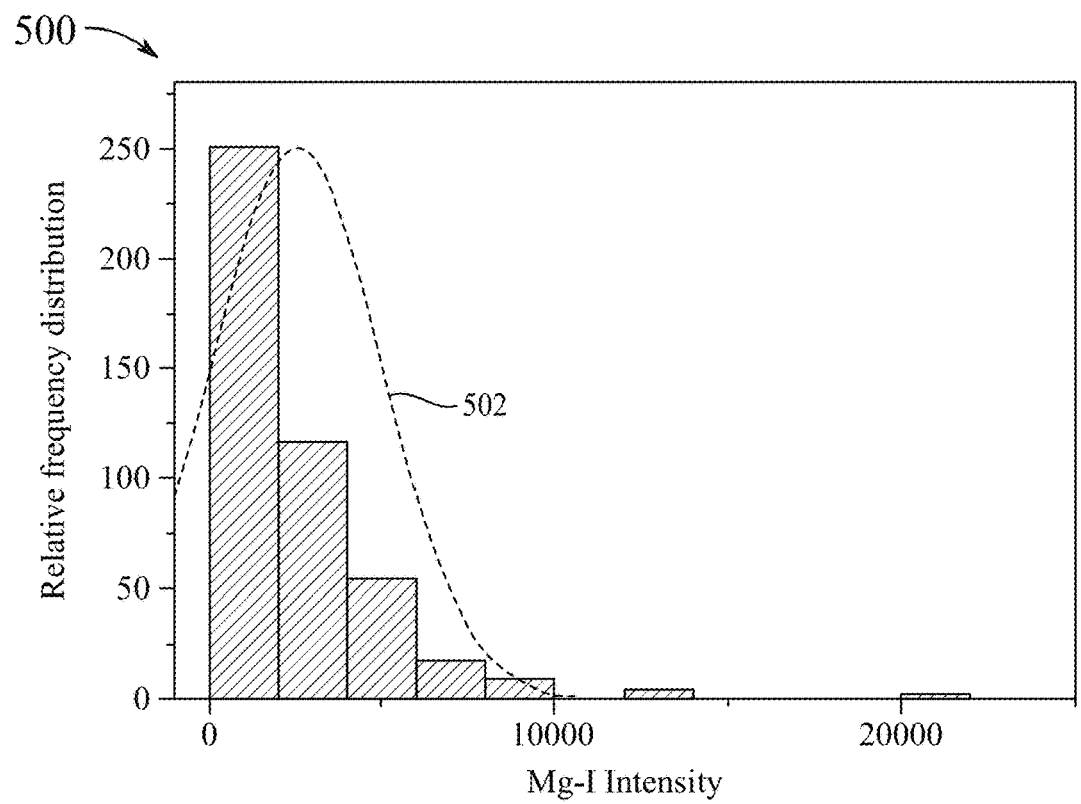
FIG. 5A is a histogram representing correlation between a relative frequency distribution and magnesium emission intensity, according to aspects of the present disclosure.
Figure 5B:
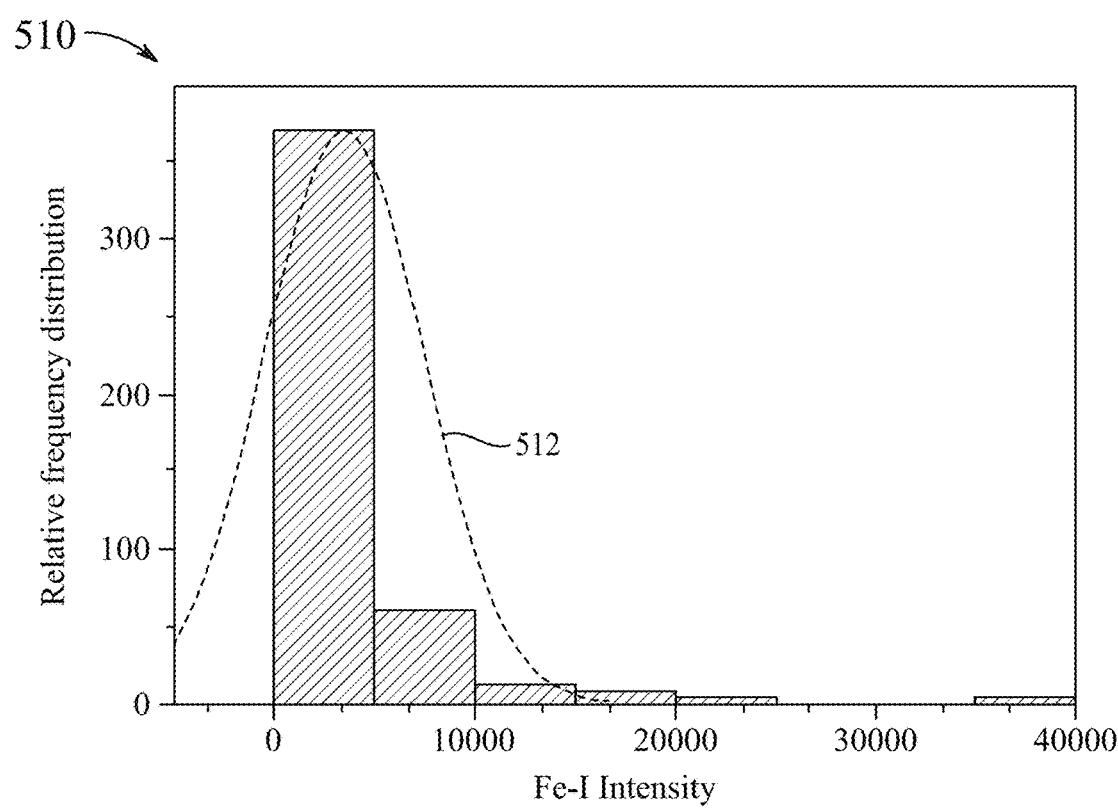
FIG. 5B is a histogram representing correlation between the relative frequency distribution and iron emission intensity, according to aspects of the present disclosure.
Figure 5C:
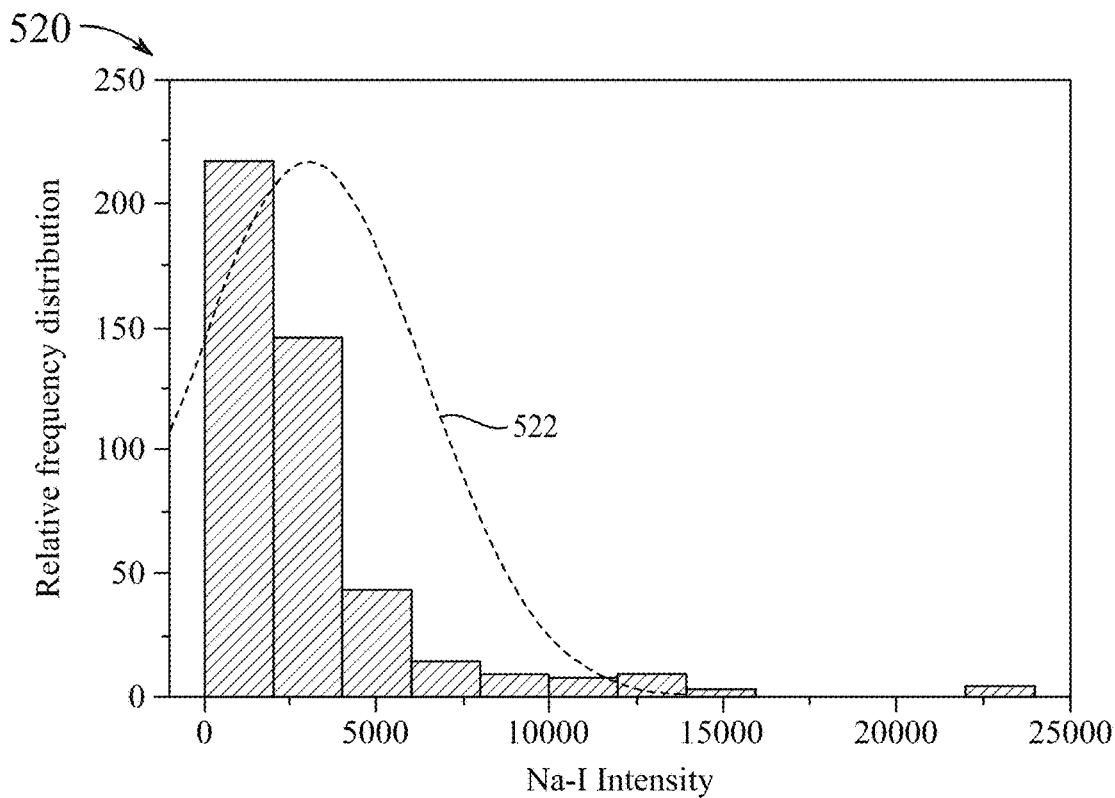
FIG. 5C is a histogram representing correlation between the relative frequency distribution and sodium emission intensity, according to aspects of the present disclosure.
Figure 5D:
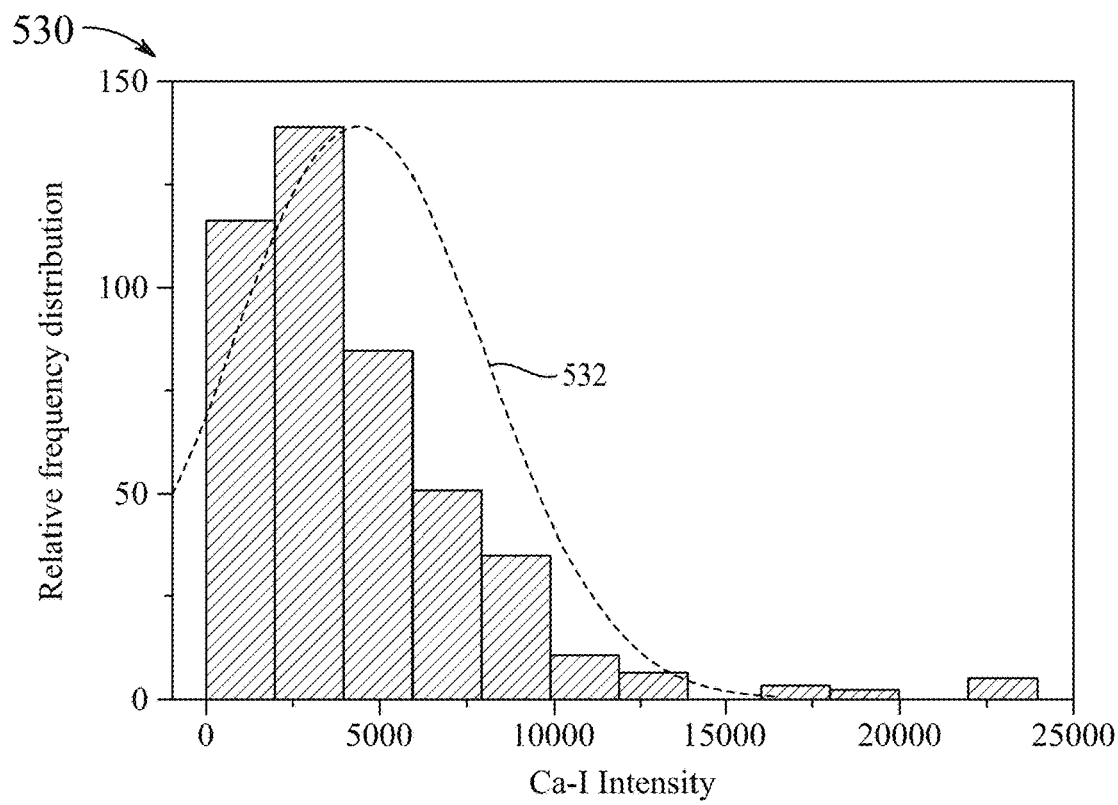
FIG. 5D is a histogram representing correlation between the relative frequency distribution and calcium emission intensity, according to aspects of the present disclosure.
Figure 5E:
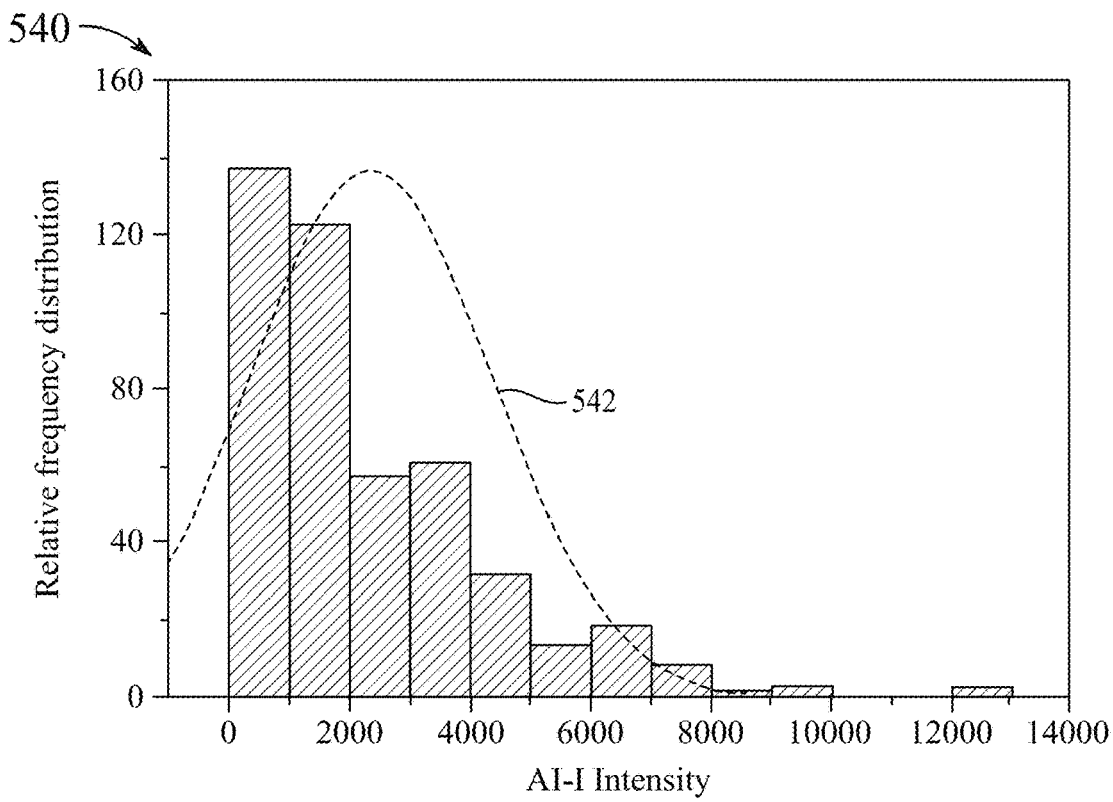
FIG. 5E is a histogram representing correlation between the relative frequency distribution and aluminium emission intensity, according to aspects of the present disclosure.
Figure 5F:
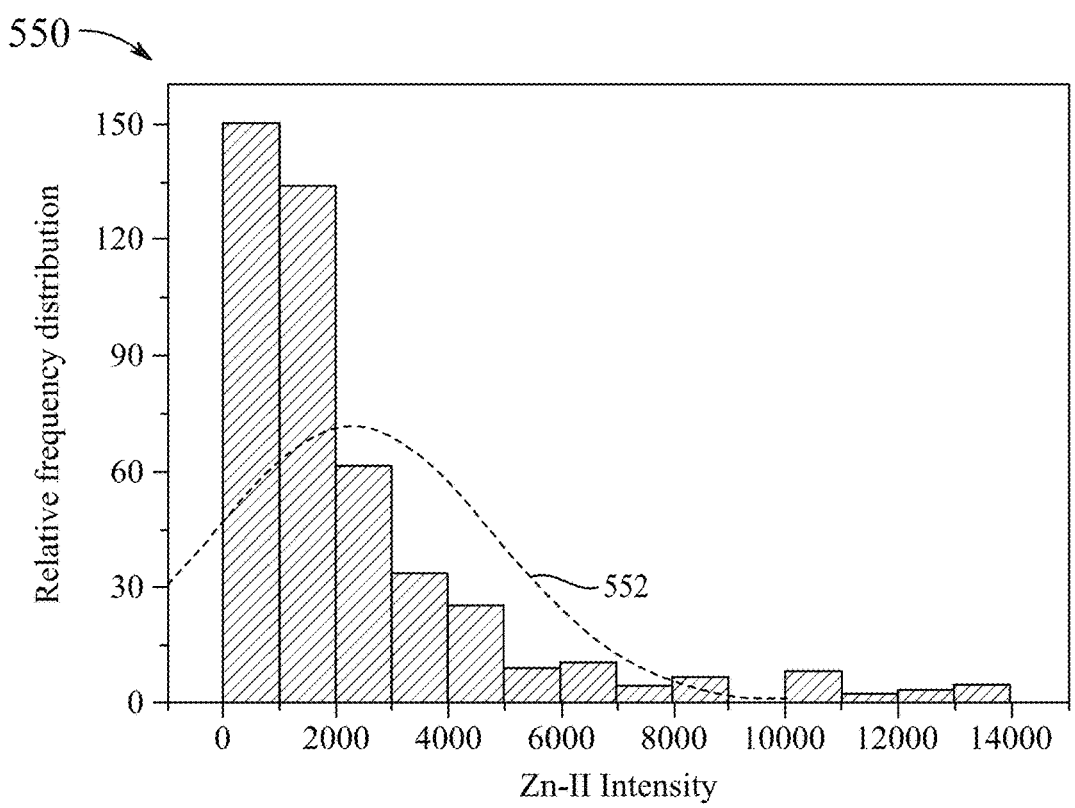
FIG. 5F is a histogram representing correlation between the relative frequency distribution and zinc emission intensity, according to aspects of the present disclosure.

FIG. 5F is a histogram representation 550 of the correlation between the relative frequency distribution and zinc emission intensity (Zn—I intensity). Curve 552 represents the statistical distribution of zinc in the soil sample.

Figure 5G:
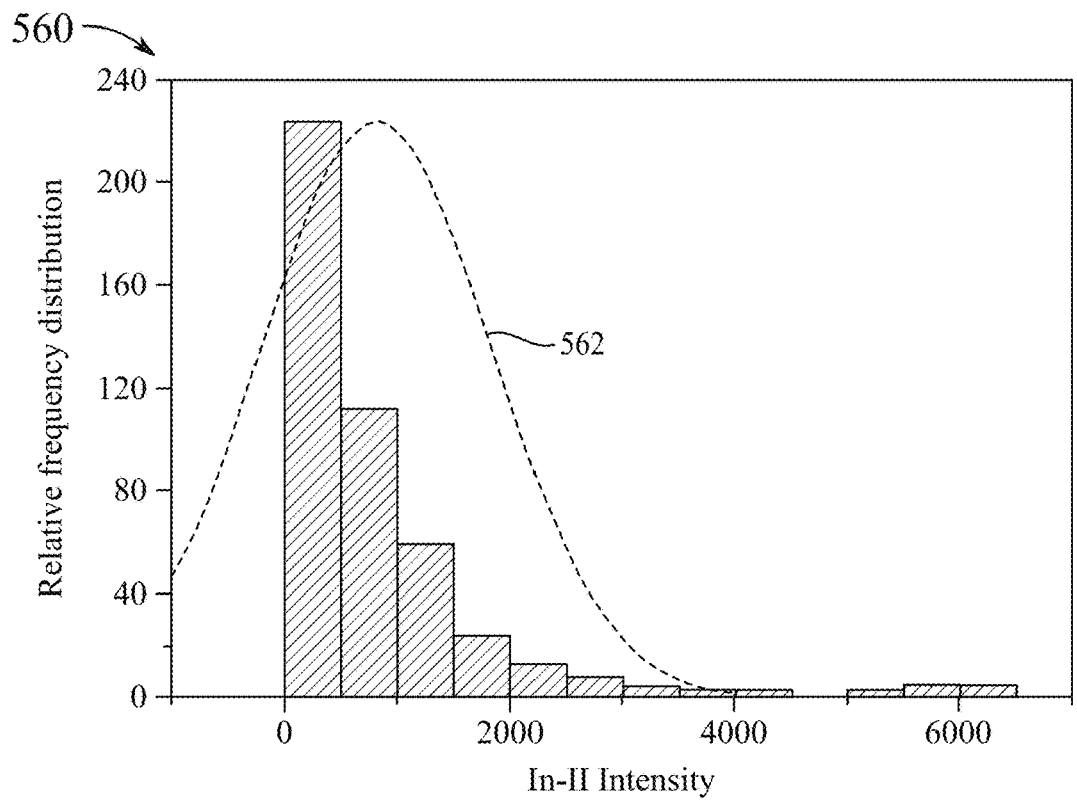
FIG. 5G is a histogram representing correlation between the relative frequency distribution and indium emission intensity, according to aspects of the present disclosure.

FIG. 5G is a histogram representation 560 of the correlation between the relative frequency distribution and indium emission intensity (In—I intensity). Curve 562 represents the statistical distribution of indium in the soil sample.

Figure 5H:
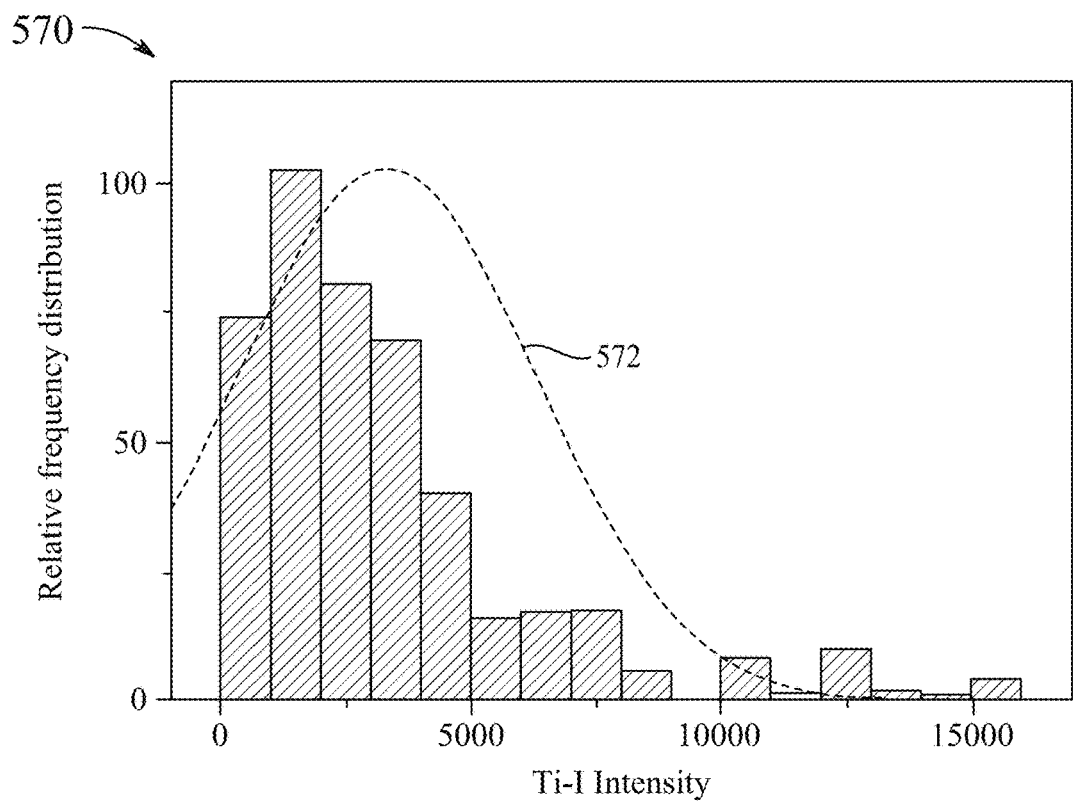
FIG. 5H is a histogram representing correlation between the relative frequency distribution and titanium emission intensity, according to aspects of the present disclosure.

FIG. 5H is a histogram representation 570 of the correlation between the relative frequency distribution and titanium emission intensity (Ti—I intensity). Curve 572 represents the statistical distribution of titanium in the soil sample.

TABLE 1a

The statistics of the dataset

|  | Si-I (a.u.) | Fe-I (a.u.) | Mg-I (a.u.) | Ca-I (a.u.) | Na-I (a.u.) | Al-I (a.u.) | Zn-II (a.u.) |
|---|---|---|---|---|---|---|---|
| count | 450 | 450 | 450 | 450 | 450 | 450 | 450 |
| mean | 2011.53 | 3472.19 | 2545.34 | 4348.18 | 3052.15 | 2357.13 | 2302.82 |
| std | 2310.70 | 4008.73 | 2459.58 | 3686.11 | 3349.30 | 2027.71 | 2522. |
| minimum | 7.120 | 7.340 | 7.260 | 30.510 | 54.210 | 8.940 | 97.380 |
| maximum | 13,569.2 | 38,302.4 | 20,496.9 | 23,850.1 | 22,487.0 | 12,691.9 | 13,182.7 |

TABLE 1b

The statistics of the employed dataset (cont.)

|  | In-II (a.u.) | Ti-I (a.u.) | O-I (a.u.) | K-I (a.u.) | bulk density (g/cm$^3$) | water con. (%) | UCS (kPa) |
|---|---|---|---|---|---|---|---|
| count | 450 | 450 | 450 | 450 | 450 | 450 | 450 |
| mean | 2011.53 | 3472.19 | 2545.34 | 4348.18 | 3052.15 | 2357.13 | 2302.82 |
| std | 2310.70 | 4008.73 | 2459.58 | 3686.11 | 3349.30 | 2027.71 | 2522. |
| minimum | 7.120 | 7.340 | 7.260 | 30.510 | 54.210 | 8.940 | 97.380 |
| maximum | 13,569.2 | 38,302.4 | 20,496.9 | 23,850.1 | 22,487.0 | 12,691.9 | 13,182.7 |

FIG. 5A is a histogram representation 500 of the correlation between the relative frequency distribution and magnesium emission intensity (Mg—I intensity). Curve 502 represents the statistical distribution of magnesium in the soil sample.

FIG. 5B is a histogram representation 510 of the correlation between the relative frequency distribution and iron emission intensity (Fe—I intensity). Curve 512 represents the statistical distribution of iron in the soil sample.

FIG. 5C is a histogram representation 520 of the correlation between the relative frequency distribution and sodium emission intensity (Na—I intensity). Curve 522 represents the statistical distribution of sodium in the soil sample.

FIG. 5D is a histogram representation 530 of the correlation between the relative frequency distribution and calcium emission intensity (Ca—I intensity). Curve 532 represents the statistical distribution of calcium in the soil sample.

FIG. 5E is a histogram representation 540 of the correlation between the relative frequency distribution and aluminium emission intensity (Al—I intensity). Curve 542 represents the statistical distribution of aluminium in the soil sample.

Figure 5I:
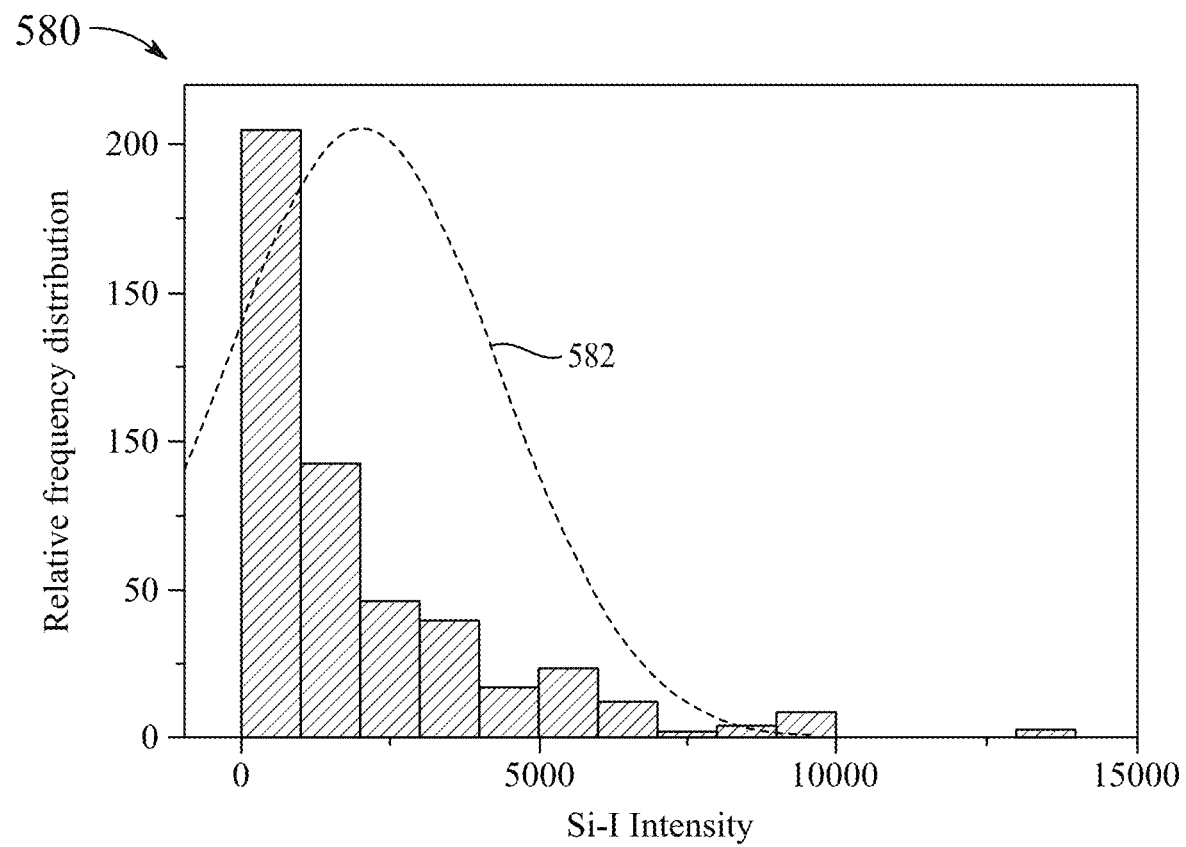
FIG. 5I is a histogram representing correlation between the relative frequency distribution and silicon emission intensity, according to aspects of the present disclosure.

FIG. 5I is a histogram representation 580 of the correlation between the relative frequency distribution and silicon emission intensity (Si—I intensity). Curve 582 represents the statistical distribution of silicon in the soil sample.

Figure 6A:
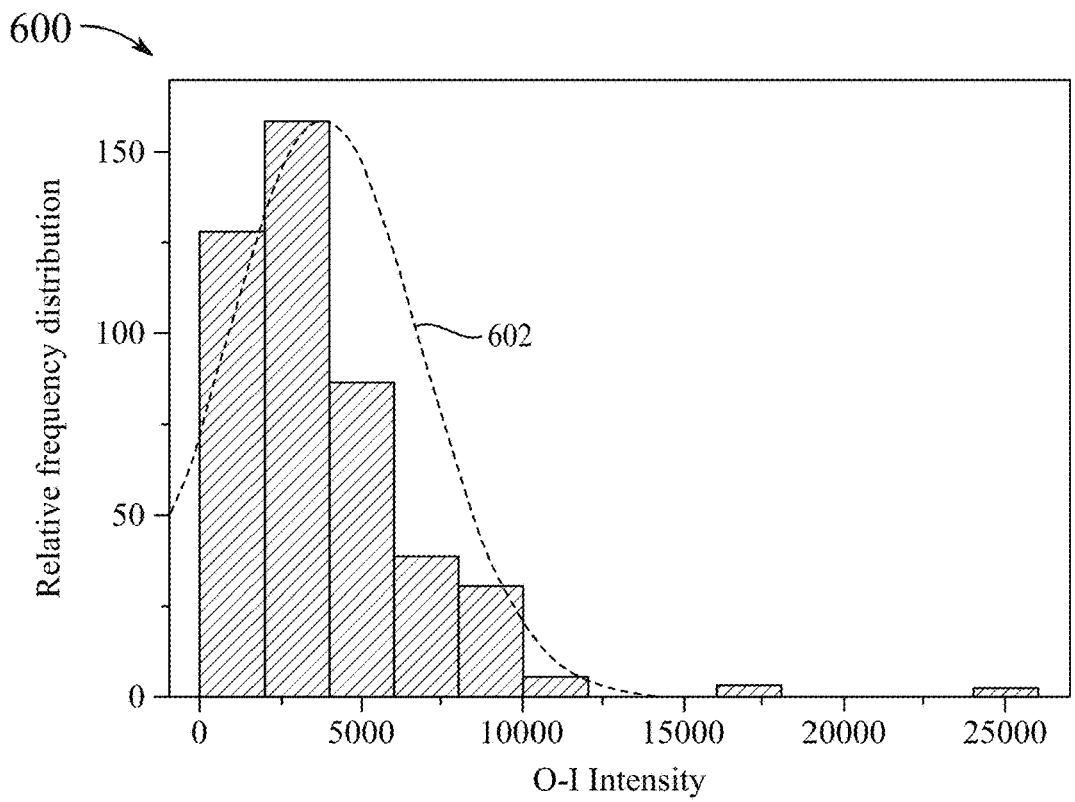
FIG. 6A is a histogram representation of correlation between the relative frequency distribution and oxygen emission intensity, according to aspects of the present disclosure.

FIG. 6A is a histogram representation 600 of a correlation between the relative frequency distribution and oxygen emission intensity (O—I intensity). Curve 602 represents the statistical distribution of the model descriptor (for example: oxygen) present in the soil sample.

Figure 6B:
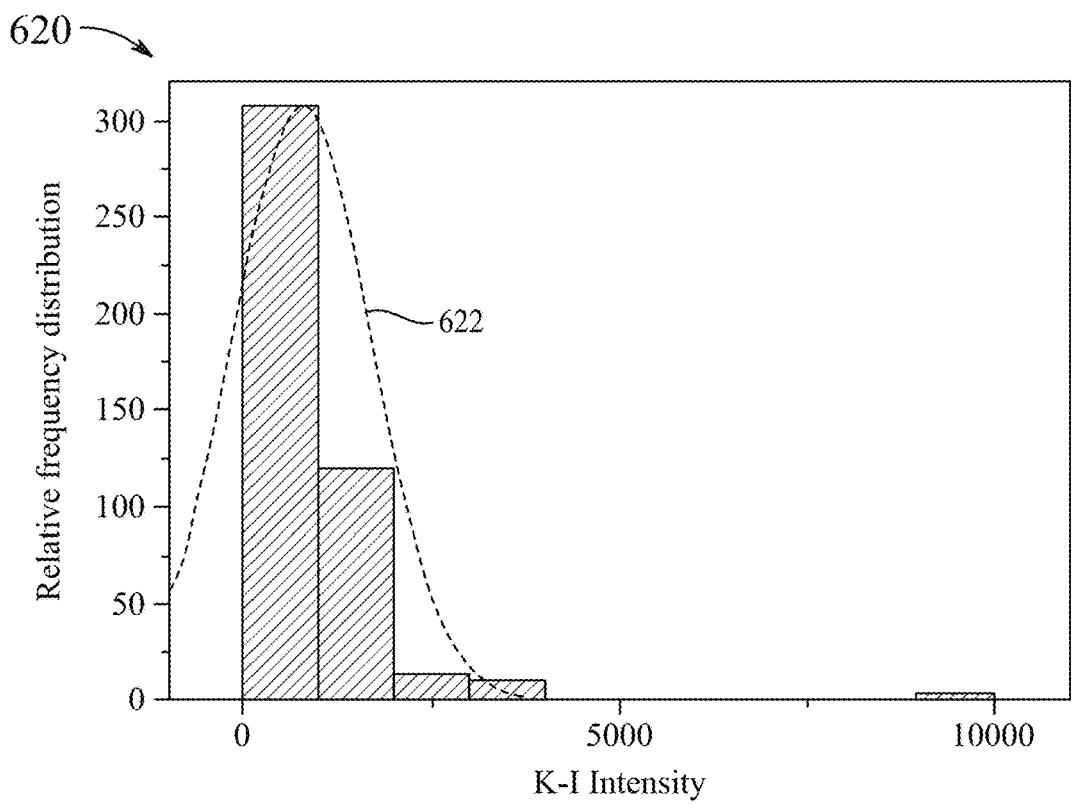
FIG. 6B is a histogram representation of correlation between the relative frequency distribution and potassium emission intensity, according to aspects of the present disclosure.

FIG. 6B is a histogram representation 620 of the correlation between the relative frequency distribution and potassium (K) emission intensity (K—I intensity). Curve 622 represents the statistical distribution of the model descriptor (for example: potassium (K)) present in the soil sample.

Figure 6C:
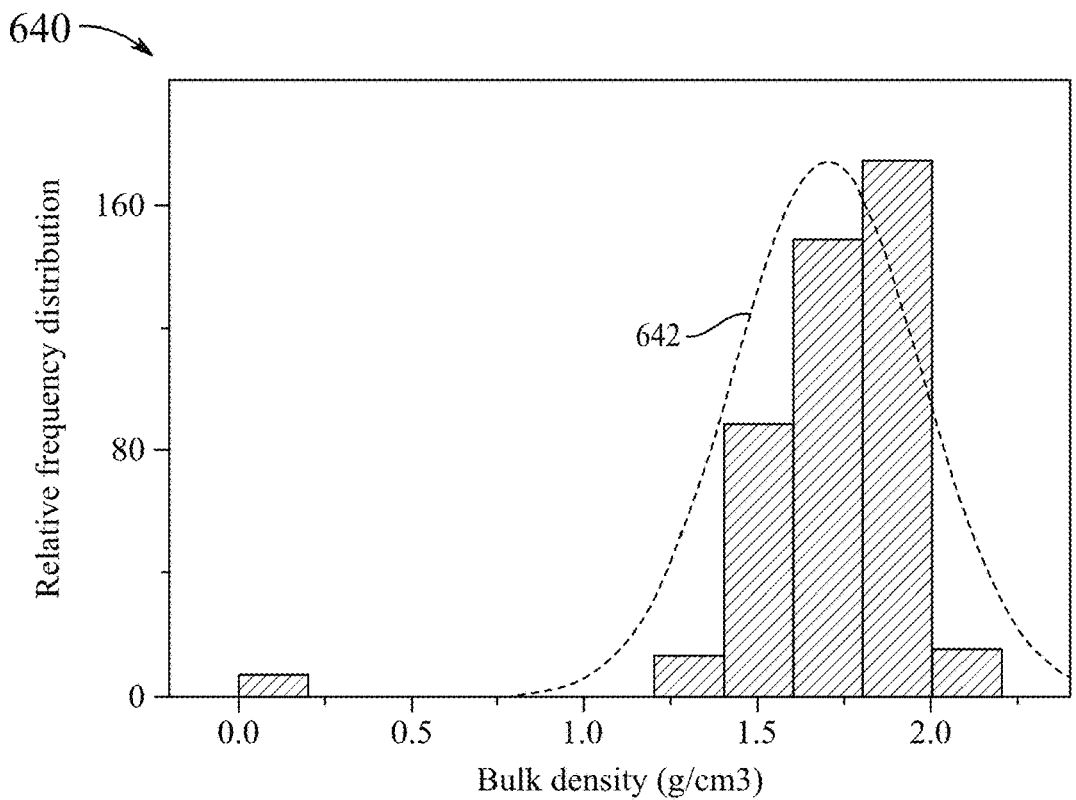
FIG. 6C is a histogram representing correlation between the relative frequency distribution and the bulk density, according to aspects of the present disclosure.

FIG. 6C is a histogram representation 640 of the correlation between the relative frequency distribution and the bulk density. Curve 642 represents the statistical distribution of the bulk density of the soil sample.

Figure 6D:
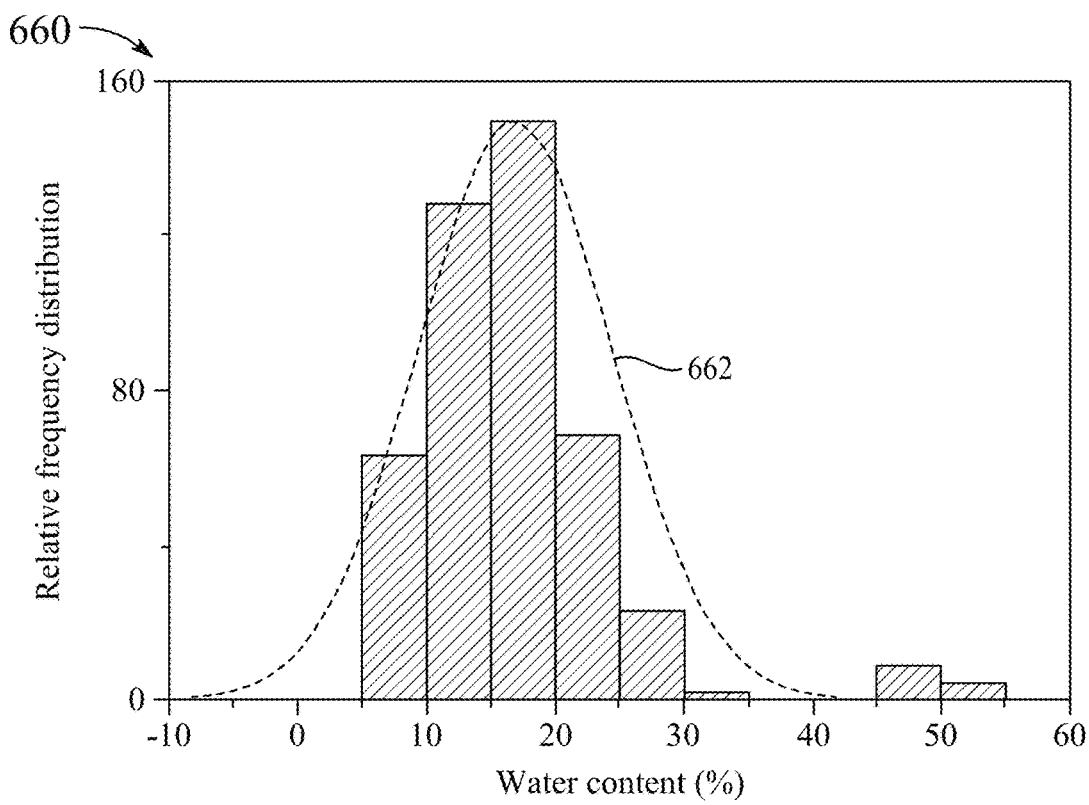
FIG. 6D is a histogram representing correlation between the relative frequency distribution and the water content, according to aspects of the present disclosure.

FIG. 6D is a histogram representation 660 of the correlation between the relative frequency distribution and the water content. Curve 662 represents the statistical distribution of the water content of the soil sample.

Figure 7:
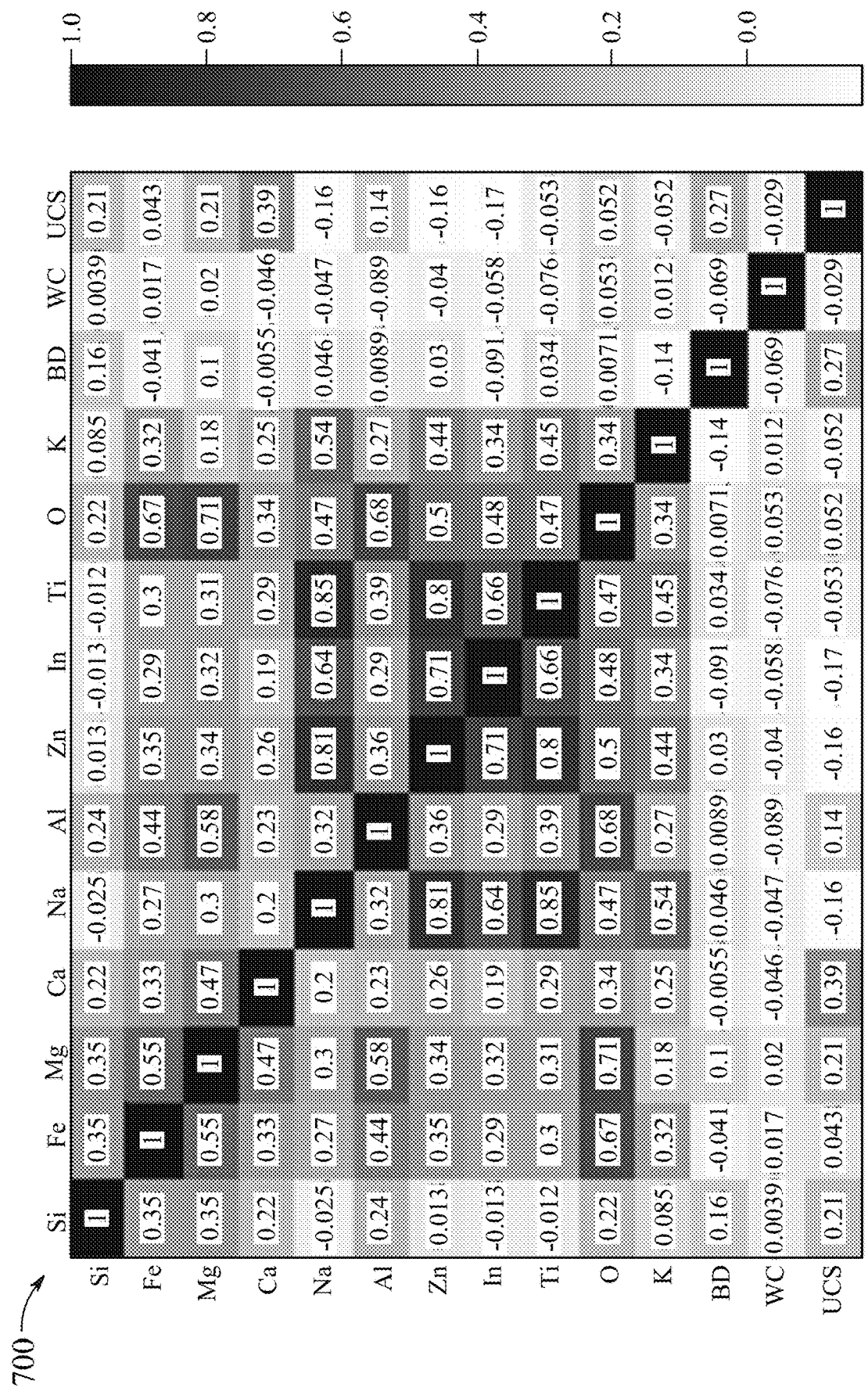
FIG. 7 illustrates a heat map representing correlation strength between input features of the machine learning model and the UCS, according to aspects of the present disclosure.

The selection of the input features (model descriptors or domain variables) is a crucial step in obtaining efficient machine learning models. During the experiments, Pearson correlation coefficients between each of the domain variables and the UCS were analyzed to determine the strongly correlated features. The Pearson correlation coefficients are a measure of the linear relationship between two continuous variables. FIG. 7 illustrates a heat map 700 representing correlation strength between the input features and the UCS of the soil. The heat map 700 also highlights the correlation between the domain variables themselves. The selected elemental intensities indicate that the elemental concentration should be well defined since the UCS may be inherently affected by the constitution of the materials. The amount of water content and bulk density of the soil samples may define its unconfirmed compressive strength. Therefore, based on this assertion and the calculated correlation coefficients, the choice of the domain variables is in order. Some of the input features, such as Na, Zn, and K, are negatively correlated with the UCS, implying that their presence reduces the absolute soil UCS value. On the other hand, a positive correlation indicates that an increase in the input features would be in favor of the UCS. The higher the absolute correlation coefficient between the descriptors and the target variable (representing UCS), the better the performance of the models.

Second Experiment: Applying Parameter Optimization.

The second experiment was conducted to optimize the parameters. The parameter optimization is first step in the development of any machine learning model because optimized parameters ensure the generalization and prediction accuracy of the model. For SVR, the selection of the defined SVR parameters (for example, epsilon parameter, Kernel parameter, gamma effects parameter, and the regularization parameter) affect the prediction performance of the model. These parameters affect how well the model performs in the following ways: the number of support vectors and the margin of tolerance are determined by epsilon parameter. The application of linear regression methods is made possible by using the kernel parameter to map a non-linear function into high-dimensional feature space. The degree to which the model is penalized for the estimated function is controlled by the regularization parameter. The model may overfit when the regularization parameter is large. Thus, the regularization parameter (C) should not be either excessively large or small. A very small regularization parameter does not sufficiently penalize the training data. A trade-off between minimizing the complexity of the model and reducing the training error is ensured by the regularization parameter. The simultaneous effect of varying epsilon parameter and the regularization parameter during the optimization process on the $R^2$ value of the UCS is presented as a contour plot as shown in FIG. 8A-FIG. 8D for both the SVR model and boosted SVR model (combined with the adaptive boosting classifier).

For DTR models, the depth of the tree is a significant component because it defines how much the tree may subcategorize data according to the distinctive features of the dataset. For the boosted SVR model and boosted DTR model (combined with the adaptive boosting classifier), the learning rates and the number of weak estimators are equally important in building efficient models. In an example, during experiments a cross validation approach was employed as the optimization strategy. In the cross validation approach, each model parameter was tracked separately, and the root mean square error (RMSE) was calculated in every situation. The defined values of the hyperparameters are the configurations with a high correlation coefficient between the actual value, and the predicted value and the lowest RMSE values.

Table 2 represents the hyperparameters used in the present disclosure to estimate the UCS. In each case, the hyperparameters are the results of the cross-validation approach conducted to determine the most suitable set of values.

TABLE 2

Defined parameters for the various models

| | SVR | SVR-ADB (boosted SVR) | DTR | DTR-ADB (boosted DTR) |
|---|---|---|---|---|
| C | 1000 | 1000 | | |
| epsilon | 0.1 | 0.1 | | |
| gamma | 0.01 | 0.01 | | |
| kernel | RBF | RBF | | |
| max depth | | | 10 | 10 |
| learning rate | | 0.1 | | 1 |
| estimators | | 25 | | 50 |

Figure 8A:
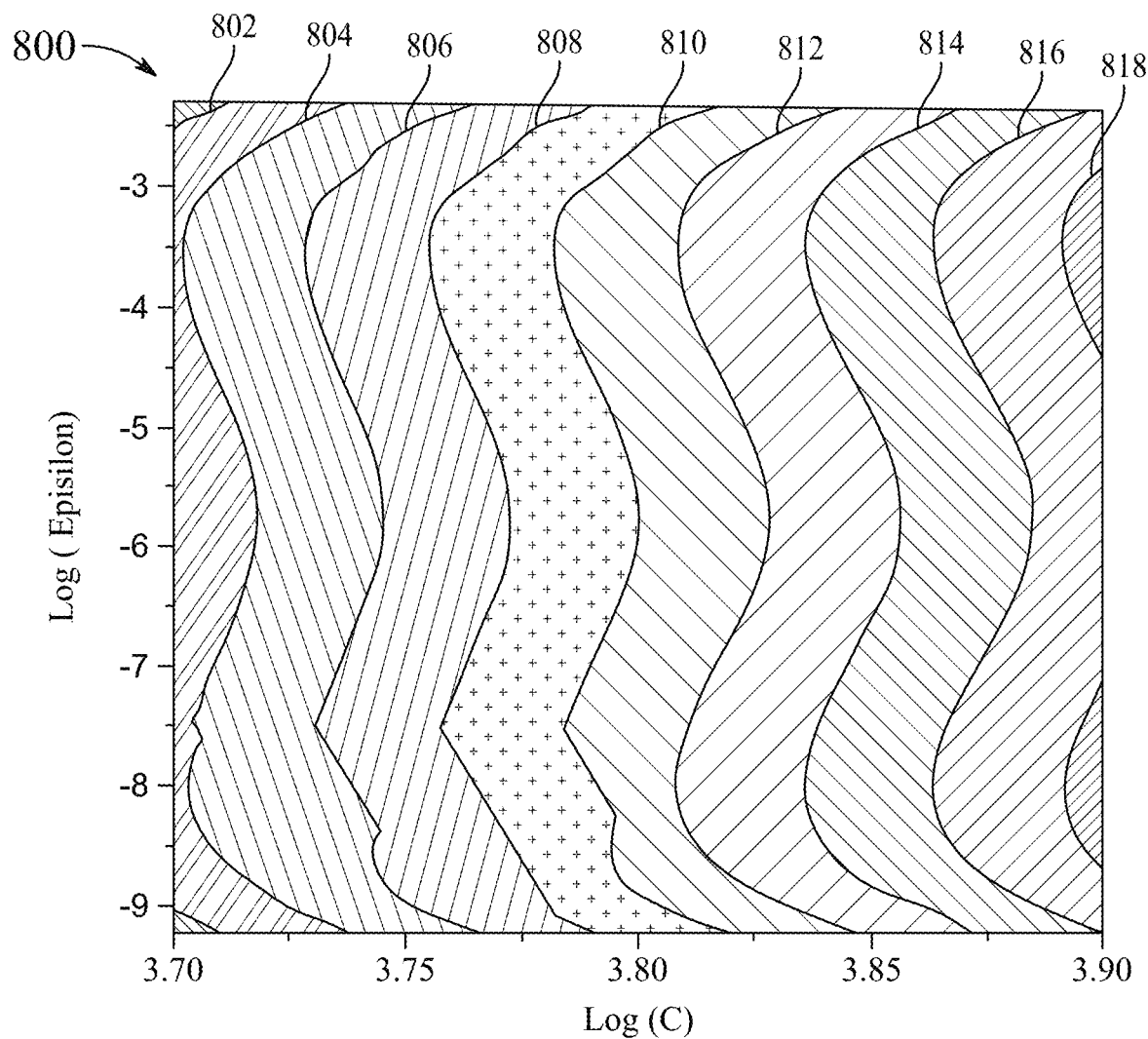
FIG. 8A is a contour plot showing dependence of the $R^2$ values on support vector regression (SVR) parameters during the testing phase of SVR model, according to aspects of the present disclosure.

FIG. 8A is a contour plot 800 showing dependence of the $R^2$ values on the SVR parameters (regularization parameter C and epsilon parameter) during the testing phase of SVR model. Curve 802 represents a value of $R^2=0.7538$, when SVR parameters are varying. Curve 804 represents a value of $R^2=0.7608$, when SVR parameters are increasing simultaneously. Curve 806 represents a value of $R^2=0.7679$. Curve 808 represents a value of $R^2=0.77490$. Curve 810 represents a value of $R^2=0.7819$. Curve 812 represents a value of $R^2=0.7889$. Curve 814 represents a value of $R^2=0.7960$. Curve 816 represents a value of $R^2=0.8030$. Curve 818 represents a value of $R^2=0.8100$.

Figure 8B:
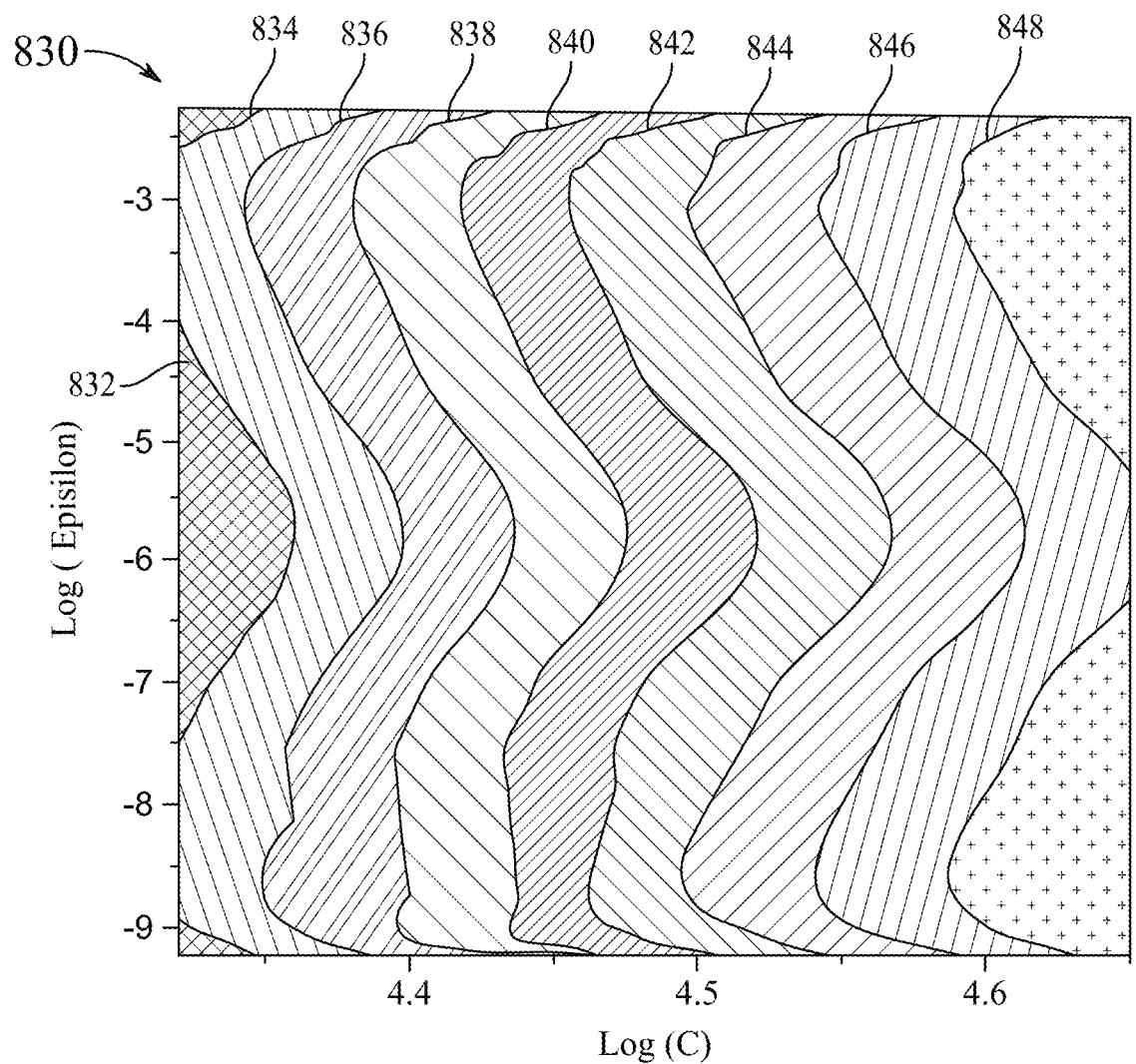
FIG. 8B is a contour plot showing dependence of the $R^2$ values on the SVR parameters during the training phase of SVR model, according to aspects of the present disclosure.

FIG. 8B is a contour plot 830 showing the dependence of the $R^2$ values on the SVR parameters during the training phase of SVR model. Curve 832 represents a value of $R^2=0.9542$, when SVR parameters are varying. Curve 834 represents a value of $R^2=0.9599$, when SVR parameters are increasing simultaneously. Curve 836 represents a value of $R^2=0.9657$. Curve 838 represents a value of $R^2=0.9714$. Curve 840 represents a value of $R^2=0.9771$. Curve 842 represents a value of $R^2=0.9828$. Curve 844 represents a value of $R^2=0.9886$. Curve 846 represents a value of $R^2=0.9943$. Curve 848 represents a value of $R^2=1.000$.

Figure 8C:
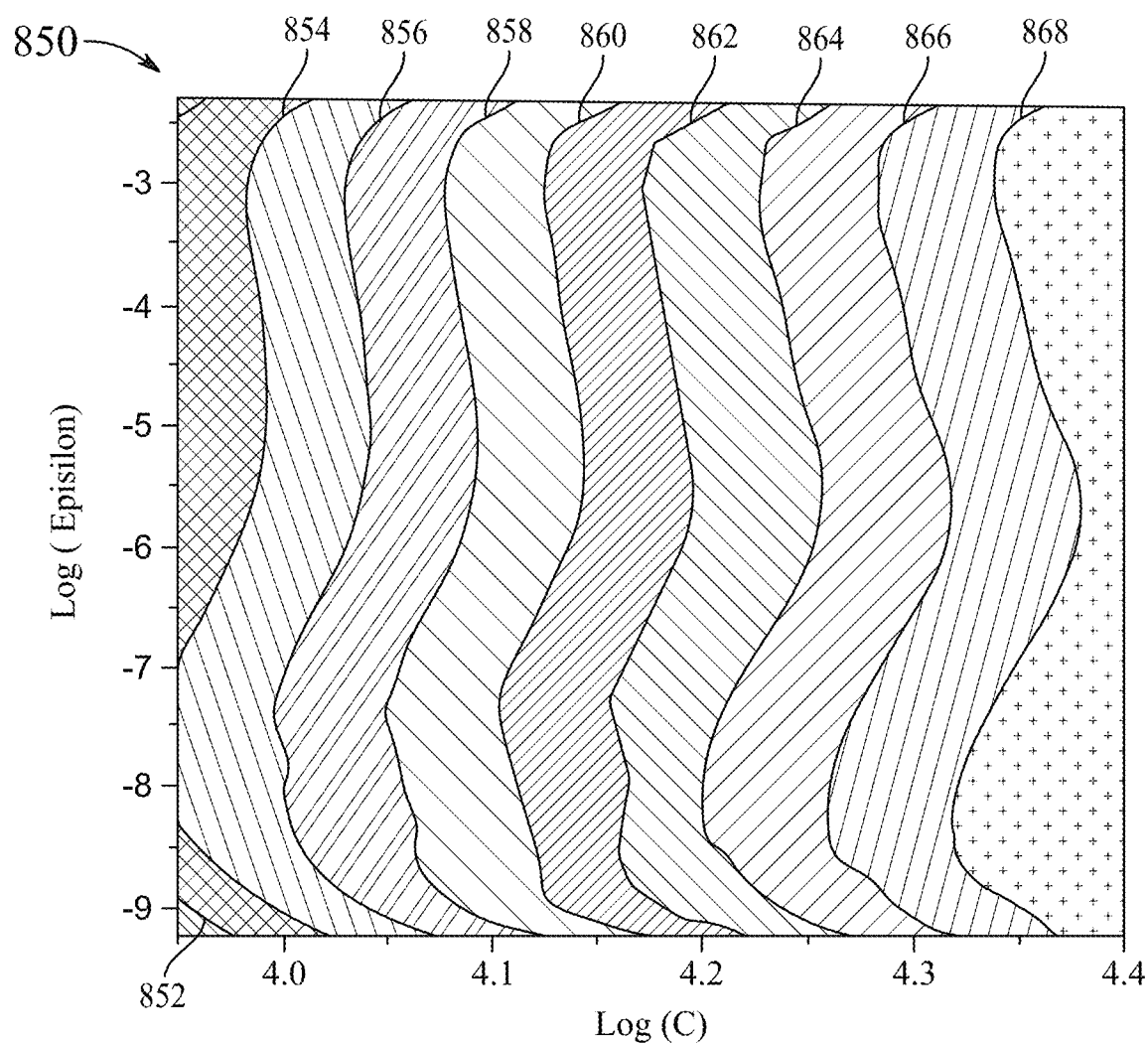
FIG. 8C is a contour plot showing dependence of the $R^2$ values on the SVR parameters during the testing phase of a boosted SVR model, according to aspects of the present disclosure.

FIG. 8C is a contour plot 850 showing the dependence of the $R^2$ values on the SVR parameters for the boosted SVR model (SVR-adaptive density balancing (ADB)) during the testing phase. Curve 852 represents a value of $R^2=0.8812$. Curve 854 represents a value of $R^2=0.8872$. Curve 856 represents a value of $R^2=0.8932$. Curve 858 represents a value of $R^2=0.8992$. Curve 860 represents a value of $R^2=0.9052$. Curve 862 represents a value of $R^2=0.9112$. Curve 864 represents a value of $R^2=0.9172$. Curve 866 represents a value of $R^2=0.9232$. Curve 868 represents a value of $R^2=0.9292$.

Figure 8D:
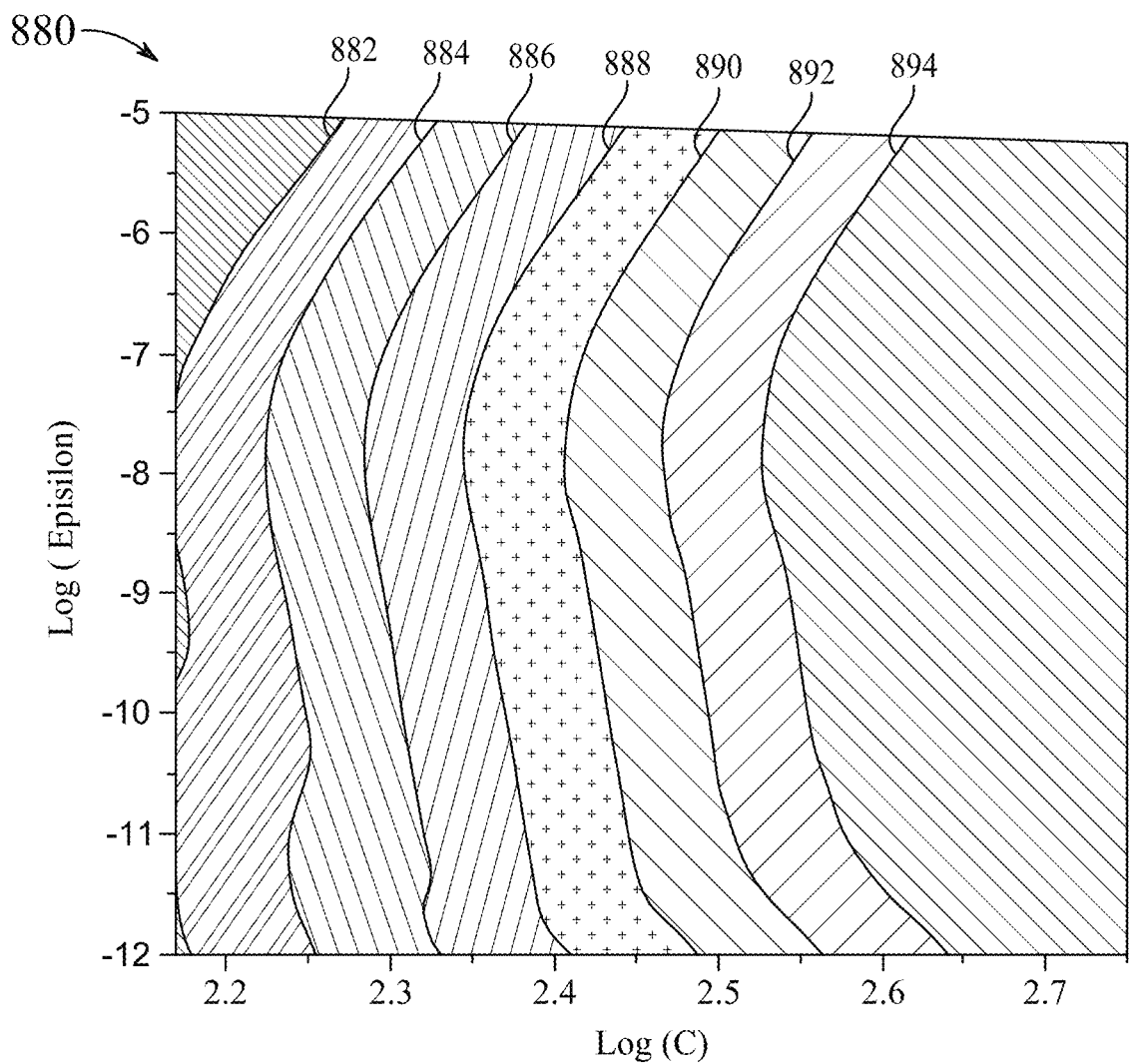
FIG. 8D is a contour plot showing dependence of the $R^2$ values on the SVR parameters during the training phase of the boosted SVR model, according to aspects of the present disclosure.

FIG. 8D is a contour plot 880 showing the dependence of the $R^2$ values on the SVR parameters for the boosted SVR model during the training phase. Curve 882 represents a value of $R^2=0.7134$. Curve 884 represents a value of $R^2=0.7217$. Curve 886 represents a value of $R^2=0.7299$. Curve 898 represents a value of $R^2=0.7381$. Curve 890 represents a value of $R^2=0.7464$. Curve 892 represents a value of $R^2=0.7547$. Curve 894 represents a value of $R^2=0.7629$.

Third Experiment: Analyzing the Predication Result of the Device 100.

The results of the predicted UCS were estimated using the two weak learners and two strong learners. To verify the generalization ability of the developed algorithms in solving external problems whose input data does not form part of the training set, the models have been used to estimate the UCS of soils stabilized with cement and lime.

Figure 9A:
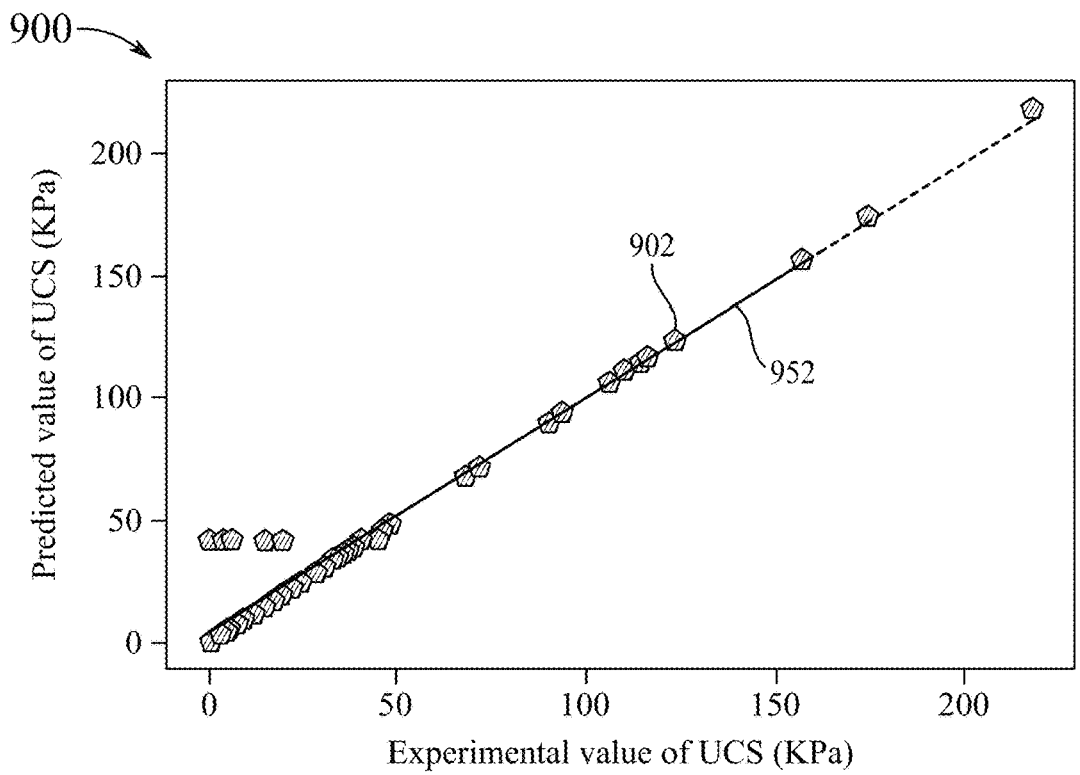
FIG. 9A is a graph representing comparison of predicted UCS values and experimentally measured UCS values obtained from the SVR model during the testing phase, according to aspects of the present disclosure.
Figure 9B:
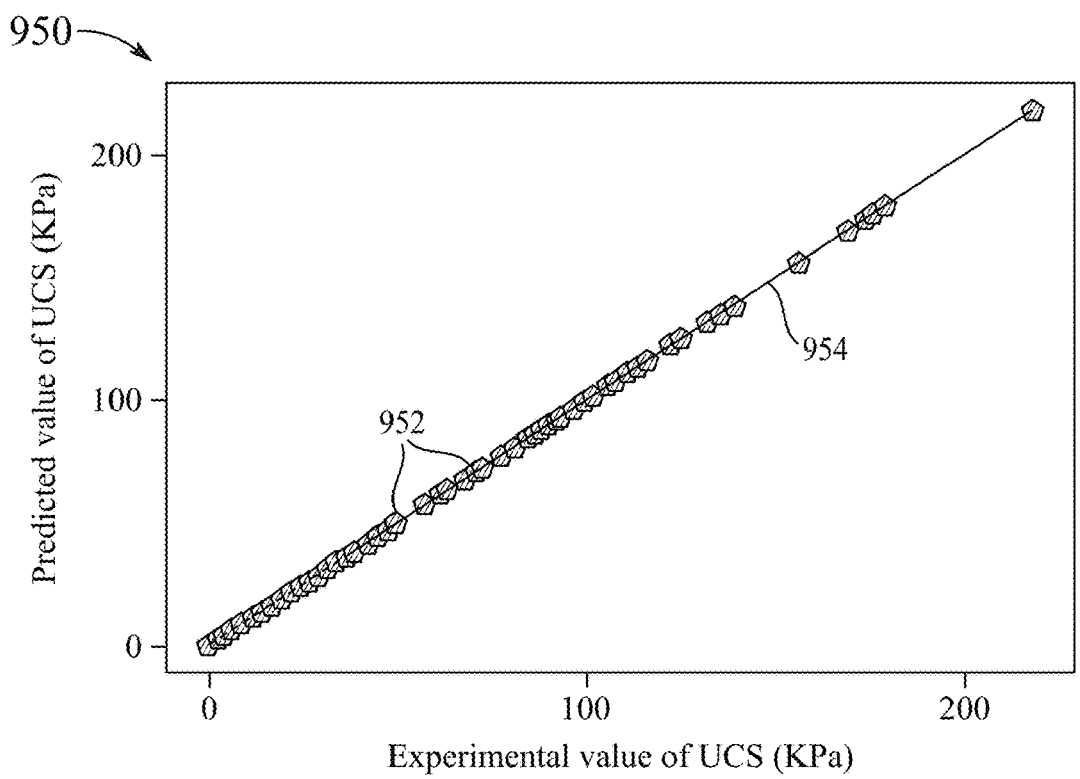
FIG. 9B is a graph representing comparison of predicted UCS values and experimentally measured UCS values obtained from the SVR model during the training phase, according to aspects of the present disclosure.

FIG. 9A-FIG. 9B show the cross plots between the predicted values and the experimental values of the UCS obtained from a SVR-Radial Basis Function (RBF) model (SVR model) respectively.

FIG. 9A is a graph 900 representing comparison of the predicted UCS values and experimentally measured UCS values obtained from the SVR model during the testing phase. Hexagonal objects 902 represent the experimental UCS values. Line 904 represents predicted UCS values. From FIG. 9A, it is evident that the experimental UCS values and the projected UCS values are linearly related.

FIG. 9B is a graph 950 representing comparison of the predicted UCS values and experimentally measured UCS values obtained from the SVR model during the training phase. Hexagonal objects 952 represent the experimental UCS values. Line 954 represents the predicted UCS values. It can be observed from FIG. 9B that the experimental UCS values and the projected UCS values are linearly related.

Figure 10A:
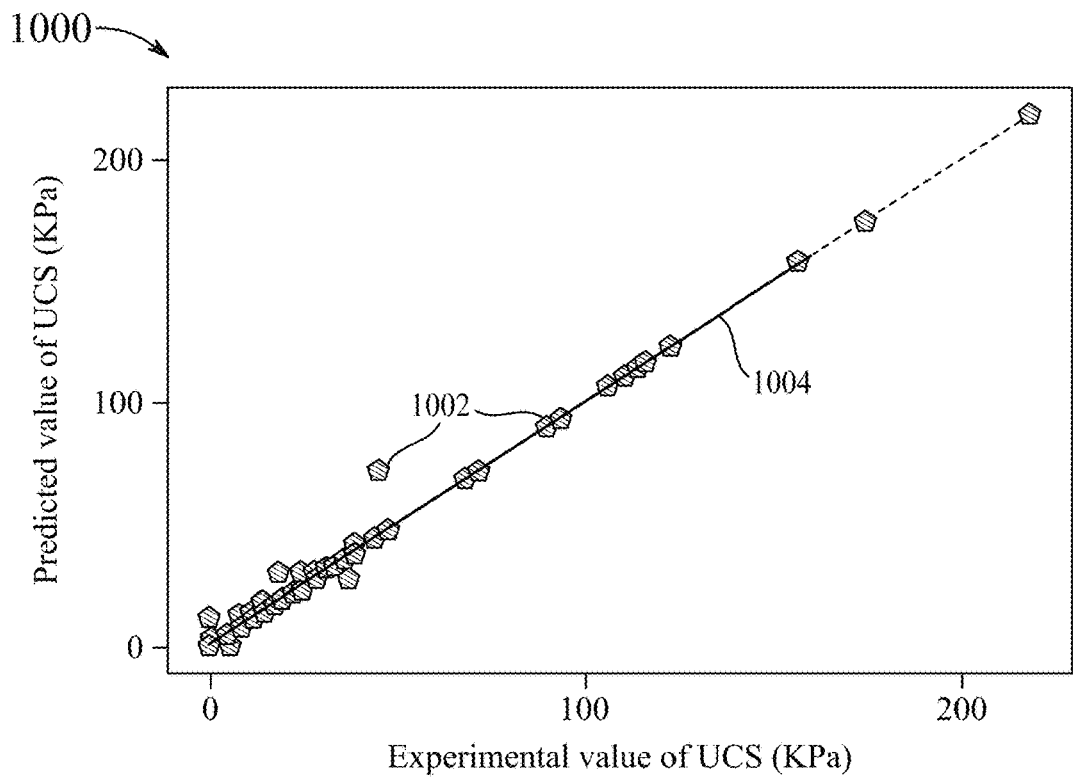
FIG. 10A is a graph representing comparison of predicted UCS values and experimentally UCS values obtained from a decision tree regression (DTR) model during the testing phase, according to aspects of the present disclosure.

FIG. 10A is a graph 1000 representing comparison of the predicted UCS values and experimentally UCS values obtained from the DTR model during the testing phase. Hexagonal objects 1002 represent the experimental UCS values. Line 1004 represents predicted UCS values. FIG. 10A represents a linear relationship between the predicted values of UCS and the experimental values of the UCS.

Figure 10B:
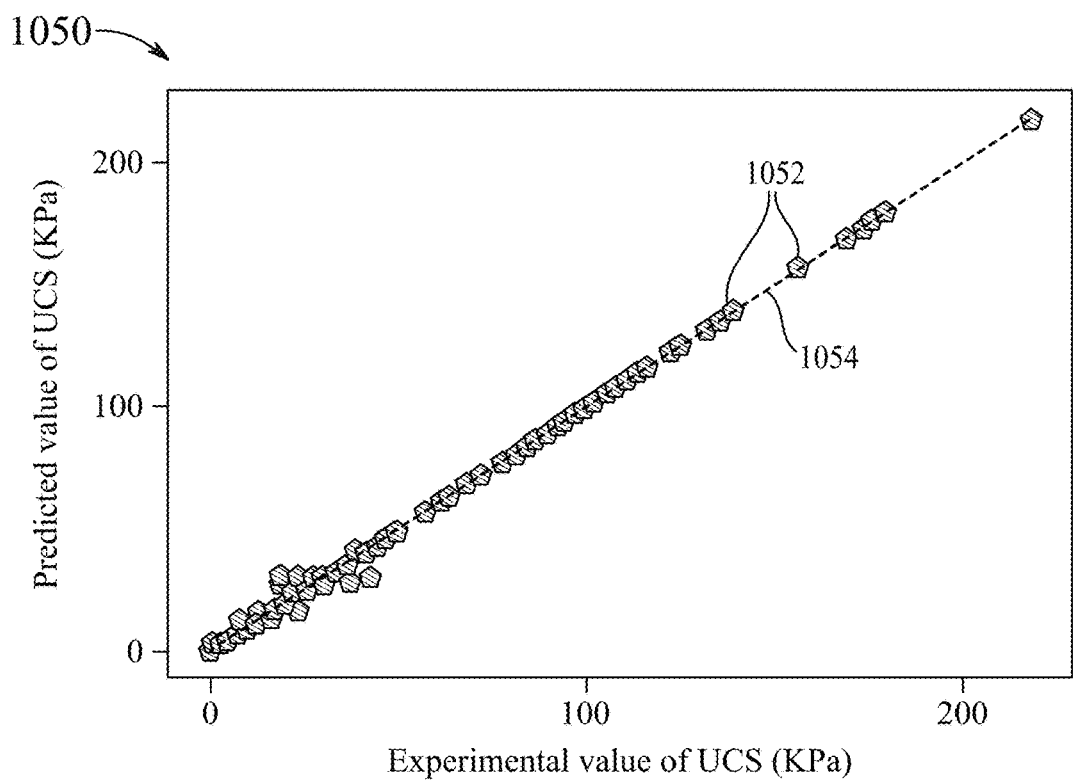
FIG. 10B is a graph representing comparison of the predicted UCS values and experimentally measured UCS values obtained from the DTR model during the training phase, according to aspects of the present disclosure.

FIG. 10B is a graph 1050 representing comparison of the predicted UCS values and experimentally measured UCS values obtained from the DTR model during the training phase. Hexagonal objects 1052 represent the experimental UCS values. Line 1054 represents the predicted UCS value. A linear relationship between the predicted value of UCS and the experimental value of the UCS, can be observed from FIG. 10B.

The two models (DTR model and the SVR model) show excellent agreement between the actual UCS value and the predicted ones, as confirmed by the metric performance indicators presented in the subsequent sections. Furthermore, adaptive boosting (using an Adaboost model) was also applied to DTR model and enhanced performance of the boosted DTR model was analyzed as shown in FIG. 11A-FIG. 11B.

Figure 11A:
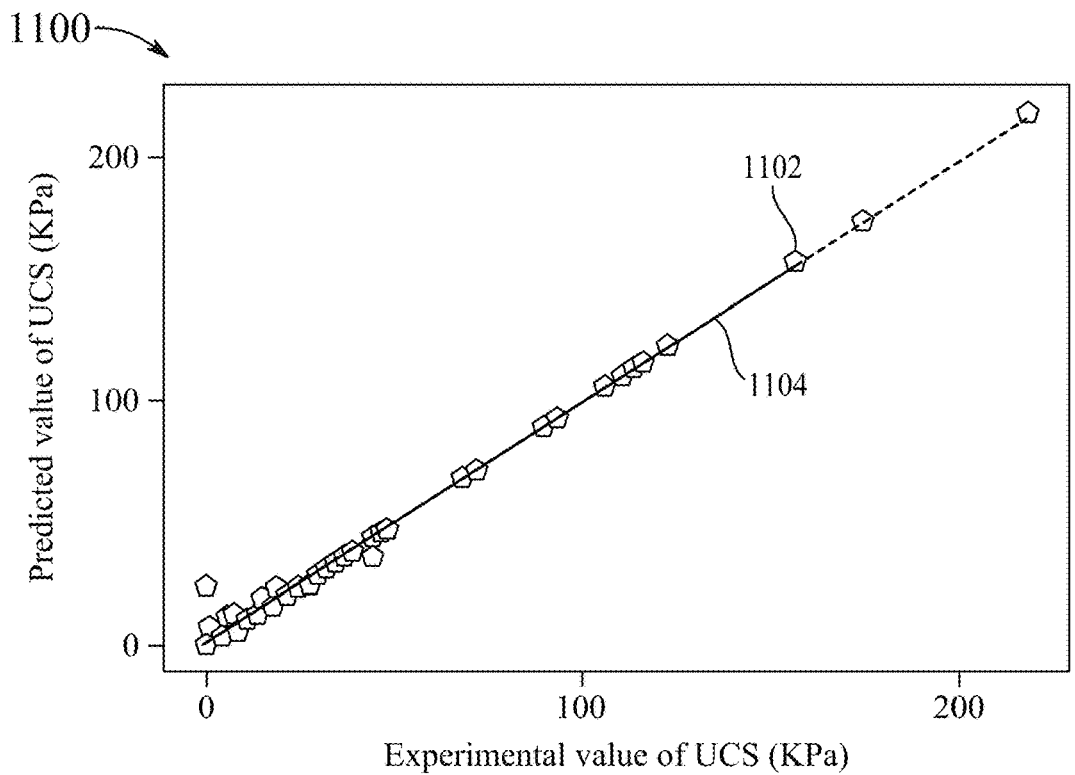
FIG. 11A is a graph representing comparison of the predicted UCS values and the experimentally measured UCS values obtained from a boosted DTR model during the testing phase, according to aspects of the present disclosure.

FIG. 11A is a graph 1100 representing comparison of the predicted UCS values and the experimentally measured UCS values obtained from the boosted DTR model during the testing phase. Hexagonal objects 1102 represent the experimental UCS values. Line 1104 represents predicted UCS values. FIG. 11A represents a linear relationship between the predicted UCS values and the experimental value of the UCS.

Figure 11B:
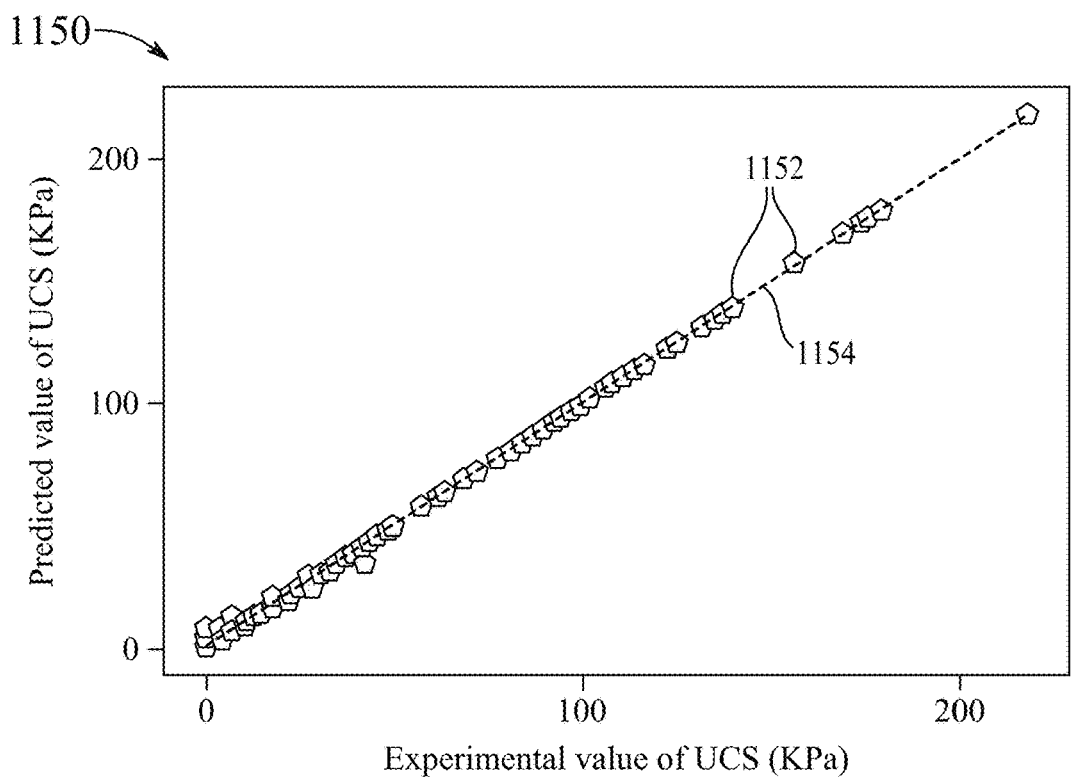
FIG. 11B is a graph representing comparison of the predicted UCS values and the experimentally measured UCS values obtained from the boosted DTR model during the training phase, according to aspects of the present disclosure.

FIG. 11B is a graph 1150 representing comparison of the predicted UCS values and the experimentally measured UCS values obtained from the boosted DTR model during the training phase. Hexagonal objects 1152 represent the experimental UCS values. Line 1154 represents predicted UCS values. A linear relationship between the predicted UCS values and the experimental value of the UCS is concluded by FIG. 11B.

Figure 12A:
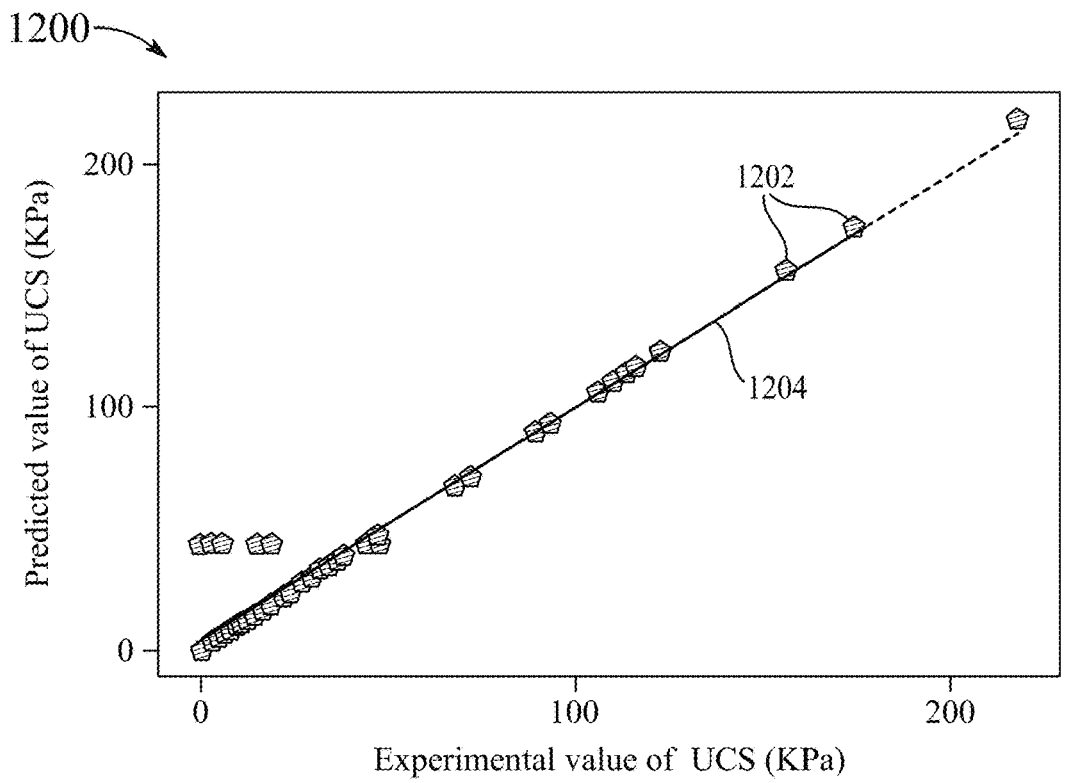
FIG. 12A is a graph representing comparison of the predicted UCS values and experimentally measured UCS values obtained from the boosted SVR model during the testing phase, according to aspects of the present disclosure.

FIG. 12A is a graph 1200 representing comparison of the predicted UCS values and experimentally measured UCS values obtained from the boosted SVR model during the testing phase. Hexagonal objects 1202 represent the experimental UCS values. Line 1204 represents predicted UCS values.

Figure 12B:
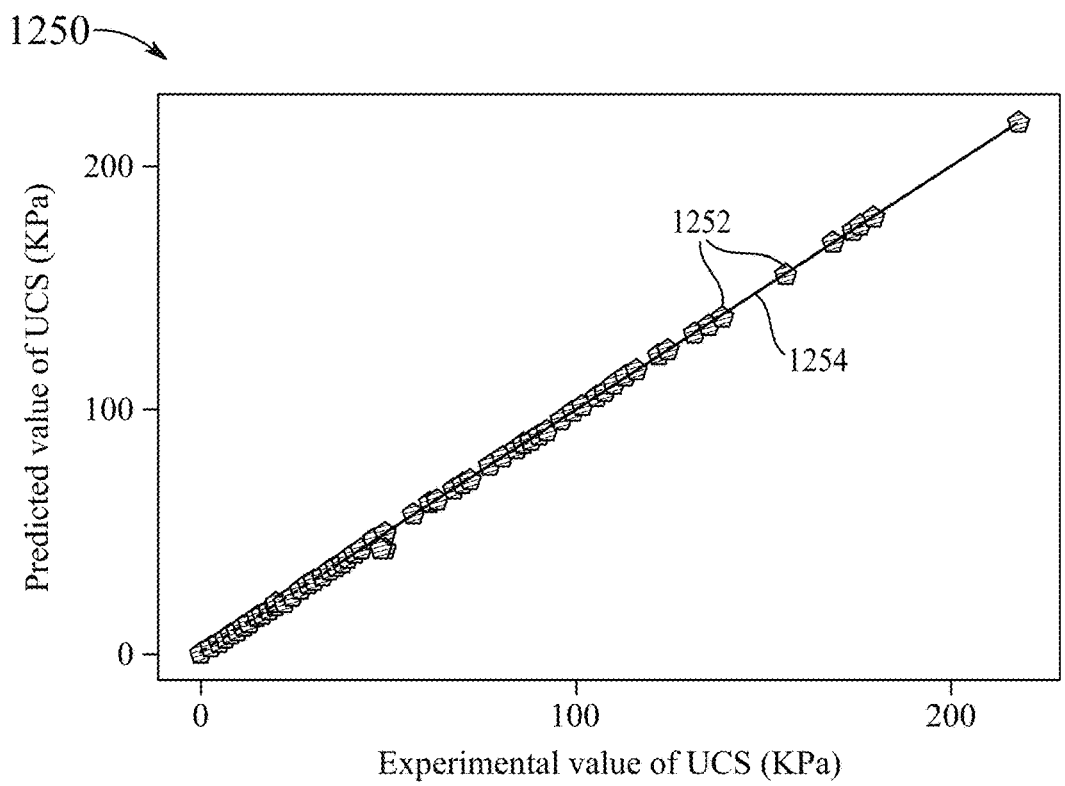
FIG. 12B is a graph representing comparison of the predicted UCS values and experimentally measured UCS values obtained from the boosted SVR model during the training phase, according to aspects of the present disclosure.

FIG. 12B is a graph 1250 representing comparison of the predicted UCS values and experimentally measured values obtained from the boosted SVR model during the training phase. Hexagonal objects 1252 represent the experimental UCS values. Line 1254 represents predicted UCS values.

The accuracy and the generalization of the four models disclosed in the present disclosure were determined based on various metric performance indicators such as mean absolute error, and root means square error, the correlation coefficient between the predicted and experimental UCS, and $R^2$ value. Equations (23)-(25) are used to summarize the mathematical description of such metric performance indicators:

$$MSE = \frac{1}{N}\sum_{i=1}^{N}(Y_{act} - Y_{pred})^2, \quad (23)$$

$$MAE = \frac{1}{N}\sum_{i=1}^{N}|Y_{act} - Y_{pred}|, \quad (24)$$

$$R^2 \text{ value} = 1 - \frac{\text{sum of squared error}}{\text{sum of squared total}}, \quad (25)$$

where $$\text{sum of squared error} = \sum_{i=1}^{i=N}(Y_{act} - Y_{pred})^2,$$

$$\text{sum of squared total} = \sum_{i=1}^{i=N}(Y_{act} - \text{mean }(Y_{pred}))^2,$$

where N represents the total number of data points, MAE is the mean absolute error, MSE is the mean square error, $Y_{act}$ represents the actual value of the UCS, and $Y_{pred}$ represents the predicted UCS.

The four metric performance indicators (MAE, $R^2$, CC, RMSE) of the four models are presented in Table 3 for the testing phase. It is evident from Table 3 that the boosted DTR model outperformed the rest of the models in terms of $R^2$ value and correlation coefficient between the predicted and actual UCS values. The boosted DTR model also exhibited the lowest mean absolute error and root mean square error values.

TABLE 3

| Model performance evaluators during testing | | | | |
|---|---|---|---|---|
| | SVR | SVR-ADB (boosted SVR) | DTR | DTR-ADB (boosted DTR) |
| $R^2$ | 0.9528 | 0.95228 | 0.98975 | 0.990396 |
| MAE | 2.4476 | 2.45238 | 1.5355 | 1.2834 |
| RMSE | 8.8229 | 8.87298 | 4.12494 | 3.98072 |
| CC | 0.97754 | 0.9773 | 0.99494 | 0.99519 |

Figure 13A:
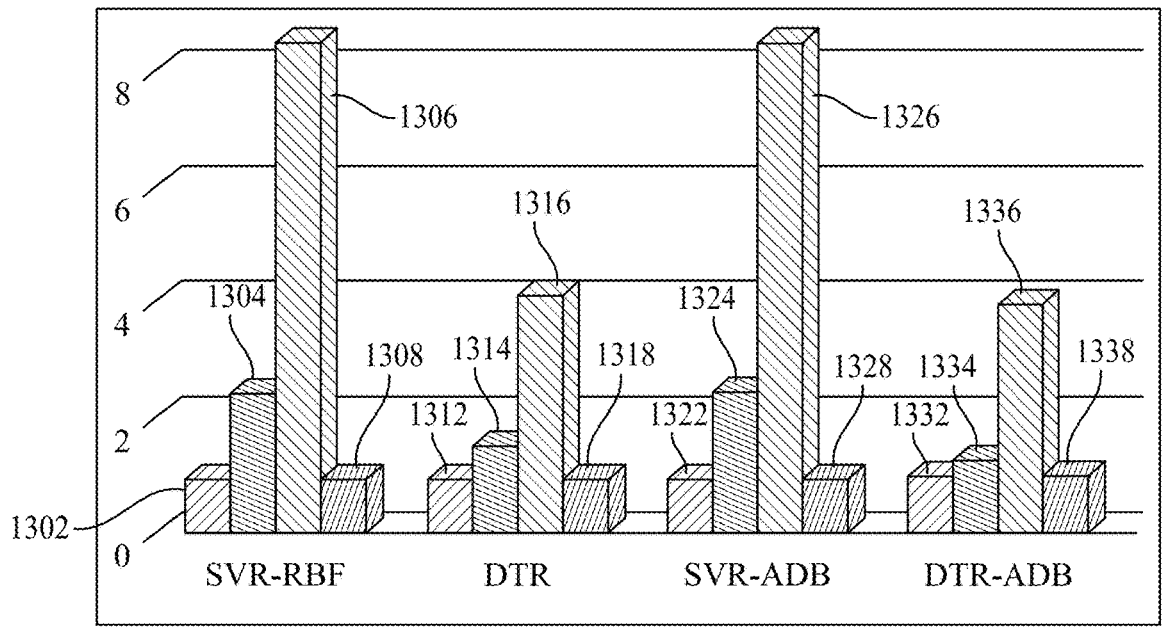
FIG. 13A is a graph representing performance of various models during the testing phase, according to aspects of the present disclosure.
Figure 13B:
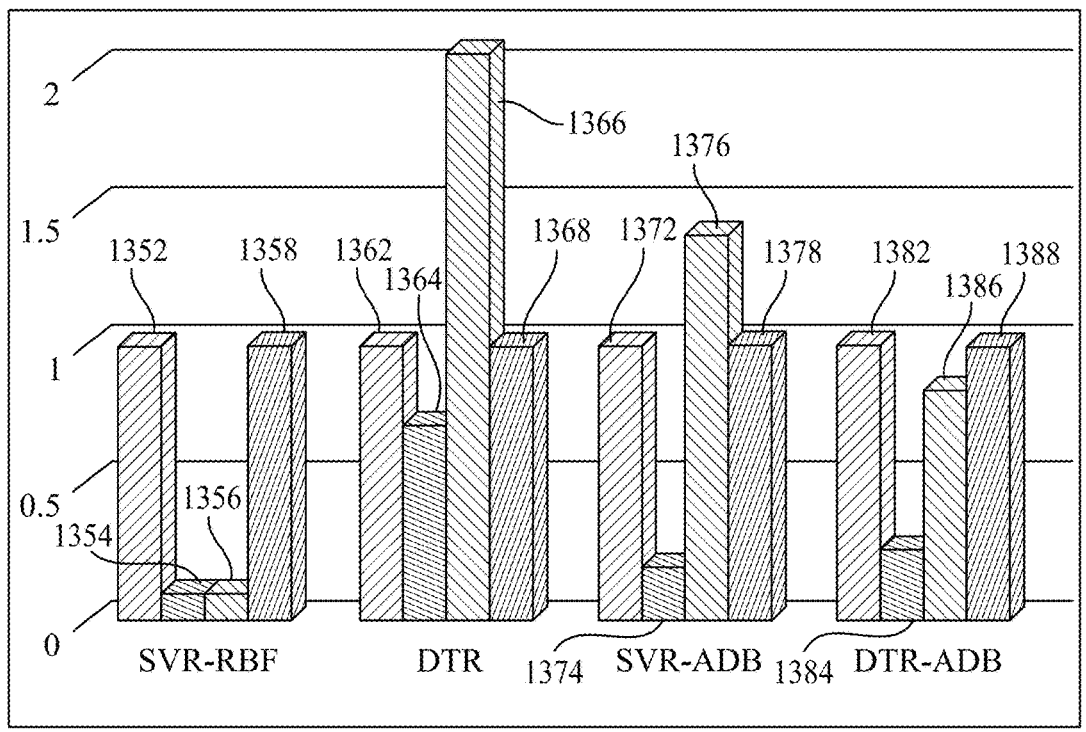
FIG. 13B is a graph representing performance of various models during the training phase, according to aspects of the present disclosure.

Table 3 also proves that the boosted DTR model is suitable for the estimation of physical quantity owing to its ability to efficiently model the complex relationship between the elemental emission intensities (chemical property) and the UCS. The performance of the boosted SVR model is marginally less than that of the weak learners, with $R^2$ values of 0.9522 and 0.9528 for the boosted SVR and SVR, respectively. This simply shows that the weak learner adequately captured the inherent complex relationships between the descriptors and the target variable, thus the marginal difference in performance. Both the SVR model and DTR model have performed excellently in determining the UCS of the soil based on the correlation between the experimental and predicted data. All the metric performance indicators follow a given pattern. For example, the boosted DTR exhibited the highest values of $R^2$ and correlation coefficient with the lowest values of mean absolute error, and root means square error as expected. The boosted SVR is characterized by the lowest $R^2$ and correlation coefficient with the highest mean absolute error and root means square error, as depicted in FIG. 13A-FIG. 13B. Therefore, the boosted DTR was chosen to be used in the field portable device to find the unconfined compressive strength of each soil sample.

FIG. 13A is a graph 1300 representing performance of various models (SVR, DTR, boosted SVR, and boosted DTR) during the testing phase. During the testing phase, various performance indicators were measured for each model. In an example, the various performance metrics include $R^2$, MAE, RMSE, and CC (cross correlation). Bar 1302 represents $R^2$ for the SVR model. Bar 1304 represents MAE for SVR model. Bar 1306 represents the RMSE for the SVR model. Bar 1308 represents the CC for the SVR model. Bar 1312 represents $R^2$ for the DTR model. Bar 1314 represents the MAE for the DTR model. Bar 1316 represents the RMSE for the DTR model. Bar 1318 represents the CC for the DTR model. Bar 1322 represents $R^2$ for the boosted SVR model. Bar 1324 represents the MAE for the boosted SVR model. Bar 1326 represents the RMSE for the boosted SVR model. Bar 1328 represents the CC for the boosted SVR model. Bar 1332 represents $R^2$ for the boosted DTR model. Bar 1334 represents the MAE for the boosted DTR model. Bar 1336 represents the RMSE for the boosted DTR model. Bar 1338 represents the CC for the boosted DTR model.

FIG. 13B is a graph 1350 representing performance of various models during the training phase. Bar 1352 represents $R^2$ for the SVR model. Bar 1354 represents the MAE for the SVR model. Bar 1356 represents the RMSE for the SVR model. Bar 1358 represents the CC for the SVR model. Bar 1362 represents $R^2$ for the DTR model. Bar 1364 represents the MAE for the DTR model. Bar 1366 represents the RMSE for DTR model. Bar 1368 represents the CC for DTR model. Bar 1372 represents $R^2$ for boosted SVR model. Bar 1374 represents the MAE for boosted SVR model. Bar 1376 represents the RMSE for boosted SVR model. Bar 1378 represents the CC for boosted SVR model. Bar 1382 represents the $R^2$ metric for boosted DTR model. Bar 1384 represents the MAE for boosted DTR model. Bar 1386 represents the RMSE for boosted DTR model. Bar 1388 represents the CC for boosted DTR model.

The metric performance indicators for the training phase are presented in table 4. Interestingly, the weak SVR learners exhibited the highest $R^2$-value and coefficient of correlation between the experimental UCS values and the predicted UCS values during the training phase, followed by the boosted SVR. Although the DTR model and the boosted DTR model performed less well than the SVR models during the training phase, their ability to outperform the SVR models during the testing and validation phases clearly demonstrates their generalization strength in predicting the UCS of the unseen input dataset. The trend of the metric performance indicators during the training phase was similar to the testing phase, with the SVR model exhibiting the highest $R^2$-value and CC with the lowest MAE and RMSE, while on the other hand, the DTR model showed the lowest $R^2$-value and CC with the highest MAE and RMSE.

TABLE 4

Model performance evaluators during training

| | SVR | SVR-ADB (boosted SVR) | DTR | DTR-ADB (boosted DTR) |
|---|---|---|---|---|
| $R^2$ | 0.999994 | 0.9989712 | 0.997748 | 0.999634 |
| MAE | 0.09944 | 0.1997737 | 0.713849 | 0.261605 |
| RMSE | 0.099709 | 1.3961107 | 2.065309 | 0.832292 |
| CC | 0.999999 | 0.99949 | 0.99887 | 0.999819 |

In the present disclosure, the dataset was divided in the ratio of 80:20. The model was trained using 80% of the dataset and tested using the remaining 20%. During the experiments, cement-stabilized soil samples and lime-stabilized soil samples whose laser-induced model did not previously consume breakdown emission intensities were used to estimate the UCS of the modified soil samples. The ability of the models to accurately predict the UCS of the treated samples confirm its generalization strength and its suitability to be employed in estimating the UCS of any soil-related sample whose emission intensities can be obtained under the LIBS system.

Fourth Experiment: Determining Effects of Cement-Stabilized Soil Samples on Prediction Capability of the Models.

Figure 14A:
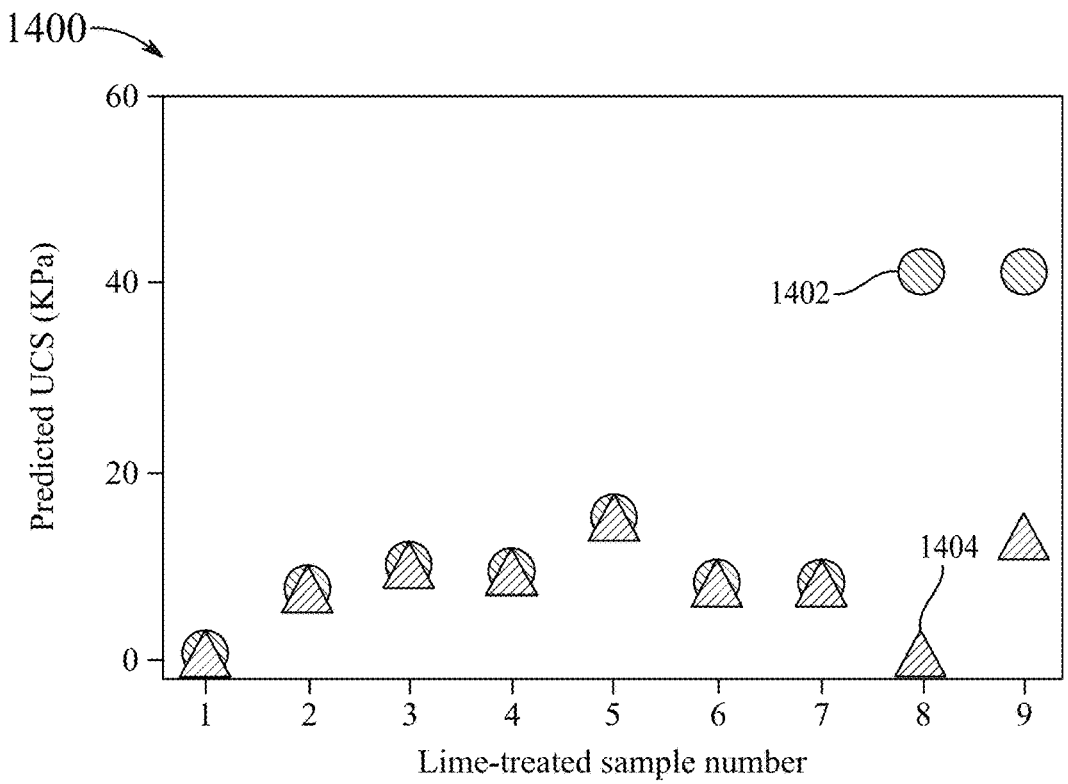
FIG. 14A is a graph representing UCS values determined by the SVR model for different lime-stabilized soil samples, according to aspects of the present disclosure.
Figure 14B:
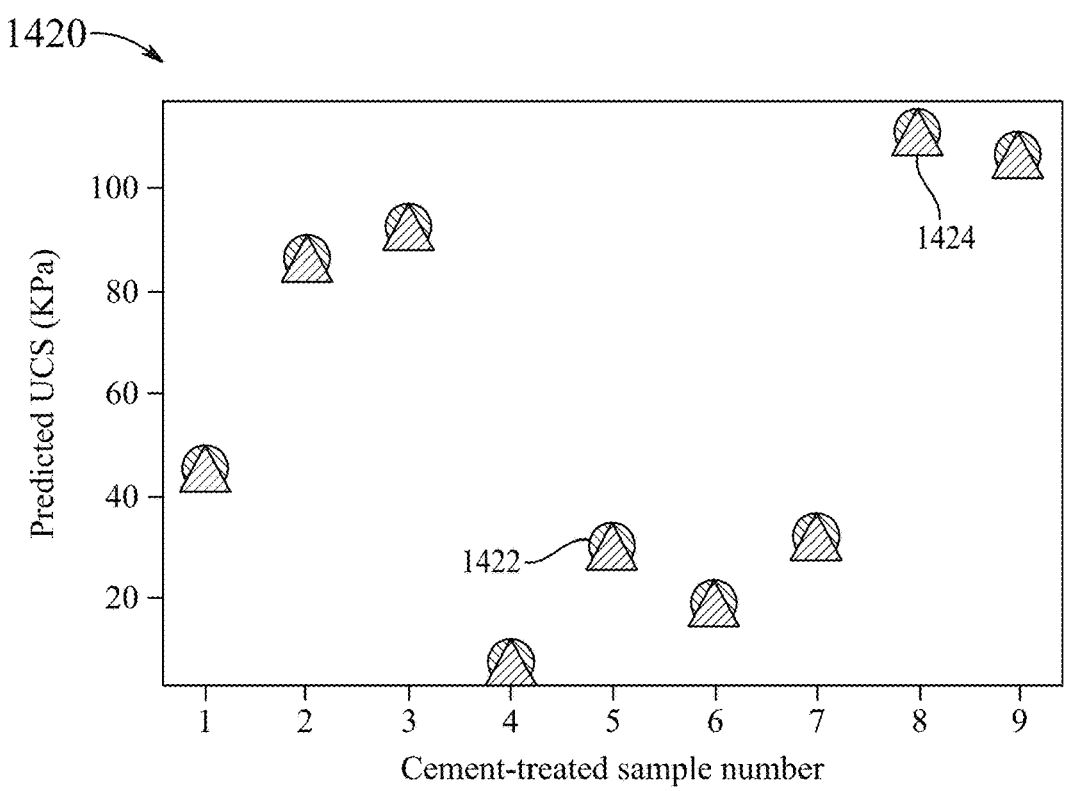
FIG. 14B is a graph representing UCS values determined by the SVR model for different cement-stabilized soil samples, according to aspects of the present disclosure.
Figure 14C:
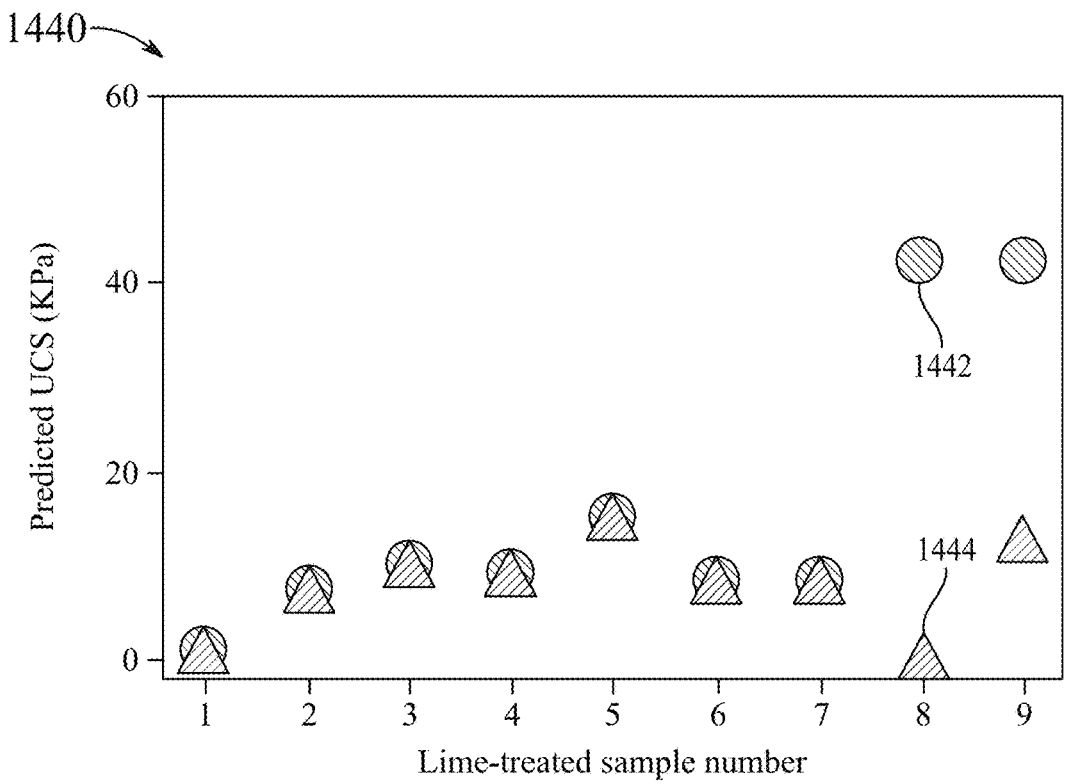
FIG. 14C is a graph representing UCS values determined by the boosted SVR model for different lime-stabilized soil samples, according to aspects of the present disclosure.
Figure 14D:
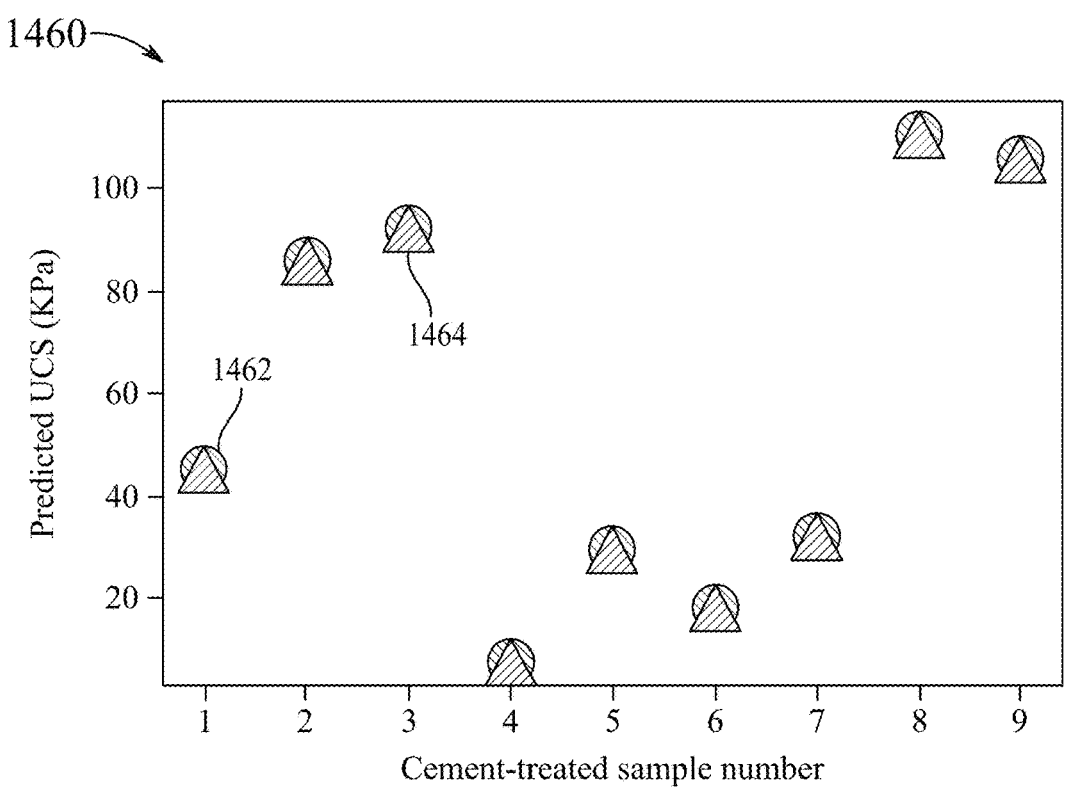
FIG. 14D is a graph representing UCS values determined by the boosted SVR model for different cement-stabilized soil samples, according to aspects of the present disclosure.

A fourth experiment was conducted to investigate the effects of cement-stabilized soil samples on the prediction capability of the models. Some soil samples were treated with cement and passed to the LIBS system (laser induced breakdown spectrometer 124) for elemental spectral emission measurements. In an example, UCS of the soil was measured in the laboratory using the standard procedure. The emission intensities of the constituent elements, water content, and bulk density were used as input features to estimate the already laboratory-measured UCS to validate the device 100. FIG. 14B and FIG. 14D show the cross plot between the predicted UCS values and the experimental UCS values of cement-stabilized soil samples using SVR model and boosted SVR model, respectively. The cross plot between the predicted UCS values and experimental UCS values of cement-stabilized soil samples obtained using DTR model and DTR-ADB model are presented in FIG. 15B and FIG. 15D, respectively. All models were able to predict the unknown UCS values to a degree of accuracy of more than 95% based on the correlation coefficient between the predicted value and experimental value. All models demonstrated the suitability of the developed models in estimating the UCS of a soil sample.

Fifth Experiment: Determining Effects of Lime-Stabilized Soil Samples on Prediction Capability of the Models Lime-treated soils demonstrate improved stabilization, impermeability, load-bearing characteristics, and enhanced workability, especially for soils beneath the road and similar works. Lime is often employed at construction sites to dry wet soil to improve the working surface and reduce downtime. It is, therefore, essential to train the device 100 which is configured to predict the UCS properties of such materials (lime).

A fifth experiment was conducted to investigate the effects of lime-stabilized soil samples on prediction capability of the models. The four developed models were individually applied to estimate the UCS of the lime-stabilized soil samples. The input features were extracted from the LIBS-generated elemental emission intensities of lime-stabilized soil samples. The predicted soil UCS exhibited high correlation coefficients with the actual UCS values, as depicted in FIG. 14A and FIG. 14C for SVR and boosted SVR models, respectively. The predicted UCS values for the lime-stabilized soil samples obtained from DTR model and boosted DTR model are presented in FIG. 15A and FIG. 15C, respectively. The four models have shown great promise in predicting the soil UCS of the lime-stabilized soil samples based on the emission intensities obtained from the LIBS system, water content, and bulk density of the soil as input features.

FIG. 14A is a graph 1400 representing UCS values determined by the SVR model for different lime-stabilized soil samples. Circular shaped objects 1402 represent the predicted (theoretical) UCS values. Triangular shaped objects 1404 represent the experimental UCS values.

FIG. 14B is a graph 1420 representing UCS values determined by the SVR model for different cement-stabilized soil samples. Circular shaped objects 1422 represent the theoretical UCS values. Triangular shaped objects 1424 represent the experimental UCS values.

FIG. 14C is a graph 1440 representing UCS values determined by the boosted SVR model for different lime-stabilized soil samples. Circular shaped objects 1442 represent the predicted UCS values. Triangular shaped objects 1444 represent the experimental UCS values.

FIG. 14D is a graph 1460 representing UCS values predicted by the boosted SVR model for different cement-stabilized soil samples. Circular shaped objects 1462 represent the predicted UCS values. Triangular shaped objects 1464 represent the experimental UCS values.

Figure 15A:
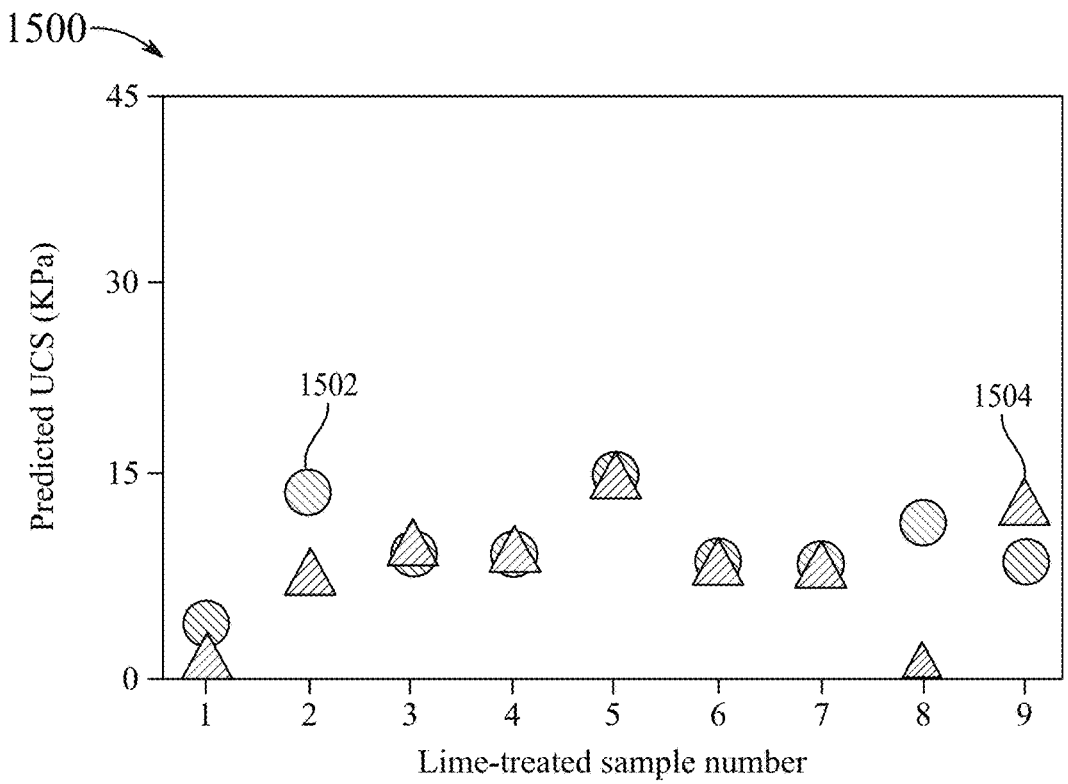
FIG. 15A is a graph representing UCS values predicted by the DTR model for different lime-stabilized soil samples, according to aspects of the present disclosure.

FIG. 15A is a graph 1500 representing UCS values predicted by the DTR model for different lime-stabilized soil samples. Circular shaped objects 1502 represent the predicted UCS values. Triangular shaped objects 1504 represent the experimental UCS values.

Figure 15B:
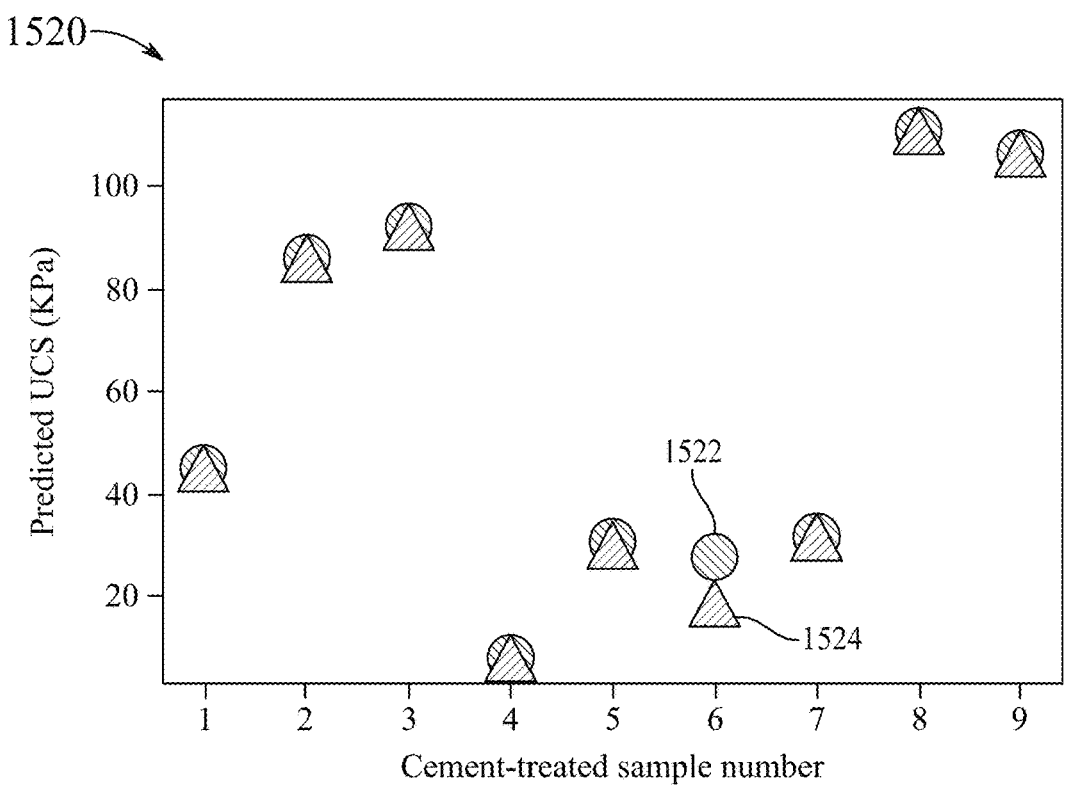
FIG. 15B is a graph representing UCS values predicted by the DTR model for different cement-stabilized soil samples, according to aspects of the present disclosure.

FIG. 15B is a graph 1520 representing UCS values determined by the DTR model for different cement-stabilized soil samples using DTR model. Circular shaped objects 1522 represent the predicted UCS values. Triangular shaped objects 1524 represent the experimental UCS values.

Figure 15C:
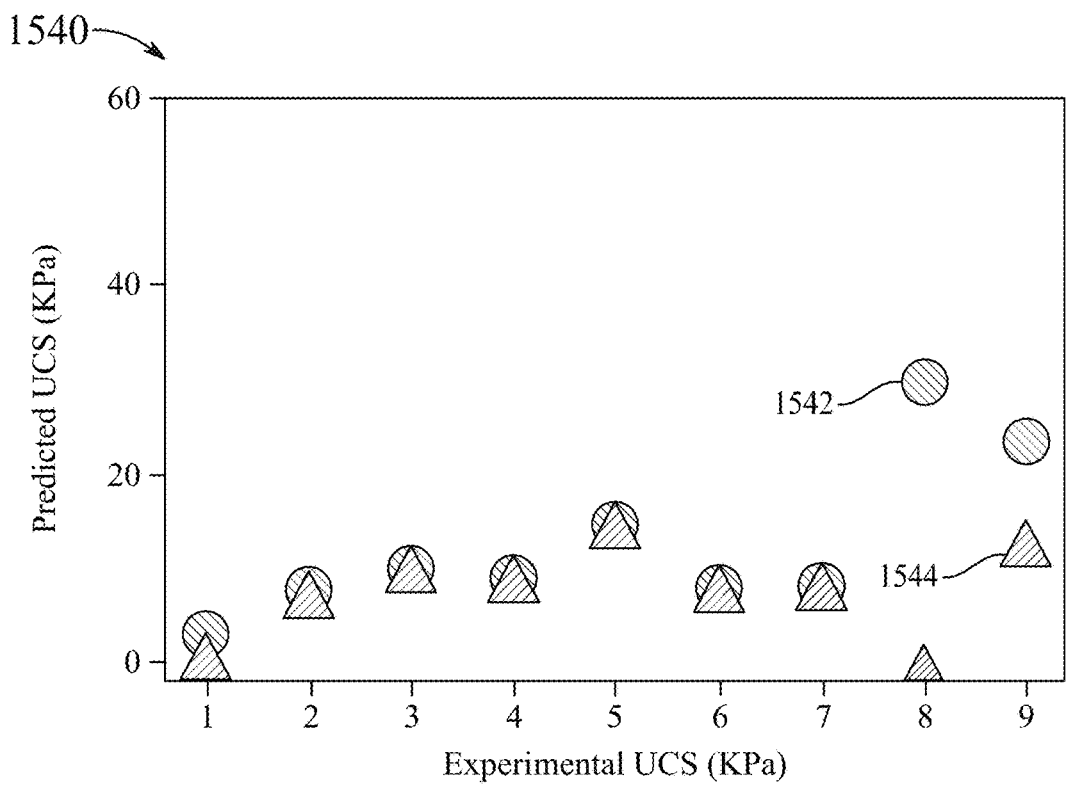
FIG. 15C is a graph representing UCS values predicted by the boosted DTR model for different lime-stabilized soil samples, according to aspects of the present disclosure.

FIG. 15C is a graph 1540 representing UCS values determined by DTR-ADB model for different lime-stabilized soil samples. Circular shaped objects 1542 represent the predicted UCS values. Triangular shaped objects 1544 represent the experimental UCS values.

Figure 15D:
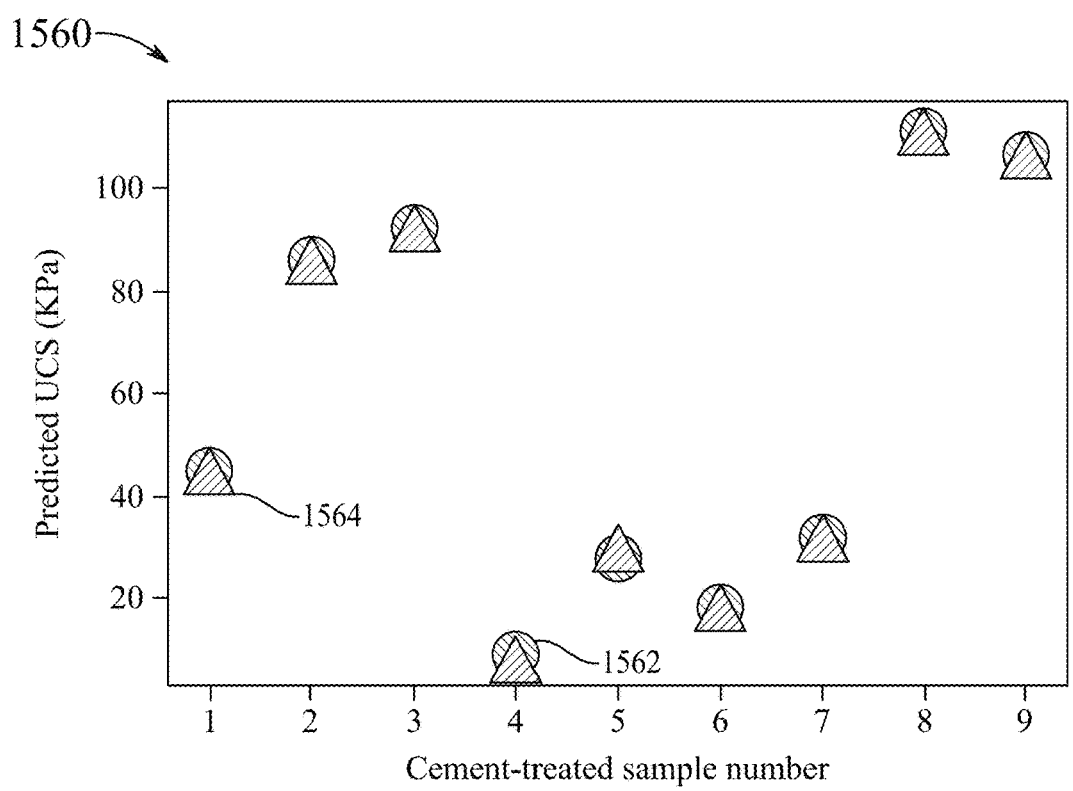
FIG. 15D is a graph representing UCS values predicted by the boosted DTR model for different lime-stabilized soil samples, according to aspects of the present disclosure.

FIG. 15D is a graph 1560 representing UCS values determined by DTR-ADB model for different cement-stabilized soil samples. Circular shaped objects 1562 represent the predicted UCS values. Triangular shaped objects 1564 represent the experimental UCS values.

In a summary, the device 100 is configured to:
1. Test soil samples from different locations;
2. Identify the elements present in the collected soil samples using the laser-induced breakdown spectroscopy and the concentrations of the identified elements;
3. Identify a plurality of physical properties of the soil sample (bulk density, moisture content, and UCS);
4. Employ the boosted DTR model (may alternatively use the boosted SVR model) and generate a complex pattern between the descriptors (elemental intensities generated by LIBS, water content, and bulk density) and the target variable representing soil UCS;
5. Display the UCS on the display screen of the field portable device; and
6. Transmit the UCS to either or both of the remote computer and the smart phone, which may assess the performance of the models based on the standard metric performance indicators ($R^2$-score, mean absolute error (MAE), root means square error (RMSE), and correlation coefficient (CC)) between the predicted and actual soil UCS values.

The first embodiment is illustrated with respect to FIG. 1A-FIG. 1C. The first embodiment describes the field portable device 100 for determining the UCS of a soil sample. The field portable device 100 includes a sample holder 114, a heating device 120, a scale 122, a spectrometer 124, a display screen 130, a power source 132, and a microprocessor 140. The sample holder 114 is configured to receive a soil sample. The sample holder 114 has a defined volume. The heating device 120 is configured to dry the soil sample for a specified time. The scale 122 is connected to the sample holder 114. The scale 122 is configured to measure a weight of the soil sample and a dried weight of the soil sample. The spectrometer 124 is configured to perform laser induced breakdown spectroscopy on the soil sample and generate spectral emission intensities of the soil sample. The microprocessor 140 is connected to the scale 122, the heating device 120, the spectrometer 124, the display screen 130 and the power source 132. The microprocessor 140 includes circuitry 142, a memory 144 and programming instructions stored therein that, when executed by one or more processors, cause the one or more processors to: calculate a bulk density of the soil sample, calculate a water content of the soil sample, actuate the spectrometer 124 to perform laser induced breakdown spectroscopy on the soil sample and generate the spectral emission intensities, apply the spectral emission intensities, the bulk density and the water content of each soil sample as input features to a trained DTR combined with an adaptive boosting classifier, predict the UCS of the soil sample, and display the UCS, the bulk density, the water content and the spectral emission intensities of the soil sample on the display screen 130.

In an aspect, the microprocessor 140 is configured to: receive an undried weight of the soil sample from the scale 122, actuate the heating device 120 to dry the soil sample for the specified time, receive a dried weight of the soil sample from the scale 122, and calculate the bulk density of the soil sample by dividing the dried weight by the volume.

In an aspect, the microprocessor 140 is configured to calculate the water content of each soil sample by subtracting the dried weight of the soil sample from the undried weight of the soil sample and dividing the difference by the weight of the dried soil sample.

In an aspect, the microprocessor 140 is configured to perform the laser induced breakdown spectroscopy (LIBS) by directing the spectrometer 124 to: transmit high-energy laser pulses onto an outer surface of the soil sample until a portion of the soil sample ablates and forms a plasma, cool the plasma to release high energy photons, capture the high energy photons, record the spectrum of emission intensities of the high energy photons, identify, by the microprocessor 140, each constituent element in the soil sample by matching the spectrum of emission intensities to a database of known emission spectra, and generate the spectral emission intensities of the constituent elements of the soil sample.

In an aspect, the field portable device further includes a global positioning system (GPS) receiver located in the housing 102 of the field portable device, wherein the GPS receiver 146 is operably connected to the microprocessor 140, wherein the microprocessor 140 is configured to record a location from which the soil sample is sourced.

In an aspect, the field portable device 100 further includes a hopper 148 located beneath the sample holder 114. The hopper 148 is configured to receive the soil sample from the sample holder 114 and store the store sample for further processing. The microprocessor 140 is operatively connected to the hopper 148 to receive and record a position of the soil sample within the hopper 148. The microprocessor 140 is configured to record the GPS location from which the soil sample was sourced.

In an aspect, the field portable device 100 further includes a communications device 136 operatively connected to the microprocessor 140. The communications device 136 is configured to transmit the GPS location of the soil sample and unconfined compressive strength to a remote computer 180.

In an aspect, the field portable device 100 further includes a near field antenna 138 operatively connected to the communications device 136. The communications device 136 is wirelessly connected by near field communications to a smart device 190 configured with a computer mapping application 195 for displaying the unconfined compressive strength of the soil sample and the GPS location on a map.

The second embodiment is illustrated with respect to FIG. 1A-FIG. 1C. The second embodiment describes a method for surveying a geographic area to determine an unconfined compressive strength of a soil layer of the geographic area. The method includes transporting a field portable device 100 equipped with a microprocessor 140 configured to determine the unconfined compressive strength of soil samples in the geographic area. The method includes collecting, with an auger 108, a soil sample of the soil layer. The method includes depositing the soil sample into a sample holder 114 of the field portable device 100, wherein the sample holder 114 has a defined volume. The method includes recording, with a scale 122 connected to the sample holder 114, an undried weight of the soil sample. The method includes drying, with a heating device 120, the soil sample for a specified time. The method includes recording, with the scale 122, a dried weight of the soil sample. The method includes performing, with a laser induced breakdown spectrometer 124, laser induced breakdown spectroscopy (LIBS) on the soil sample to generate spectral emission intensities of the soil sample. The method includes recording, by a global positioning system (GPS) receiver, a location of the soil sample. The method includes calculating, with a microprocessor 140 connected to the scale 122, the laser induced breakdown spectrometer 124 and the GPS receiver 146 to receive the undried weight, the dried weight, the spectral emission intensities and the location of the soil sample, respectively, the bulk density and the water content of the soil sample. The method includes applying, by the microprocessor 140, the bulk density, water content and spectral emission intensities to a trained DTR combined with an adaptive boosting classifier. The method includes predicting, by the trained DTR combined with an adaptive boosting classifier, the unconfined compressive weight of the soil sample. The method includes displaying, on a display screen 130 operatively connected with the microprocessor 140, the unconfined compressive strength, the bulk density, the water content and the spectral emission intensities of the soil sample.

In an aspect, the method further includes transmitting, by a communications device 136 operatively connected to the microprocessor 140, the location of the soil sample and unconfined compressive strength to a remote computer 180.

In an aspect, the method further includes transmitting, with a near field antenna operatively connected to the communications device 136, the location of the soil sample and unconfined compressive strength to a smart device 190 configured with a computer mapping application 195. The method further includes displaying the unconfined compressive strength of the soil sample and the location on a map on a display screen 130 of the smart device 190.

In an aspect, the method further includes collecting a plurality of soil samples. The method further includes predicting the unconfined compressive strength of each soil sample. The method further includes determining the location of each soil sample. The method further includes transmitting the prediction of the unconfined compressive strength, the location, the bulk density, the water content and the spectral emission intensities of each soil sample to a remote computer 180. The method further includes displaying, on a mapping application of the remote computer 180, the locations of each soil sample with the prediction of the unconfined compressive strength, the location, the bulk density, the water content and the spectral emission intensities.

The third embodiment is illustrated with respect to FIG. 1A-FIG. 1C. The third embodiment describes a method of determining an unconfined compressive strength of a soil sample. The method includes receiving a set of soil samples. The method includes performing laser induced breakdown spectroscopy (LIBS) on each soil sample to generate spectral emission intensities of each soil sample of the set of soil samples. The method further includes measuring a bulk density of each soil sample of the set of soil samples. The method further includes measuring a water content of each soil sample of the set of soil samples. The method further includes applying the spectral emission intensities, the bulk densities and the water contents of each soil sample as input features to a trained machine learning regressor combined with an adaptive boosting classifier. The method further includes determining, by the trained machine learning regressor combined with the adaptive boosting classifier, the unconfined compressive strength of each of the soil samples.

In an aspect, the method further includes measuring the bulk density by calculating, with a microprocessor 140, a volume of each soil sample of the set of soil samples. The method further includes weighing, with a scale 122, a weight of each soil sample of the set of soil samples. The method further includes drying, with a heating device 120, each soil sample of the set of soil samples for a specified time. The method further includes weighing, with the scale 122, a dried weight of each soil sample of the set of soil samples. The method further includes calculating, by the microprocessor 140, the bulk density of each soil sample of the set of soil samples by dividing the dried weight by the volume.

In an aspect, the method further includes calculating the water content of each soil sample by subtracting the dried weight of the soil sample from the weight of the soil sample before drying, and dividing by the weight of the dried soil sample.

In an aspect, the step of performing laser induced breakdown spectroscopy (LIBS) on each soil sample of the set of soil samples to generate the spectral emission intensities of the soil sample includes directing, by a laser, high-energy laser pulses onto an outer surface of the soil sample until a portion of the soil sample is ablated and forms a plasma. The method further includes cooling the plasma to release high energy photons. The method further includes capturing, with a spectrometer 124, the high energy photons. The method further includes recording, with the spectrometer 124, a spectrum of emission intensities of the high energy photons. The method further includes identifying, by a computing device connected to the spectrometer 124, each constituent element in each soil sample by matching the spectrum of emission intensities to a database of known emission spectra. The method further includes generating the spectral emission intensities of the constituent elements of each soil sample.

In an aspect, the method further includes training the machine learning regressor on 80% of a dataset of soil samples having known bulk densities, known water contents, known spectral emission intensities of the constituent elements and known unconfined compressive strengths. The method includes testing the machine learning regressor on a remaining 20% of the dataset of soil samples.

In an aspect, the trained machine learning regressor is a decision tree regressor which maps the spectral emission intensities, the bulk density and the water content of each soil sample to the unconfined compressive strength of the soil sample.

In an aspect, the step training the decision tree regressor includes selecting a depth of the decision tree regressor, applying the spectral emission intensities, the bulk density and the water content to the decision tree regressor, and predicting the unconfined compressive strength of each soil sample.

In an aspect, the step of training the machine learning regressor combined with the adaptive boosting classifier includes assigning a depth to the decision tree regressor, applying the input features including the spectral emission intensities, the bulk density and the water content of each soil sample of the dataset to the decision tree regressor, assigning equal weight to each of the spectral emission intensities, the bulk density and the water content to the decision tree regressor, generating, by the decision tree regressor, a first prediction of the unconfined compressive strength of the soil sample for the first depth, calculating a first root mean square error (RMSE) between the first prediction of the unconfined compressive strength and the known unconfined compressive strength, and comparing the first RMSE to a threshold value. When the first RMSE is less than the threshold value, the method includes outputting the first prediction as the unconfined compressive strength. When the first RMSE is greater than the threshold value, the method includes saving the weights of the first prediction, the unconfined compressive strength of the first prediction and the first RMSE. The step of training the machine learning regressor combined with the adaptive boosting classifier includes performing adaptive boosting by: identifying input features which are misclassified in the first prediction of the unconfined compressive strength, modifying the weights of the input features by increasing the weights of the weakly correlated input features, applying the input features with the modified weights to the decision tree regressor, generating, by the decision tree regressor, a second prediction of the unconfined compressive strength of the soil sample, calculating a second RMSE using the second prediction of the unconfined compressive strength and the known unconfined compressive strength, comparing the second RMSE to the first RMSE. When the second RMSE is less than the first RMSE, the method includes comparing the second RMSE to the threshold value. When the second RMSE is less than the threshold value, the method includes outputting the second prediction as the unconfined compressive strength and stop incrementing. When the second RMSE is greater than the threshold value, the method includes saving the modified weights of the second prediction, the unconfined compressive strength of the second prediction and the second RMSE, continuing identifying input features which are misclassified, increasing the weights of the misclassified input features, applying the reweighted input features to the decision tree classifier, and outputting predictions of the unconfined compressive strength until the RMSE is less than the threshold value, averaging the weights and predictions of unconfined compressive weight of each iteration, and outputting the average of the predictions as the unconfined compressive strength.

Next, further details of the hardware description of the computing environment of FIG. 1A-FIG. 1C according to exemplary embodiments is described with reference to FIG. 16.

Figure 16:
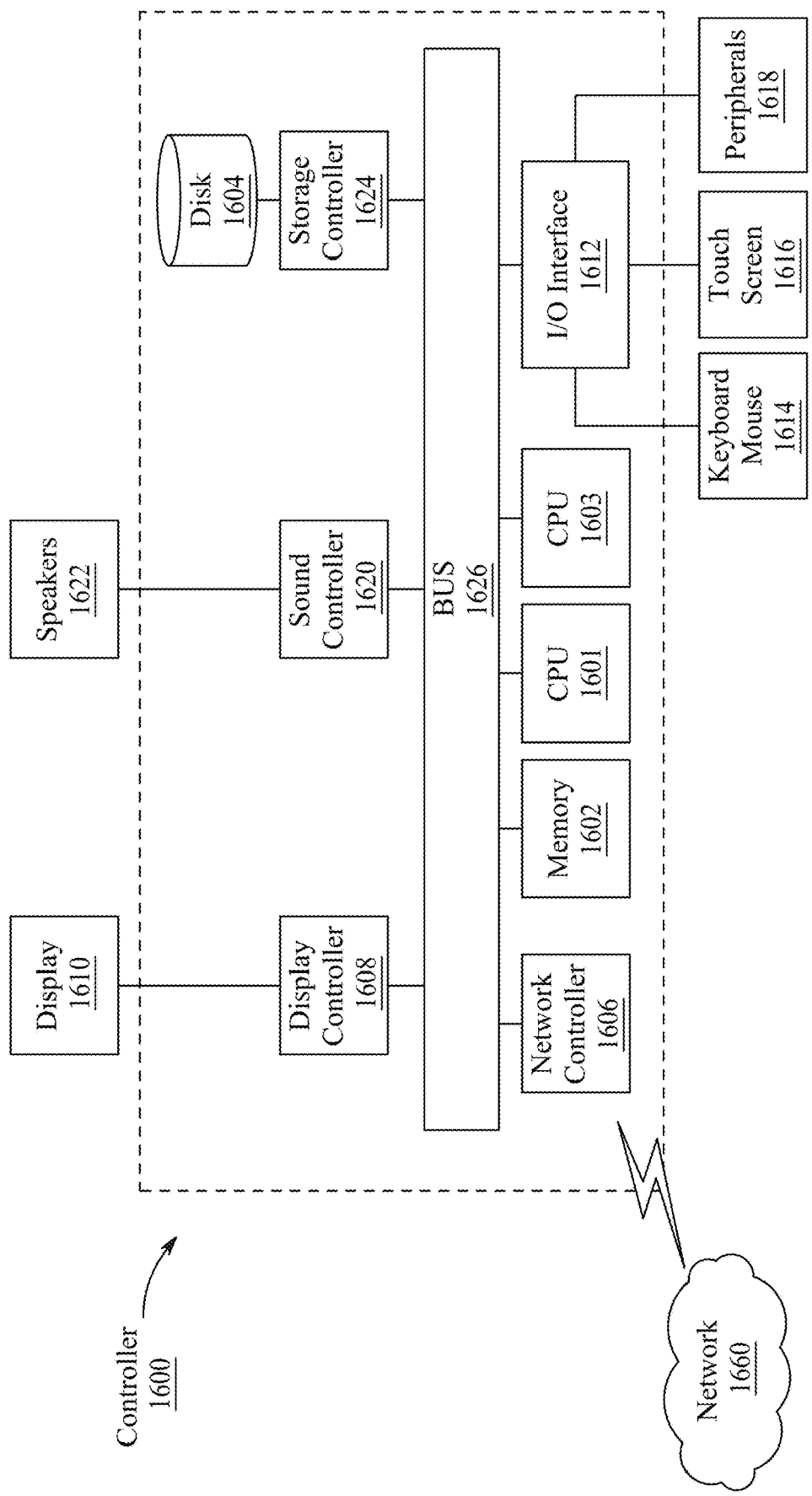
FIG. 16 is an illustration of a non-limiting example of details of computing hardware used in the computing system, according to aspects of the present disclosure.

In FIG. 16, a controller 1600 is described as representative of the microprocessor 140 of the field portable device 100 for determining the unconfined compressive strength of a soil sample of FIG. 1A-FIG. 1C in which microprocessor 140 is a computing device which includes a CPU 1601 which performs the processes described above/below. FIG. 16 is an illustration of a non-limiting example of details of computing hardware used in the computing system, according to exemplary aspects of the present disclosure. In FIG. 16, a controller 1600 is described which is a computing device (that includes the microprocessor 140) and includes a CPU 1601 which performs the processes described above/below. The process data and instructions may be stored in memory 1602. These processes and instructions may also be stored on a storage medium disk 1604 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 1601, 1603 and an operating system such as Microsoft Windows 7, UNIX, Solaris, LINUX, Apple MAC-OS and other systems known to those skilled in the art.

The hardware elements in order to achieve the computing device may be realized by various circuitry elements, known to those skilled in the art. For example, CPU 1601 or CPU 1603 may be a Xenon or Core processor from Intel of America or an Opteron processor from AMD of America, or may be other processor types that would be recognized by one of ordinary skill in the art. Alternatively, the CPU 1601, 1603 may be implemented on an FPGA, ASIC, PLD or using discrete logic circuits, as one of the ordinary skill in the art would recognize. Further, CPU 1601, 1603 may be implemented as multiple processors cooperatively working in parallel to perform the instructions of the inventive processes described above.

The computing device in FIG. 16 also includes a network controller 1606, such as an Intel Ethernet PRO network interface card from Intel Corporation of America, for interfacing with network 1660. As can be appreciated, the network 1660 can be a public network, such as the Internet, or a private network such as an LAN or WAN network, or any combination thereof and can also include PSTN or ISDN sub-networks. The network 1660 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 1608, such as a NVIDIA GeForce GTX or Quadro graphics adaptor from NVIDIA Corporation of America for interfacing with display 1610, such as a Hewlett Packard HPL2445w LCD monitor. A general purpose I/O interface 1612 interfaces with a keyboard and/or mouse 1614 as well as a touch screen panel 1616 on or separate from display 1610. General purpose I/O interface also connects to a variety of peripherals 1618 including printers and scanners, such as an OfficeJet or DeskJet from Hewlett Packard.

A sound controller 1620 is also provided in the computing device such as Sound Blaster X-Fi Titanium from Creative, to interface with speakers/microphone 1622 thereby providing sounds and/or music.

The general-purpose storage controller 1624 connects the storage medium disk 1604 with communication bus 1626, which may be an ISA, EISA, VESA, PCI, or similar, for interconnecting all of the components of the computing device. A description of the general features and functionality of the display 1610, keyboard and/or mouse 1614, as well as the display controller 1608, storage controller 1624, network controller 1606, sound controller 1620, and general purpose I/O interface 1612 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 17.

Figure 17:
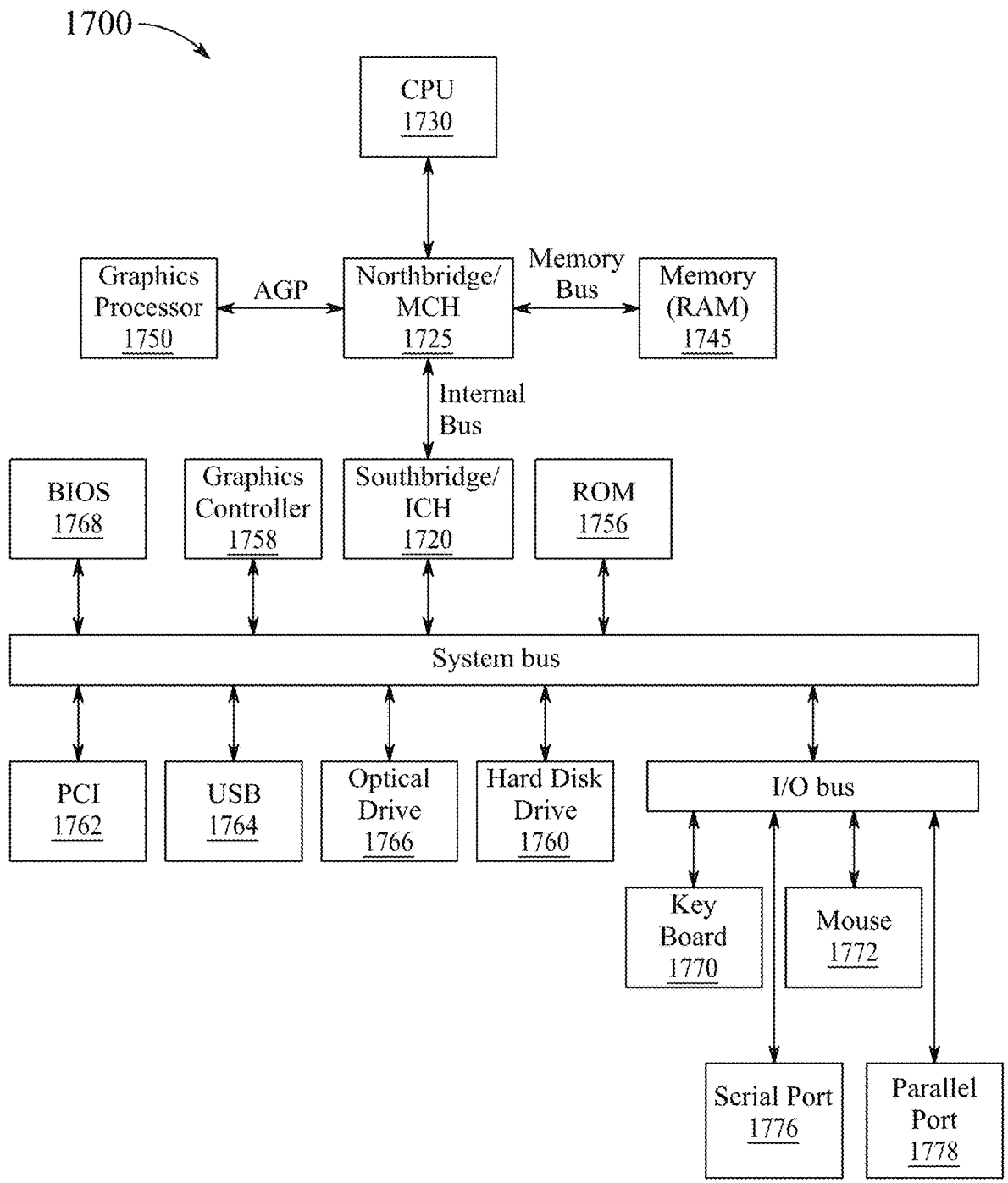
FIG. 17 is an exemplary schematic diagram of a data processing system used within the computing system, according to aspects of the present disclosure.

FIG. 17 shows a schematic diagram of a data processing system 1700 used within the computing system, according to exemplary aspects of the present disclosure. The data processing system 1700 is an example of a computer in which code or instructions implementing the processes of the illustrative aspects of the present disclosure may be located.

In FIG. 17, data processing system 1780 employs a hub architecture including a north bridge and memory controller hub (NB/MCH) 1725 and a south bridge and input/output (I/O) controller hub (SB/ICH) 1720. The central processing unit (CPU) 1730 is connected to NB/MCH 1725. The NB/MCH 1725 also connects to the memory 1745 via a memory bus, and connects to the graphics processor 1750 via an accelerated graphics port (AGP). The NB/MCH 1725 also connects to the SB/ICH 1720 via an internal bus (e.g., a unified media interface or a direct media interface). The CPU Processing unit 1730 may contain one or more processors and even may be implemented using one or more heterogeneous processor systems.

Figure 18:
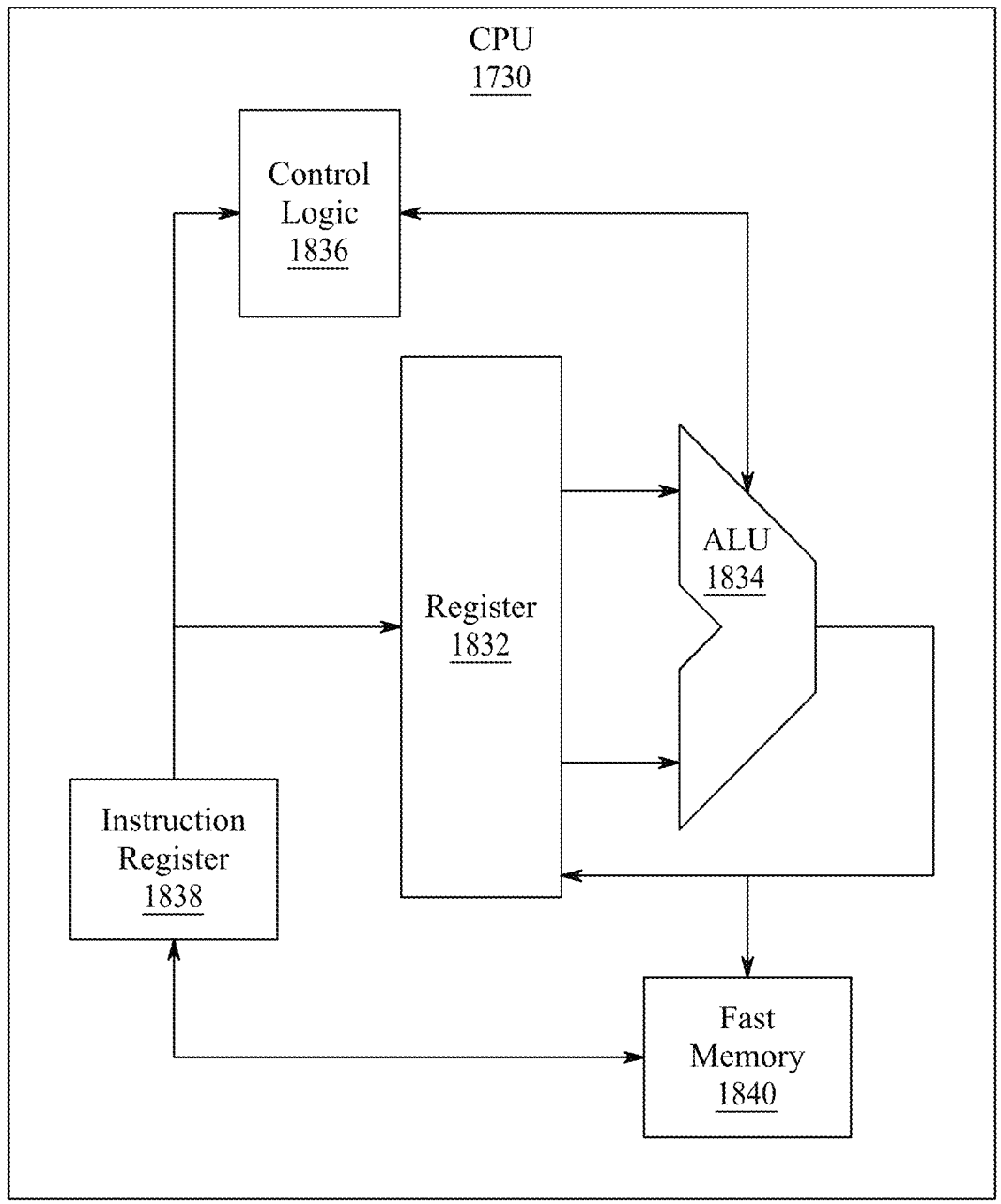
FIG. 18 is an exemplary schematic diagram of a processor used with the computing system, according to aspects of the present disclosure.

For example, FIG. 18 shows one aspects of the present disclosure of CPU 1730. In one aspects of the present disclosure, the instruction register 1838 retrieves instructions from the fast memory 1840. At least part of these instructions is fetched from the instruction register 1838 by the control logic 1836 and interpreted according to the instruction set architecture of the CPU 1730. Part of the instructions can also be directed to the register 1832. In one aspects of the present disclosure the instructions are decoded according to a hardwired method, and in another aspect of the present disclosure the instructions are decoded according to a microprogram that translates instructions into sets of CPU configuration signals that are applied sequentially over multiple clock pulses. After fetching and decoding the instructions, the instructions are executed using the arithmetic logic unit (ALU) 1834 that loads values from the register 1832 and performs logical and mathematical operations on the loaded values according to the instructions. The results from these operations can be feedback into the register and/or stored in the fast memory 1840. According to certain aspects of the present disclosures, the instruction set architecture of the CPU 1730 can use a reduced instruction set architecture, a complex instruction set architecture, a vector processor architecture, a very large instruction word architecture. Furthermore, the CPU 1730 can be based on the Von Neuman model or the Harvard model. The CPU 1730 can be a digital signal processor, an FPGA, an ASIC, a PLA, a PLD, or a CPLD. Further, the CPU 1730 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 17, the data processing system 1780 can include that the SB/ICH 1720 is coupled through a system bus to an I/O Bus, a read only memory (ROM) 1756, universal serial bus (USB) port 1764, a flash binary input/output system (BIOS) 1768, and a graphics controller 1758. PCI/PCIe devices can also be coupled to SB/ICH 1720 through a PCI bus 1762.

The PCI devices may include, for example, Ethernet adapters, add-in cards, and PC cards for notebook computers. The Hard disk drive 1760 and CD-ROM 1756 can use, for example, an integrated drive electronics (IDE) or serial advanced technology attachment (SATA) interface. In one aspect of the present disclosure the I/O bus can include a super I/O (SIO) device.

Further, the hard disk drive (HDD) 1760 and optical drive 1766 can also be coupled to the SB/ICH 1720 through a system bus. In one aspects of the present disclosure, a keyboard 1770, a mouse 1772, a parallel port 1778, and a serial port 1776 can be connected to the system bus through the I/O bus. Other peripherals and devices that can be connected to the SB/ICH 1720 using a mass storage controller such as SATA or PATA, an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 19:
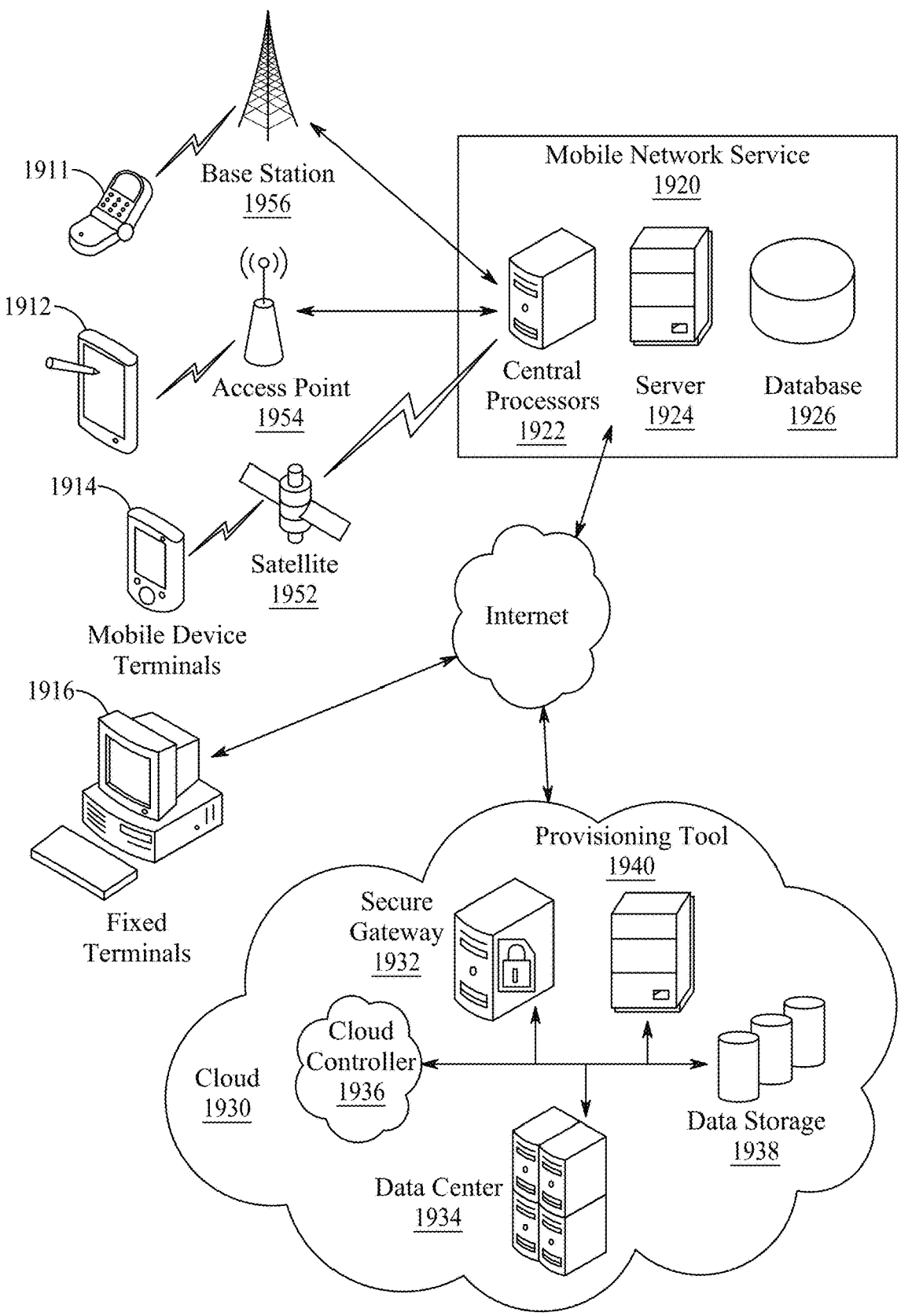
FIG. 19 is an illustration of a non-limiting example of distributed components that may share processing with the controller, according to aspects of the present disclosure.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 19, in addition to various human interface and communication devices (e.g., display monitors, smart phones, tablets, personal digital assistants (PDAs)). More specifically, FIG. 19 illustrates client devices including smart phone 1911, tablet 1912, mobile device terminal 1914 and fixed terminals 1916. These client devices may be commutatively coupled with a mobile network service 1920 via base station 1956, access point 1954, satellite 1952 or via an internet connection. Mobile network service 1920 may comprise central processors 1922, server 1924 and database 1926. Fixed terminals 1916 and mobile network service 1920 may be commutatively coupled via an internet connection to functions in cloud 1930 that may comprise security gateway 1932, data center 1934, cloud controller 1936, data storage 1938 and provisioning tool 1940. The network may be a private network, such as a LAN or WAN, or may be a public network, such as the Internet. Input to the system may be received via direct user input and received remotely either in real-time or as a batch process. Additionally, some aspects of the present disclosures may be performed on modules or hardware not identical to those described. Accordingly, other aspects of the present disclosures are within the scope that may be claimed.

The above-described hardware description is a non-limiting example of corresponding structure for performing the functionality described herein.

The positions of the components are illustrative and can be changed based on different designs and requirements.

Numerous modifications and variations of the present disclosure are possible in light of the above teachings. It is therefore to be understood that within the scope of the appended claims, the invention may be practiced otherwise than as specifically described herein.

The invention claimed is:

1. A field portable device for determining the unconfined compressive strength of a soil sample, comprising:
   a sample holder configured to receive a soil sample, wherein the sample holder has a defined volume;
   a heating device configured to dry the soil sample for a specified time;
   a scale connected to the sample holder, wherein the scale is configured to measure an undried weight of the soil sample and a dried weight of the soil sample;
   a spectrometer configured to perform laser induced breakdown spectroscopy on the soil sample and generate spectral emission intensities of the soil sample;
   a display screen;
   a power source;
   a microprocessor connected to the scale, the heating device, the spectrometer, the display screen and the power source, wherein the microprocessor includes circuitry, one or more processors, a memory storing programming instructions stored therein that, when executed by the one or more processors, cause the one or more processors to:
   calculate a bulk density of the soil sample;
   calculate a water content of the soil sample;
   actuate the spectrometer to perform laser induced breakdown spectrometry on the soil sample and generate the spectral emission intensities;
   apply the spectral emission intensities, the bulk density and the water content of each soil sample as input features to a trained decision tree regressor combined with an adaptive boosting classifier;
   predict the unconfined compressive strength of the soil sample; and
   display the unconfined compressive strength, the bulk density, the water content and the spectral emission intensities of the soil sample on the display screen.

2. The field portable device of claim 1, wherein the microprocessor is configured to:
   receive the undried weight of the soil sample from the scale;
   actuate the heating device to dry the soil sample for the specified time;
   receive the dried weight of the soil sample from the scale; and
   calculate the bulk density of the soil sample by dividing the dried weight by the volume.

3. The field portable device of claim 2, wherein the microprocessor is configured to calculate the water content of each soil sample by subtracting the dried weight of the soil sample from the undried weight of the soil sample and dividing the difference by the weight of the dried soil sample.

4. The field portable device of claim 1, wherein the microprocessor is configured to perform the laser induced breakdown spectrometry by directing the spectrometer to:
   transmit high-energy laser pulses onto an outer surface of the soil sample until a portion of the soil sample ablates and forms a plasma;
   cool the plasma to release high energy photons;
   capture the high energy photons;
   record the spectrum of emission intensities of the high energy photons;
   identify, by the microprocessor, each constituent element in the soil sample by matching the spectrum of emission intensities to a database of known emission spectra; and
   generate the spectral emission intensities of the constituent elements of the soil sample.

5. The field portable device of claim 1, further comprising:
   a global positioning system (GPS) receiver located in the housing of the field portable device, wherein the GPS receiver is operably connected to the microprocessor, wherein the microprocessor is configured to record a location from which the soil sample is sourced.

6. The field portable device of claim 5, further comprising:
   a hopper located beneath the sample holder, wherein the hopper is configured to receive the soil sample from the sample holder and store the store sample for further processing;
   the microprocessor is operatively connected to the hopper to receive and record a position of the soil sample within the hopper; and
   the microprocessor is configured to record the GPS location from which the soil sample was sourced.

7. The field portable device of claim 5, further comprising:
   a communications device operatively connected to the microprocessor, wherein the communications device is configured to transmit the GPS location of the soil sample and unconfined compressive strength to a remote computer.

8. The field portable device of claim 5, further comprising:
   a near field antenna operatively connected to the communications device;
   wherein the communications device is wirelessly connected by near field communications to a smart device configured with a computer mapping application for displaying the unconfined compressive strength of the soil sample and the GPS location on a map.

9. A method for surveying a geographic area to determine an unconfined compressive strength of a soil layer of the geographic area, comprising:
   transporting a field portable device equipped with a microprocessor configured to determine the unconfined compressive strength of soil samples to the geographic location;
   collecting, with an auger, a soil sample of the soil layer;
   depositing the soil sample into a sample holder of the field portable device, wherein the sample holder has a defined volume;
   recording, with a scale connected to the sample holder, an undried weight of the soil sample;

drying, with a heating device, the soil sample for a specified time;

recording, with the scale, a dried weight of the soil sample;

performing, with a laser induced breakdown spectrometer, laser induced breakdown spectroscopy on the soil sample to generate spectral emission intensities of the soil sample;

recording, by a global positioning system (GPS) receiver, a location of the soil sample;

calculating, with a microprocessor connected to the scale, the laser induced breakdown spectrometer and the GPS receiver to receive the undried weight, the dried weight, the spectral emission intensities and the location of the soil sample respectively, the bulk density and the water content of the soil sample;

applying, by the microprocessor, the bulk density, water content and spectral emission intensities to a trained decision tree regressor combined with an adaptive boosting classifier;

predicting, by the trained decision tree regressor combined with an adaptive boosting classifier, the unconfined compressive weight of the soil sample; and displaying, on a display screen operatively connected with the microprocessor, the unconfined compressive strength, the bulk density, the water content and the spectral emission intensities of the soil sample.

10. The method of claim 9, further comprising:

transmitting, by a communications device operatively connected to the microprocessor, the location of the soil sample and unconfined compressive strength to a remote computer.

11. The method of claim 9, further comprising:

transmitting, with a near field antenna operatively connected to the communications device, the location of the soil sample and unconfined compressive strength to a smart device configured with a computer mapping application; and displaying the unconfined compressive strength of the soil sample and the location on a map on a display screen of the smart device.

12. The method of claim 9, further comprising:

collecting a plurality of soil samples;

predicting the unconfined compressive strength of each soil sample;

determining the location of each soil sample;

transmitting the prediction of the unconfined compressive strength, the location, the bulk density, the water content and the spectral emission intensities of each soil sample to a remote computer; and displaying, on a mapping application of the remote computer, the locations of each soil sample with the prediction of the unconfined compressive strength, the location, the bulk density, the water content and the spectral emission intensities.

13. A method of determining an unconfined compressive strength of a soil sample, comprising:

receiving a set of soil samples;

performing laser induced breakdown spectroscopy on each soil sample to generate spectral emission intensities of each soil sample of the set of soil samples;

measuring a bulk density of each soil sample of the set of soil samples;

measuring a water content of each soil sample of the set of soil samples;

applying the spectral emission intensities, the bulk densities and the water contents of each soil sample as input features to a trained machine learning regressor combined with an adaptive boosting classifier; and determining, by the trained machine learning regressor combined with the adaptive boosting classifier, the unconfined compressive strength of each of the soil samples.

14. The method of claim 13, further comprising:

measuring the bulk density by:

calculating, with a microprocessor, a volume of each soil sample of the set of soil samples;

weighing, with a scale, a weight of each soil sample of the set of soil samples;

drying, with a heating device, each soil sample of the set of soil samples for a specified time;

weighing, with the scale, a dried weight of each soil sample of the set of soil samples; and calculating, by the microprocessor, the bulk density of each soil sample of the set of soil samples by dividing the dried weight by the volume.

15. The method of claim 14, further comprising:

calculating the water content of each soil sample by subtracting the dried weight of the soil sample from the undried weight of the soil sample before drying; and dividing by the weight of the dried soil sample.

16. The method of claim 13, wherein performing laser induced breakdown spectroscopy (LIBS) on each soil sample of the set of soil samples to generate the spectral emission intensities of the soil sample includes directing, by a laser, high-energy laser pulses onto an outer surface of the soil sample until a portion of the soil sample is ablated and forms a plasma;

cooling the plasma to release high energy photons; and capturing, with a spectrometer, the high energy photons;

recording, with the spectrometer, a spectrum of emission intensities of the high energy photons; and identifying, by a computing device connected to the spectrometer, each constituent element in each soil sample by matching the spectrum of emission intensities to a database of known emission spectra; and generating the spectral emission intensities of the constituent elements of each soil sample.

17. The method of claim 13, further comprising:

training the machine learning regressor on 80% of a dataset of soil samples having known bulk densities, known water contents, known spectral emission intensities of the constituent elements and known unconfined compressive strengths; and testing the machine learning regressor on a remaining 20% of the dataset of soil samples.

18. The method of claim 17, wherein the trained machine learning regressor is a decision tree regressor which maps the spectral emission intensities, the bulk density and the water content of each soil sample to the unconfined compressive strength of the soil sample.

19. The method of claim 18, wherein training the decision tree regressor comprises;

selecting a depth of the decision tree regressor;

applying the spectral emission intensities, the bulk density and the water content to the decision tree regressor; and predicting the unconfined compressive strength of each soil sample.

20. The method of claim 18, wherein training the machine learning regressor combined with the adaptive boosting classifier comprises:
- assigning a depth to the decision tree regressor;
- applying the input features including the spectral emission intensities, the bulk density and the water content of each soil sample of the dataset to the decision tree regressor;
- assigning an equal weight to each of the spectral emission intensities, the bulk density and the water content to the decision tree regressor;
- generating, by the decision tree regressor, a first prediction of the unconfined compressive strength of the soil sample for the first depth;
- calculating a first root mean square error (RMSE) between the first prediction of the unconfined compressive strength and the known unconfined compressive strength;
- comparing the first RMSE to a threshold value;
- when the first RMSE is less than the threshold value, outputting the first prediction as the unconfined compressive strength;
- when the first RMSE is greater than the threshold value,
  - saving the weights of the first prediction, the unconfined compressive strength of the first prediction and the first RMSE;
  - performing adaptive boosting by:
    - identifying input features which are misclassified in the first prediction of the unconfined compressive strength;
    - modifying the weights of the input features by increasing the weights of the weakly correlated input features;
    - applying the input features with the modified weights to the decision tree regressor;
    - generating, by the decision tree regressor, a second prediction of the unconfined compressive strength of the soil sample;
- calculating a second RMSE using the second prediction of the unconfined compressive strength and the known unconfined compressive strength;
- comparing the second RMSE to the first RMSE;
- when the second RMSE is less than the first RMSE, comparing the second RMSE to the threshold value;
- when the second RMSE is less than the threshold value, outputting the second prediction as the unconfined compressive strength, and stop incrementing;
- when the second RMSE is greater than the threshold value:
- saving the modified weights of the second prediction, the unconfined compressive strength of the second prediction and the second RMSE;
- continuing identifying input features which are misclassified, increasing the weights of the misclassified input features, applying the reweighted input features to the decision tree classifier, and outputting predictions of the unconfined compressive strength until the RMSE is less than the threshold value;
- averaging the weights and predictions of unconfined compressive weight of each iteration; and
- outputting the average of the predictions as the unconfined compressive strength.

* * * * *